(12) United States Patent
Shany et al.

(10) Patent No.: US 8,535,622 B2
(45) Date of Patent: Sep. 17, 2013

(54) SPERM SEPARATION SYSTEM

(75) Inventors: Vered Shany, Ramat-Gan (IL); Isaac Tavori, Ramat-Gan (IL)

(73) Assignee: Lotus Bio (Nymphaea) Ltd, Ramat-Gan (IL)

(*) Notice: Subject to any disclaimer, the term of this patent is extended or adjusted under 35 U.S.C. 154(b) by 142 days.

(21) Appl. No.: 13/265,115

(22) PCT Filed: Apr. 22, 2010

(86) PCT No.: PCT/IL2010/000329
§ 371 (c)(1),
(2), (4) Date: Oct. 18, 2011

(87) PCT Pub. No.: WO2010/122562
PCT Pub. Date: Oct. 28, 2010

(65) Prior Publication Data
US 2012/0052485 A1    Mar. 1, 2012

Related U.S. Application Data

(60) Provisional application No. 61/171,785, filed on Apr. 22, 2009.

(51) Int. Cl.
*B01L 3/00* (2006.01)
*G01N 1/00* (2006.01)

(52) U.S. Cl.
USPC ........... 422/527; 422/547; 422/557; 422/559; 436/63; 436/174; 436/807

(58) Field of Classification Search
USPC ................ 422/527, 547, 557, 559; 436/63, 436/174, 807
See application file for complete search history.

(56) References Cited

U.S. PATENT DOCUMENTS

| 4,294,931 | A | 10/1981 | Levin et al. |
| 5,686,302 | A | 11/1997 | Zech |
| 2005/0026274 | A1 | 2/2005 | Zech |
| 2006/0110821 | A1 | 5/2006 | Brickwood |
| 2008/0311653 | A1 | 12/2008 | Abed |
| 2009/0023164 | A1 | 1/2009 | Golding et al. |
| 2010/0222196 | A1* | 9/2010 | Ito et al. ............ 494/27 |

OTHER PUBLICATIONS

International Search Report and Written Opinion dated Aug. 10, 2010 in corresponding International Application No. PCT/IL2010/000329.

* cited by examiner

*Primary Examiner* — Monique Cole
(74) *Attorney, Agent, or Firm* — The Law Office of Michael E. Kondoudis

(57) ABSTRACT

The present invention provides a naturally based Sperm Separation System (SSS) for separation of at least a portion of sperm cell populations (SCP) within an original semen sample, such that an enriched SCP sample is obtained, comprising a a sperm separation device, comprising ι) a first chamber adapted to contain at least a portion of said original semen sample, said first chamber is characterized by predetermined 3D shape and volume, V, said first chamber is bounded by a rim such that said orginal sample is kept below said rim, n) a second chamber in physical communication with said first chamber and said nm, said second chamber is characterized by predetermined 3D shape and volume, V1, said second chamber is adapted to reside said enriched SCP sample, b incubation means, adapted to socket at least one of said cell separation device and to homogeneously thermoregulate the temperature within the same.

25 Claims, 16 Drawing Sheets

Fig 2N
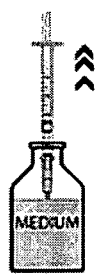
Fig 2O
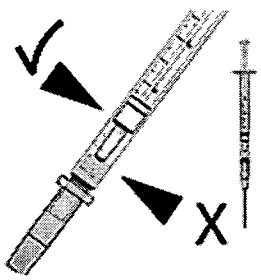
Fig 2P
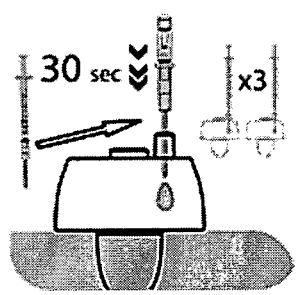
Fig 2Q
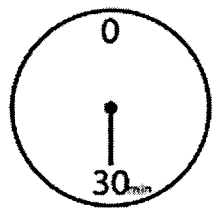
Fig 2R
Fig 2S
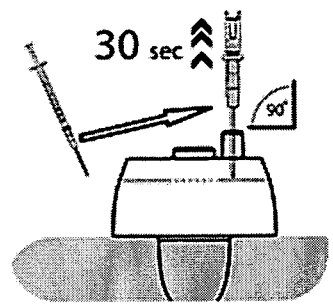

Fig. 5A
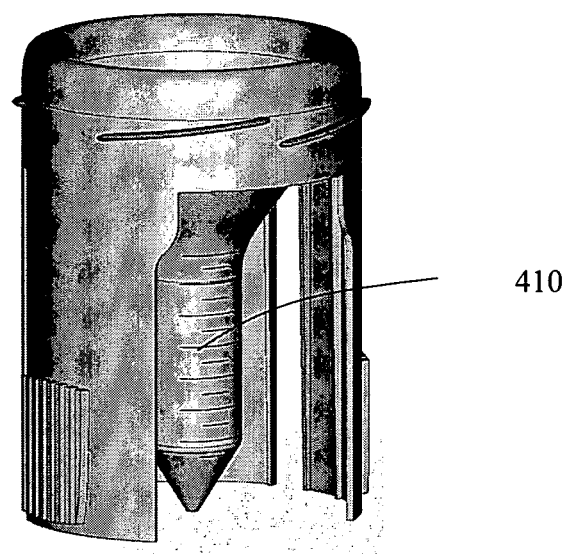
410
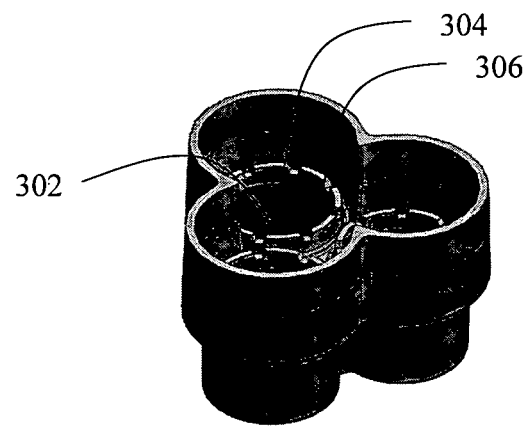
304
306
302
Figure 5B
306
302
304
Figure 5C

SPERM SEPARATION SYSTEM

FIELD OF THE DISCLOSURE

The present invention provides a device and method for processing a biologic sample, capable of sperm cells separation and/or preparation for treatment and/or diagnosis.

CROSS REFERENCES

U.S. Provisional Patent Application No. 60/981,856, filed Oct. 23, 2007; PCT-publication no. WO/2009/053927; and, PCT publication no. WO/2009/053928 are incorporated herein by reference in its entire

BACKGROUND

Infertility has been recognized as a public health issue worldwide by the World Health Organization (WHO) (Boivin J et al 2007, Human Reproduction Vol. 22: 1506-1512). Infertility is defined as 12 months of frequent, unprotected intercourse during which pregnancy has not occurred. An estimated 10% to 15% of couples in the United States are infertile (Jose-Miller and Boyden, 2007). The problem occurs worldwide (Aitken et al., 2006; Ashkani et al., 2006; Bayasgalan et al., 2004; DSouza et al., 2004; Jensen et al., 2005; Mehta et al., 2006; Qadan et al., 2007; Sallmen et al., 2003; Sharp 2000; Sokol et al., 2006; Su et al., 2006; Swai et al., 2006; Swan et al., 2003; Thonneau et al., 1991 and Toppari et al., 2002), with increasing rate over the last decades (Aitken 2006). One of the reasons is a drop in testosterone concentrations of about 1.2% per year, or about 17% overall between 1987 and 2004 (Travison et al, 2007). In about 30% of cases the two partners are jointly responsible for childlessness. In an additional 60% of cases, each partner is the sole cause of infertility (30% each). In 10% no explanation can be found, and the sterility is called "idiopathic" or "unexplained infertility" (Crazzolara et al., 2007).

Today, semen assessment and sperm cells enrichment are done only in private or public male fertility laboratories, not accessible to patients due to the need of qualified technicians and equipment.

Human spermatozoa display marked heterogeneity, and therefore a variety of sperm abnormalities can be found in semen samples—even in those of fertile men (Nallella et al., 2006). To date, no single laboratory test can assess a man's total fertility (Evenson, 1999). A combination of sperm characteristics, such as semen volume (Nallella et al., 2006), sperm count, and percentage of motile (Nallella et al., 2006; Guzick et al., 2001) and normal forms (Nallella et al., 2006; Guzick et al., 2001; Bartoov et al., 2002), considered in correct proportions, provides the best diagnostic profile that could distinguish between fertile and suspected infertile male groups (Nallella et al., 2006; Guzick et al., 2001). Other parameters, such as white blood cell concentration in the semen, can also affect sperm function (Wolff, 1995).

IUI is one of the most frequently used fertility treatments for sub-fertile couples (The ESHRE Capri workshop group, 2009; Bensdrop et al., 2007). It is widely accepted that sperm motility, and the percentages of progressively motile sperm cells and of spermatozoa with normal morphology are the best predictors of pregnancy by IUI (Boomsma et al., 2007; Keck et al., 1997). To this end, various semen preparation techniques have been developed to separate the motile, morphologically normal spermatozoa (Allamaneni et al., 2005) from the rest. The classical swim-up method was developed by Mahadevan & Baker (Mahadevan and Baker, 1984). More complicated techniques were introduced later (Allamaneni et al., 2005). All these techniques are based on cell migration, density gradient centrifugation, and filtration. Movement of the spermatozoa is an essential prerequisite for the migration and swim upmethods, whereas the density gradient centrifugation and filtration techniques are based on a combination of sperm cell motility and their retention at phase borders and adherence to filtration matrices (Henkel and Schill, 2003).

The ideal sperm separation and/or preparation technique should (a) be quick, easy, and cost-effective, (b) isolate as many motile spermatozoa as possible, (c) not cause sperm damage or any physiological alterations of the separated sperm cells, (d) eliminate dead spermatozoa and other cells, including leukocytes and bacteria, and (e) allow the processing of larger volumes of ejaculates (Henkel and Schill, 2003).

Currently there are numerous number of techniques for sperm cells separation:

Sperm wash. said technique is a simple centrifugation wash and subsequent re-suspension of the male sperm cells.

Cost: Relatively high per procedure (disposables and medium per semen sample of 3 ml)

Disadvantages: such procedure is most likely not removing the deadspermatozoa and other cellular elements of semen (leukocytes, epithelial cells, anucleate cytoplasmic bodies, particulate debris, immature sperm cells and immotile sperm cells). Centrifugal pelleting of unselected sperm populations from human ejaculates causes the production of reactive oxygen species, that inducing irreversible damage to the spermatozoa and impairment of their fertilization ability (Mortimer, 1994). Centrifugation is needed.

Swim-up procedure: such procedure is based on the active movement of spermatozoa from the centrifuged prewashed cell pellet or directly from the liquefied semen into an overlaying medium during 60 minutes. Swimming sperm cells are selected. The procedure requires: Centrifuge (an optional), incubator, a 15 ml cone tube, 1.2 ml of sperm medium. Extra medium is needed if centrifugation is done or multiple tubes are used.

Costs: Relatively high costs per procedure (disposables and medium per semen sample of 3 ml, without and with pre-wash, respectively).

Disadvantages: restricted to ejaculates with high sperm count and motility, low yield, spermatozoa can be massively damaged by reactive oxygen species, significant decrease of the percentage of normally chromatin-condensed spermatozoa (Henkel & Schill, 2003). Furthermore, it is known to require a very delicate handling, and might be contaminated due to the procedure process. Incubator and centrifuge are needed. A significant drawback for such a procedure is the fact that it must be performed by a qualified fertility laboratory technician due to method complexity Density gradient centrifugation: comprised of continuous or discontinuous gradients. The ejaculate is placed on top of the density media with higher density and is then centrifuged (for 15-30 minutes). Highly motile spermatozoa move actively in the direction of the sedimentation gradient and can therefore penetrate the boundary quicker than poorly motile or immotile cells, thus, highly motile sperm cells are enriched in the soft pellet at the bottom. Centrifugation is needed. Centrifugal pelleting of unselected sperm populations from human ejaculates causes the production of reactive oxygen species, that inducing irreversible damage to the spermatozoa and impairment of their fertilization ability (Mortimer, 1994), moreover dead and moribund spermatozoa and other cellular elements of semen (leukocytes, epithelial cells, anucleate cytoplasmic bodies, particulate debris, immature sperm cells and immotile sperm cells) can be found in the final pellet.

Costs: Relatively high costs per procedure (disposables, 2 gradients and medium).

Disadvantages: production of good interphase between the different media is a more time-consuming, potential risk of endotoxins contamination, Percoll® may no longer be used IVF/ICSI (Henkel & Schill, 2003). Centrifugation is required. furthermore, such a procedure is performed only by a qualified e fertility laboratory technician due to method complexity.

Less frequently used techniques for sperm cells selection in laboratory include the following:

Migration-sedimentation: a swim-up technique combined with a sedimentation step. Spermatozoa swim up directly from liquefied semen into the supernatant medium and subsequently sediment in a cone. No centrifugation is needed. The procedure is conducted in a special chamber with a unique structure: a small tube creating a well within a larger tube. It is commercially produced: MSC1 (R1, U.K.).

Costs: Relatively high costs. In such a procedure the medium is also needed in the same volume of the semen sample which elevates the costs even more.

Disadvantages: since the motile sperm cells are isolated into said larger tube filled with sperm separation medium, the concentration of the same is diluted. Thus, the above mentioned method is restricted to ejaculates of high sperm count and good motility, has a very low recovery rate, special glass or plastic tubes are required, tubes are more expensive and relatively sensitive, for repeated use in IVF glass and plastic tubes must be sterilized (Henkel & Schill, 2003). More than 1 chamber is required for a 3 ml semen sample.

Examples of systems whilst using the Migration-sedimentation technique:

ZSC-II: Conducted in a unique geometric configuration of the columns, which includes the conical cavity inside the ZSC. Combines the "swim-up/swim-down" phenomenon. Washes the sperm cells. Yielding a high-quality, morphologically normal, motile spermatozoa (according to manufacturer).

Disadvantages of the ZSC-II: High costs per procedure, lab top incubator (dry bath) is needed (for 45-60 min), suitable for 2 ml semen sample only (medium is needed in the same volume of the semen sample).

Multi-ZSC: combines the "swim-up/swim-down" phenomenon. Washes and simultaneously selects sub-populations of spermatozoa, no dilution and centrifugation. Yielding a high-quality, morphologically normal, physiologically superior motile spermatozoa (according to manufacturer). Dry bath or incubator are needed (again as before, the medium is needed in the same volume of the semen sample).

Disadvantages of the Multi-ZSC: Very high costs (approx.100$ per procedure).

Glass wool filtration: motile spermatozoa are separated from immotile sperm cells by means of densely packed glass wool fibres. The principle of this sperm separation technique lies in both the self-propelled movement of the spermatozoa and the filtration effect of the glass wool. A centrifugation step will be necessary to remove the seminal plasma (Henkel & Schill, 2003).

Disadvantages of the Glass wool filtration: more expensive (than swim up technique), the filtrate is not as clean as it is with other sperm separation methods, remnants of debris are still present (Henkel & Schill, 2003). Self prepared (Van den Bergh et al., 1997), or marketed (SpermFertil® columns from Mello Holzhausen, Germany).

Sephadex columns: sperm separation by means of Sephadex beads. (SpermPrep: ZDL Inc., Lexington, Ky., US). Pre-wash of the semen is needed (generation of free radicals). An improved column (SpermPrep II) allows semen filtration after dilution 1:1 with culture medium. Price: Relatively high costs per procedure (for the disposables including the beads only. Medium is needed in the same volume of the semen sample Disadvantages of the Sephadex columns: High cost per procedure Thus the above described methods require laboratory skills and equipment, frequently use external mechanical handling, or produce low yields of motile sperm cells.

Those traditional laboratory techniques require a designated laboratory, using a microscope and other laboratory equipment.

The main drawbacks are as follows:
  Accessibility: Male fertility laboratories are not as accessible to patient as the treating doctor—longer time to result & treatment
  Availability: No real time results
  Cost: Semen analysis in a laboratory costs 150$-400$. Relatively high.

Therefore there is a long felt need for rapid results, faster diagnostic benefits, better patient care by improving the time to treatment (TAT) in a point-of-care (POC) near-patient, for example in a doctor's clinic, and as a result decrease frustration, anxiety and uncertainty. Furthermore, Male fertility diagnostics and treatment is an underserved market. Semen assessment and sperm preparation are done in male fertility laboratories. Patients travel from Obstetrics and gynecology (OB/GYN) clinic to these facilities and back for each procedure. This time delay and logistics needed reduce treatment results. OB/GYN doctors must be available to deliver fertility treatments and ART as soon as patients return from fertility laboratories. OB/GYN doctors located far from fertility laboratories face a real accessibility challenge on their way to perform the IUI procedure.

Therefore, it is a long and unmet need to provide a sperm separation/preparation system and technique, intended to separate motile sperm cells in a semen sample, which overcome the above described drawbacks.

Furthermore, there is an unmet need to provide a sperm separation/preparation system which is simple to operate, requires no preliminary training and can be performed by doctors and healthcare professionals.

Such a system should be adapted for use in the doctor's office, clinics, laboratories and even home use.

Furthermore there is an unmet need to provide a sperm separation system which is based upon a natural separation procedure (i.e., no external interference, e.g., centrifuge, is operated to separate said sperm sample), resulting in high yield of sperm cells with desired characteristics for usage in fertility treatments.

Furthermore there is an unmet need to provide a sperm separation system which provides an enriched semen sample with high concentration of progressively motile sperm cells.

SUMMARY

It is one object of the present invention to provide a naturally based Sperm Separation System (SSS) for separation of at least a portion of sperm cell populations (SCP) characterized by (i) motility in a range between about 5 μm/s to about 15 μm/s at 37°; (ii) slow progressive motility in a range between about 15 μm/s at 37° to about 25 μm/s at 37°; (iii) rapid progressive motility of at least 25 μm/s at 37° and 20 μm/s at 20°; (iv) at least 90% motile sperm cells, having an average of at least 32% normal morphology; or any combination thereof, within an original semen sample, such that an enriched SCP sample is obtained; said SSS comprising:

a. a sperm separation device, comprising:
  i) at least one first chamber adapted to contain at least a portion of said original semen sample; said first chamber is characterized by pre-determined 3D shape and volume, V; said first chamber is bounded by a rim such that said original semen sample is kept below said rim; wherein said rim is crenellated shaped; and,
  ii) at least one second chamber in physical communication with said first chamber and said rim; said second chamber is characterized by pre-determined 3D shape and volume, $V_1$, wherein said $V_1$ is substantially smaller than V;
said second chamber is adapted to reside said enriched SCP sample; said enriched SCP sample comprising at least a portion of said SCP crossing through the crenellations in said crenellated shaped rim such that said separation of said SCP from said original semen sample is obtained and said enriched SCP sample is provided;

b. incubation means, adapted to socket at least one of said cell separation device and to homogeneously thermoregulate the temperature within the same;

wherein said pre-determined 3D shape of said first and second chambers and said crenellations in said rim enables at least one of the following is held true:
  i) efficacy of said SSS is at least 95%;
  ii) the total number of motile CSP separated into said second chamber is at least $4*10^6$ as examined with phase contrast or light microscopes, when said original semen sample is a NORMAL sample as defined by WHO 1999 Appendix IA clause 2.5 and comprises at least $5*10^6$ [motile CSP/ml];
  iii) the concentration of motile CSP separated into said second chamber is at least $4*10^6$ [cell/ml] as measured with phase contrast or light microscopes when the concentration of motile CSP in said original semen sample is at least $5*10^6$ [motile sperm cell/ml];
  iv) the total number of progressive motile CSP separated into said second chamber is at least $2*10^6$ as measured with phase contrast or light microscopes, when said original semen sample comprises at least $2.5*10^6$ [progressive motile CSP/ml];
  v) the average percentage of CSP having normal morphology in said enriched sample is at least 32% in as measured with phase contrast or microscopes when said original semen sample comprises an average of at least 18% CSP having normal morphology.

It is another object of the present invention to provide the SSS as define above, wherein said $V_1$ equals to said V.

It is another object of the present invention to provide the SSS as define above, wherein said first chamber is dimpled-shaped.

It is another object of the present invention to provide the SSS as define above, wherein said first chamber and said second are co-axial such that said second chamber is peripheral and circumferentially encircles said first chamber.

It is another object of the present invention to provide the SSS as define above, wherein said first chamber and said second are in a side by side configuration.

It is another object of the present invention to provide the SSS as define above, wherein said first chamber and said second are in a pile configuration.

It is another object of the present invention to provide the SSS as define above, wherein said pre-determined 3D shape of said first chamber is characterized by a cross sectional area of circular and is defined by radius R.

It is another object of the present invention to provide the SSS as define above, wherein said pre-determined 3D shape of said second chamber is characterized by a cross sectional area of circular and is defined by radius $R^1$.

It is another object of the present invention to provide the SSS as define above, wherein said pre-determined 3D shape of said first chamber is characterized by a cross sectional area having n ribs where n is an integer higher than or equals to 3, or any combination thereof.

It is another object of the present invention to provide the SSS as define above, wherein said pre-determined 3D shape of said second chamber is characterized by a cross sectional area having n ribs where n is an integer higher than or equals to 3, or any combination thereof.

It is another object of the present invention to provide the SSS as define above, wherein said SSS increases the efficacy of said separation and the enrichment of said SCP within said enriched SCP sample such that said increase is greater than the sum of said pre-determined 3D shape of said first and second chamber effectiveness and said crenellations in said rim effectiveness.

It is another object of the present invention to provide the SSS as define above, wherein said SCP are adapted to cross through or above the crenellations in said crenellated shaped rim into said second chamber upon introduction of a support medium into either said first chamber and/or said second chamber such that said support medium is in liquid communication with at least a portion of said original semen sample.

It is another object of the present invention to provide the SSS as define above, wherein at least one of the following is held true:
  i) the total number of motile CSP separated into said second chamber is at least $4*10^6$ as examined with phase contrast or light microscopes, when said original semen sample is a NORMAL sample as defined by WHO 1999 Appendix IA clause 2.5;
  ii) the concentration of motile CSP separated into said second chamber is at least $4*10^6$ [cell/ml] as measured with phase contrast or light microscopes when said original semen sample is a NORMAL sample as defined by WHO 1999 Appendix IA clause 2.5;
  iii) the total number of progressive motile CSP separated into ⁵said second chamber is at least $2*10^6$ as measured with phase contrast or light microscopes, when said original semen sample is a NORMAL sample as defined by WHO 1999 Appendix IA clause 2.5;
  iv) the average percentage of CSP having normal morphology in said enriched sample is at least 32%, as measured with phase contrast or light microscopes when said original semen sample is a NORMAL sample as defined by WHO 1999 Appendix IA clause 2.5.

It is another object of the present invention to provide the SSS as define above, wherein at least one of the following is held true:
  i) the average % of motile sperm cells in said enriched sample in said second chamber is increased by an average of at least 210% relatively to the average % motile sperm cells in said original semen sample, as measured with phase contrast or light microscopes;

ii) the % of progressive motile CSP in said enriched sample in said second chamber is increased by an average of at least 290% relatively to the average % progressive motile CSP in said original semen sample, as measured with phase contrast or light microscopes;

iii) the % of CSP having normal morphology in said enriched sample in said second chamber is increased by an average of at least 260% relatively to the average % of CSP having normal morphology in said original semen sample, as measured with phase contrast or light microscopes.

It is another object of the present invention to provide the SSS as define above, wherein at least one of the following is held true:

a. the average % of motile sperm cells isolated into said enriched sample is multiplied by at least 2.0 relatively to the average % motile sperm cells in said original semen sample as measured with phase contrast or light microscopes;

b. the average % of progressive motile sperm cells isolated into said second chamber is multiplied by at least 1.4 relatively to the average % of progressive motile sperm cells in said original semen sample as measured with phase contrast or light microscopes;

c. the % of decrease said CSP having abnormal round cells morphology isolated into said second chamber is about 99% as measured with phase contrast or light microscopes.

It is another object of the present invention to provide the SSS as define above, wherein said isolated sperm cells are depleted of round non motile cells selected from group of round non sperm cells, immature sperm cells, dead sperm cells or any combination thereof.

It is another object of the present invention to provide the SSS as define above, wherein the average yield of separation is higher than 58%, especially about 62% relatively to said original semen sample before said separation.

It is another object of the present invention to provide the SSS as define above, wherein at least an average of at least 70% especially 84% of said isolated sperm cells are progressively motile.

It is another object of the present invention to provide the SSS as define above, wherein said SSS is further adapted to perform assays selected from a group consisting of: a sperm cells concentration assay, a semen pH assay, a leukocytes concentration threshold assay, a sperm cells motility assay, a sperm cells morphology assay, a semen volume assay, a viscosity assay and a turbidity assay.

It is another object of the present invention to provide the SSS as define above, wherein said assays is adapted to facilitate diagnosis of at least one sexually transmitted disease (STD) selected from a group consisting of: syphilis, gonorrhea, Candida, human papiloma virus (HPV), mycoplasma, ureaplasma, human immunodeficiency virus (HIV), Chlamydia, herpes simplex virus, Hepatitis B, Trichomonas and Hepatitis C.

It is another object of the present invention to provide the SSS as define above, wherein said SSS is sealed such that no contamination of the environment outside said cartridge is performed.

It is another object of the present invention to provide the SSS as define above, additionally comprising a reagent adapted to, upon contact with said original sperm sample, to yield a reaction and/or a colored compound indicating (i) existence; or, (ii) concentration of a component in said original or enriched sample; (iii) a result of said at least one assay.

It is another object of the present invention to provide the SSS as define above, wherein said reagent is selected from a group consisting of cell support medium, labeling compounds, markers, peptide, color-changeable pad or any combination thereof.

It is another object of the present invention to provide the SSS as define above, wherein said original sample is selected from a group consisting of: a semen sample, a vaginal secretion sample, a vaginal cell sample, a blood sample, a urine sample, a saliva sample, a lymph sample or any combination thereof.

It is another object of the present invention to provide the SSS as define above, wherein said SSS is made of substantially rigid materials or a substantially flexible materials or any combination thereof.

It is another object of the present invention to provide the SSS as define above, further comprising at least one sensor adapted to interface with said cartridge to facilitate said at least one assay.

It is another object of the present invention to provide the SSS as define above, further comprising a control adapted to perform at least one action selected from a group consisting of: (i) receive a reading from said at least one sensor, said sensor is in communication with said cartridge; (ii) analyze said reading; (iii) analysis readings received based upon said at least one of said assays; and (iv) output said analysis of said original sperm sample.

It is another object of the present invention to provide the SSS as define above, wherein said cell separation device is socketed in said incubation means for a pre-determined period of about 10 minutes to about 60 minutes.

It is another object of the present invention to provide the SSS as define above, wherein said incubation means are adapted to thermoregulate the temperature within said cell separation device to a temperature of about 30 Celsius degrees and about 39 Celsius degrees, more preferably about 35.5 Celsius degrees to about 37.5 Celsius degrees.

It is another object of the present invention to provide the SSS as define above, wherein said temperature is about 37 Celsius degrees.

It is another object of the present invention to provide the SSS as define above, wherein said cell separation device additionally comprising a cover; said cover comprises at least two orifices; said orifices are adapted to enable guided entry or aspiration of fluids aspiration means or actuators to either said first central chamber or said second chamber.

It is another object of the present invention to provide the SSS as define above, wherein said actuators are selected from a group consisting of needle, cannula, pipette, syringe any positive displacement system such as a peristaltic pump or any combination thereof.

It is another object of the present invention to provide the SSS as define above, wherein said cell separation device additionally comprising at least one orifice adapted to enable entry or aspiration of fluids aspiration means or actuators either to said first central chamber or said second chamber.

It is another object of the present invention to provide the SSS as define above, wherein said actuators are selected from a group consisting of needle, cannula, pipette, syringe any positive displacement system such as a peristaltic pump or any combination thereof.

It is another object of the present invention to provide the SSS as define above, wherein said SCP are collected from said second chamber manually or automatically.

It is another object of the present invention to provide the SSS as define above, further adapted to assess motility of sperm cells and/or isolate motile sperm within an enriched semen sample for assisting fertility or diagnose sperm cells.

It is another object of the present invention to provide the SSS as define above, further adapted to assess motility of sperm cells in said original or enriched semen sample, and/or isolate motile sperm of said original or enriched semen sample for fertility treatments selected from a group consisting of: intra uterine insemination (IUI), vaginal insemination, and in-vitro fertilization (IVF).

It is another object of the present invention to provide the SSS as define above, wherein said rim is configured with specific surface roughness or serration to facilitate required surface tension, surface energy, capillary forces capabilities for specific sample/reagent combination.

It is another object of the present invention to provide the SSS as define above, wherein said support medium is selected from a group consisting of Ringer's solution, Hartmann's solution, Saline Hyaluronic acid, Phosphor buffered saline (PBS) or any other sperm preparation or separation or washing medium adapted to facilitate said separation.

It is another object of the present invention to provide the SSS as define above, wherein said first central chamber of said SSS is adapted to contain an original semen sample having a volume measurement ranging from about 0.1 ml to about 10 ml.

It is another object of the present invention to provide the SSS as define above, wherein said SSS is adapted for diagnostics of male infertility.

It is another object of the present invention to provide the SSS as define above, wherein said SSS is disposable.

It is another object of the present invention to provide the SSS as define above, wherein said SSS is reusable and may be configured for multi-use.

It is another object of the present invention to provide a naturally based method for separating at least a portion of sperm cell populations (SCP) characterized by (i) motility in a range between about 5 µm/s to about 15 µm/s at 37°; (ii) slow progressive motility in a range between about 15 µm/s at 37° to about 25 µm/s at 37°; (iii) rapid progressive motility of at least 25 µm/s at 37° and 20 µm/s at 20°; (iv) at least 90% motile sperm cells, having an average of at least 32% normal morphology; or any combination thereof, within an original semen sample into an enriched SCP sample. The method comprises steps selected inter alia from:
  a. providing a cell separation device, comprising:
     i) at least one first chamber; said first chamber is bounded by a rim; wherein said rim is crenellated shaped; said first chamber is characterized by predetermined 3D shape and volume, V; and,
     ii) at least one second chamber in physical communication with said first chamber and said rim;
  b. configuring said second chamber with pre-determined 3D shape and volume, $V_1$, wherein said $V_1$ is substantially smaller than V;
  c. obtaining incubation means;
  d. socketing said cell separation device within said incubation means;
  e. depositing said original semen sample within said first chamber such that said original semen sample is kept below said rim;
  f. introducing a support medium into either said first chamber and/or said second chamber such that said support medium is in liquid communication with at least a portion of said original semen sample; thereby residing at least a portion of said SCP crossing through the crenellations in said crenellated shaped rim within said second chamber; and,
  g. separating said SCP from said original semen sample into said enriched sample;

wherein said step (b) of configuring said second chamber with predetermined 3D shape and performing said steps (d-g) while constantly and homogeneously thermoregulating the temperature within said cell separation device enables at least one of the following to be held true:
  i) efficacy of said SSS is at least 95%;
  ii) the total number of motile CSP separated into said second chamber is at least $4*10^6$ as examined with phase contrast or light microscopes, when said original semen sample is a NORMAL sample as defined by WHO 1999 Appendix IA clause 2.5 and comprises at least $5*10^6$ [motile CSP/ml];
  iii) the concentration of motile CSP separated into said second chamber is at least $4*10^6$ [cell/ml] as measured with phase contrast or light microscopes when the concentration of motile CSP in said original semen sample is at least $5*10^6$ [motile sperm cell/ml];
  iv) the total number of progressive motile CSP separated into said second chamber is at least $2*10^6$ as measured with phase contrast or light microscopes, when said original semen sample comprises at least $2.5*10^6$ [progressive motile CSP/ml];
  v) the average percentage of CSP having normal morphology in said enriched sample is at least 32% in as measured with phase contrast or microscopes when said original semen sample comprises an average of at least 18% CSP having normal morphology.

It is another object of the present invention to provide the method as define above, additionally comprising step of configuring said first chamber as dimpled-shaped.

It is another object of the present invention to provide the method as define above, additionally comprising step of configuring said $V_1$ to be equal to said V.

It is another object of the present invention to provide the method as define above, additionally comprising step of configuring said first chamber and said second in a co-axial manner such that said second chamber is peripheral and circumferentially encircles said first chamber.

It is another object of the present invention to provide the method as define above, additionally comprising step of configuring said first chamber and said second are in a side by side configuration.

It is another object of the present invention to provide the method as define above, additionally comprising step of configuring said first chamber and said second in a pile configuration It is another object of the present invention to provide the method as define above, additionally comprising step of configuring said pre-determined 3D shape of said first chamber with a circular cross sectional area having radius R.

It is another object of the present invention to provide the method as define above, additionally comprising step of configuring said pre-determined 3D shape of said second chamber with a circular cross sectional area having radius $R^1$.

It is another object of the present invention to provide the method as define above, additionally comprising step of configuring said pre-determined 3D shape of said first chamber with a cross sectional area having n ribs where n is an integer higher than or equals to 3, or any combination thereof.

It is another object of the present invention to provide the method as define above, additionally comprising step of configuring said pre-determined 3D shape of said second chamber with a cross sectional area having n ribs where n is an integer higher than or equals to 3, or any combination thereof.

It is another object of the present invention to provide the method as define above, additionally comprising step of enabling said SCP to cross through or above the crenellations in said crenellated shaped rim into said second chamber upon introduction of a support medium into either said first chamber and/or said second chamber such that said support medium is in liquid communication with at least a portion of said original semen sample.

It is another object of the present invention to provide the method as define above, wherein said steps (d-f) is performed while constantly and homogeneously thermoregulating the temperature within said cell separation device such that at least one of the following to be held true:
  i) the total number of motile CSP separated into said second chamber is at least $4*10^6$ as examined with phase contrast or light microscopes, when said original semen sample is a NORMAL sample as defined by WHO 1999 Appendix IA clause 2.5;
  ii) the concentration of motile CSP separated into said second chamber is at least $4*10^6$ [cell/ml] as measured with phase contrast or light microscopes when said original semen sample is a NORMAL sample as defined by WHO 1999 Appendix IA clause 2.5;
  iii) the total number of progressive motile CSP separated into 'said second chamber is at least $2*10^6$ as measured with phase contrast or light microscopes, when said original semen sample is a NORMAL sample as defined by WHO 1999 Appendix IA clause 2.5;
  iv) the average percentage of CSP having normal morphology in said enriched sample is at least 32%, as measured with phase contrast or light microscopes when said original semen sample is a NORMAL sample as defined by WHO 1999 Appendix IA clause 2.5.

It is another object of the present invention to provide the method as define above, wherein said steps (d-f) is performed while constantly and homogeneously thermoregulating the temperature within said cell separation device such that at least one of the following to be held true:
  i) the average % of motile sperm cells in said enriched sample in said second chamber is increased by an average of at least 210% relatively to the average % motile sperm cells in said original semen sample, as measured with phase contrast or light microscopes;
  ii) the % of progressive motile CSP in said enriched sample in said second chamber is increased by an average of at least 290% relatively to the average % progressive motile CSP in said original semen sample, as measured with phase contrast or light microscopes;
  iii) the % of CSP having normal morphology in said enriched sample in said second chamber is increased by an average of at least 260% relatively to the average % of CSP having normal morphology in said original semen sample, as measured with phase contrast or light microscopes.

It is another object of the present invention to provide the method as define above, wherein said steps (d-f) is performed while constantly and homogeneously thermoregulating the temperature within said cell separation device such that at least one of the following to be held true:
  a. the average % of motile sperm cells isolated into said enriched sample is multiplied by at least 2.0 relatively to the average % motile sperm cells in said original semen sample as measured with phase contrast or light microscopes;
  b. the average % of progressive motile sperm cells isolated into said second chamber is multiplied by at least 1.4 relatively to the average % of progressive motile sperm cells in said original semen sample as measured with phase contrast or light microscopes;
  c. the % of decrease said CSP having abnormal round cells morphology isolated into said second chamber is about 99% as measured with phase contrast or light microscopes.

It is another object of the present invention to provide the method as define above, wherein said step of separating said SCP from said original semen sample additionally comprising step of providing said separated SCP depleted of round non motile cells selected from group of round non sperm cells, immature sperm cells, dead sperm cells or any combination thereof.

It is another object of the present invention to provide the method as define above, wherein said step of separating said SCP from said original semen sample additionally comprising step of providing said separated SCP with an average of at least 70%, especially 84% progressively motile sperm cells.

It is another object of the present invention to provide the method as define above, wherein said step of separating said SCP from said original semen sample additionally comprising step of providing an average yield separation which is higher than 58%, especially 62% in average relatively to said original semen sample before said separation.

It is another object of the present invention to provide the method as define above, additionally comprising step of performing assays selected from a group consisting of: a sperm cells concentration assay, a semen pH assay, a leukocytes concentration threshold assay, a sperm cells motility assay, a sperm cells morphology assay, a semen volume assay, a viscosity assay and a turbidity assay.

It is another object of the present invention to provide the method as define above, additionally comprising step of facilitating diagnosis of at least one sexually transmitted disease (STD) selected from a group consisting of: syphilis, gonorrhea, Candida, human papiloma virus (HPV), mycoplasma, ureaplasma, human immunodeficiency virus (HIV), Chlamydia, herpes simplex virus, Hepatitis B, Trichomonas and Hepatitis C.

It is another object of the present invention to provide the method as define above, additionally comprising step of providing said SSS as a SSS sealed such that no contamination of the environment outside said cartridge is provided.

It is another object of the present invention to provide the method as define above, additionally comprising step of providing said SSS with a reagent adapted to, upon contact with said original or enriched sample, to yield a reaction and/or a colored compound indicating (i) existence; or, (ii) concentration of a component in said original or enriched sample; (iii) a result of said at least one assay.

It is another object of the present invention to provide the method as define above, additionally comprising step of selecting said reagent from a group consisting of cell support medium, labeling compounds, markers, peptide, color-changeable pad or any combination thereof.

It is another object of the present invention to provide the method as define above, additionally comprising step of selecting said original sample is selected from a group consisting of: a semen sample, a vaginal secretion sample, a vaginal cell sample, a blood sample, a urine sample, a saliva sample, a lymph sample or any combination thereof.

It is another object of the present invention to provide the method as define above, additionally comprising step of configuring said SSS to be made of substantially rigid materials or a substantially flexible materials or any combination thereof.

It is another object of the present invention to provide the method as define above, wherein said step of socketing said cell separation device within said incubation means is performed for a pre-determined period of about 10 minutes to about 60 minutes.

It is another object of the present invention to provide the method as define above, wherein said step of homogeneously thermoregulating the temperature within said cell separation device, thermoregulates the temperature to about 30 Celsius degrees and about 39 Celsius degrees, more preferably about 35.5 Celsius degrees to about 37.5 Celsius degrees.

It is another object of the present invention to provide the method as define above, wherein said step of providing said cell separation device provides the same with a cover; said cover comprises at least two openings said orifices are adapted to enable guided entry or aspiration of fluids aspiration means or actuators to either said first central chamber or said second chamber.

It is another object of the present invention to provide the method as define above, additionally comprising step of selecting said actuators from a group consisting of needle, cannula, pipette, syringe any positive displacement system such as a peristaltic pump or any combination thereof.

It is another object of the present invention to provide the method as define above, wherein said step of providing said cell separation device provides the same with one orifice adapted to enable entry or aspiration of fluids aspiration means or actuators either to said first central chamber or said second chamber.

It is another object of the present invention to provide the method as define above, additionally comprising step of selecting said actuators from a group consisting of needle, cannula, pipette, syringe any positive displacement system such as a peristaltic pump or any combination thereof.

It is another object of the present invention to provide the method as define above, additionally comprising step of collecting said SCP from said second chamber manually or automatically.

It is another object of the present invention to provide the method as define above, additionally comprising step of assessing motility of sperm cells and/or isolate motile sperm within an enriched semen sample for assisting fertility.

It is another object of the present invention to provide the method as define above, additionally comprising step of assessing motility of sperm cells in said enriched semen sample, and/or isolate motile sperm of said semen sample for fertility treatments selected from a group consisting of: intra uterine insemination (IUD, vaginal insemination, and in-vitro fertilization (IVF).

It is another object of the present invention to provide the method as define above, additionally comprising step of configuring said rim with specific surface roughness surface energy, capillary forces or serration to facilitate required surface tension capabilities for specific sample/reagent combination.

It is another object of the present invention to provide the method as define above, additionally comprising step of selecting said support medium from a group consisting of Ringer's solution, Hartmann's solution, Saline Hyaluronic acid, Phosphor buffered saline (PBS) or any other sperm preparation/separation/washing medium adapted to facilitate said separation.

It is another object of the present invention to provide the method as define above, wherein said first central chamber of said SSS is adapted to contain an original semen sample having a volume measurement ranging from about 0.1 ml to about 10 ml.

It is another object of the present invention to provide the method as define above, wherein said SSS is adapted for diagnostics of male infertility.

It is still object of the present invention to provide the method as define above, additionally comprising step of configuring said SSS as disposable.

It is lastly an object of the present invention to provide the method as define above, additionally comprising step of configuring said SSS for multi-use.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIG. 5A shows a schematic illustration of a semen sample container 150;

FIGS. 5B-5F illustrate two additional embodiments of the present invention;

DETAILED DESCRIPTION OF THE INVENTION

Figure 1A:
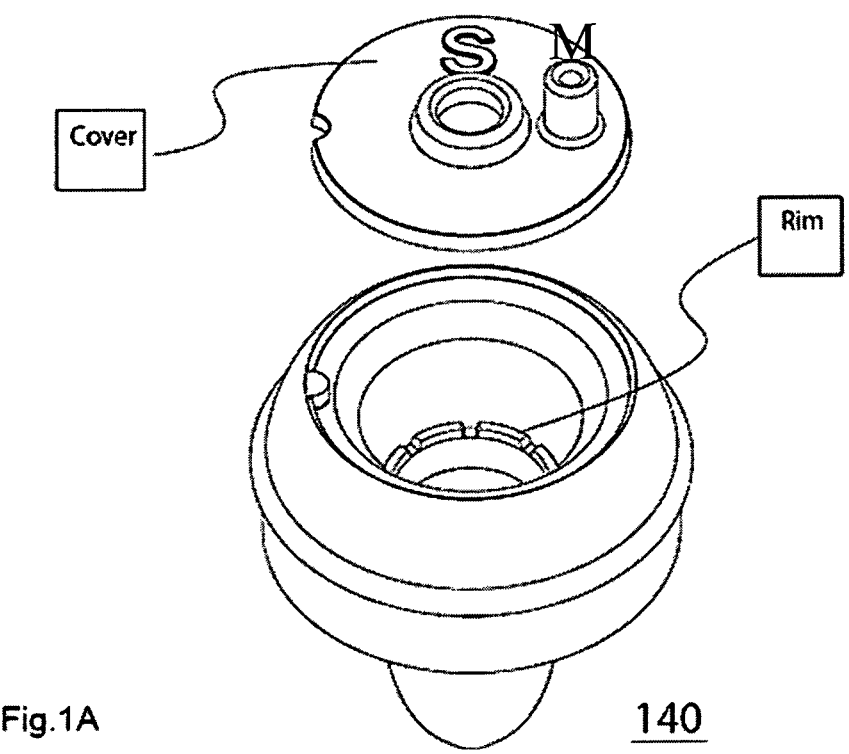
FIG. 1A shows an exploded view of a sperm separation device 140.

The present invention provides a sperm separation/preparation system designed to be used at Doctor's clinic, operations, laboratory or for home use. The system enables sperm preparation and enrichment procedures by means of motile sperm cell separation. The procedure using the sperm separation system enables sperm separation in a natural way with minimal external handling.

The system of the present invention enables the best spermatozoa (progressively motile and morphology wise) to migrate from the original semen sample to the sperm support medium, in a very natural way without mechanical handling.

The immotile and/or dead sperm cells, round cells and debris stay in the original semen. The harvested sperm cells population is suitable for insemination or for in vitro fertilization.

Progressively motile and normal morphology sperm cells are the prerequisite for fertilization and embryo development. However, more factors contribute for successful fertilization, hence the separating/preparation procedure is not a guarantee for the ovum fertilization occurrence and for further embryo normal development.

The key benefits of the system of the present invention are as follows:

Quick and simple to operate

The procedure requires neither prior training nor qualification and therefore can be performed by doctors and healthcare professionals No need of laboratory equipment and no mechanical handling The sperm separation procedure can be conjugated to a following insemination or in vitro fertilization Separation of the progressively motile sperm cells with high percentage of normal morphology Eliminates round non sperm cells Enhanced accessibility of fertility treatment to patients The procedure is natural with minimal handling Can be performed with all approved sperm culture mediums as commonly practiced. costs The present invention provides a naturally based Sperm Separation System (SSS) for separation of at least a portion of sperm cell populations (SCP) characterized by (i) motility in a range between about 5 μm/s to about 15 μm/s at 37°; (ii) slow progressive motility in a range between about 15 μm/s at 37° to about 25 μm/s at 37°; (iii) rapid progressive motility of at least 25 μm/s at 37° and 20 μm/s at 20°; (iv) at least 90% motile sperm cells, having an average of at least 32% normal morphology; or any combination thereof, within an original semen sample, such that an enriched SCP sample is obtained; said SSS comprising:

c. a sperm separation device, comprising:
    i) at least one first chamber adapted to contain at least a portion of said original semen sample; said first chamber is characterized by pre-determined 3D shape and volume, V; said first chamber is bounded by a rim such that said original semen sample is kept below said rim; wherein said rim is crenellated shaped; and,
    ii) at least one second chamber in physical communication with said first chamber and said rim; said second chamber is characterized by pre-determined 3D shape and volume, $V_1$, wherein said $V_1$ is substantially smaller than V;
    said second chamber is adapted to reside said enriched SCP sample; said enriched SCP sample comprising at least a portion of said SCP crossing through the crenellations in said crenellated shaped rim such that said separation of said SCP from said original semen sample is obtained and said enriched SCP sample is provided;

d. incubation means, adapted to socket at least one of said cell separation device and to homogeneously thermoregulate the temperature within the same;

wherein said pre-determined 3D shape of said first and second chambers and said crenellations in said rim enables at least one of the following is held true:
  i) efficacy of said SSS is at least 95%;
  ii) the total number of motile CSP separated into said second chamber is at least $4*10^6$ as examined with phase contrast or light microscopes, when said original semen sample is a NORMAL sample as defined by WHO 1999 Appendix IA clause 2.5 and comprises at least $5*10^6$ [motile CSP/ml];
  iii) the concentration of motile CSP separated into said second chamber is at least $4*10^6$ [cell/ml] as measured with phase contrast or light microscopes when the concentration of motile CSP in said original semen sample is at least $5*10^6$ [motile sperm cell/ml];
  iv) the total number of progressive motile CSP separated into said second chamber is at least $2*10^6$ as measured with phase contrast or light microscopes, when said original semen sample comprises at least $2.5*10^6$ [progressive motile CSP/ml];
  v) the average percentage of CSP having normal morphology in said enriched sample is at least 32% in as measured with phase contrast or microscopes when said original semen sample comprises an average of at least 18% CSP having normal morphology.

As described above and as will be disclosed hereinafter the 3D configuration of the two chambers will make sure that the motile CSP separated into said second chamber are not diluted (since the volume of the second chamber is substantially smaller than the volume of the first chamber). Dilution of the CSP is a major disadvantage of some of the commonly used separators.

Furthermore, as described above and as will be disclosed hereinafter the 3D configuration of the two chambers will make sure that the motile CSP separated into said second chamber are not diluted (since the volume of the second chamber, if not smaller than, it is equivalent to is the volume of the first chamber).

The term "about" refers hereinafter to a range of 25% below or above the referred value.

The term "efficacy" refers hereinafter to the efficacy as determined in example 2.

The term "NORMAL sample" refers hereinafter to a sperm sample characterized by values at least equal to the reference values as defined by WHO 1999 Appendix IA clause 2.5 which reads as follows:

| Reference Values | |
| --- | --- |
| Volume | 2.0 ml or more |
| pH | 7.2 or more |
| Sperm concentration | $20 * 10^6$ [spermatozoa/ml] or more |
| Total sperm number | $40 * 10^6$ spermatozoa per ejaculate or more |
| Motility | 50% or more motile or 25% or more with progressive motility within 60 minutes of ejaculation |
| vitality | 50% or more live. i.e., excluding dye. |
| White blood cells | Fewer than $1 * 10^6$/ml |
| Immunobead test | Fewer than 50% motile spermatozoa with beads bound |
| MAR test | Fewer than 50% motile spermatozoa with adherent particles |

| | |
|---|---|
| Reference Values | |
| Morphology | Data from assisted reproductive technology suggest that as sperm morphology falls below 15% normal forms using the method and definitions described in the WHO, the fertilization rate in vitro decreases. |

The term "phase contrast" refers hereinafter to any technique in which small phase shifts in the light passing through a transparent specimen are converted into amplitude or contrast changes in the image.

As used herein the term "naturally based" refers to the natural way by which the sperm cells are separated. In other words, the sperm cells of the present invention are separated without any external (mechanical or human) interference (e.g., centrifuge). The motile sperm cells within a semen sample are separated by the sperm separation system of the present invention with practically no external attention and interference, including mechanical or human handling such as centrifugation, washes of the sample, filtration or any other external handling, and with no need of additional laboratory equipment.

As used herein the term "Seaforia™" refers hereinafter as the Sperm Separation System (SSS).

As used herein the term "incubation means" refers hereinafter to any heating device adapted to homogeneously thermoregulate the temperature within the cell separation device.

As used herein the term "ART" refers hereinafter as the acronym for Artificial Reproductive Technologies.

As used herein the term "IFU" refers hereinafter as the acronym for Instruction For Use.

As used herein the term "IUI" refers hereinafter as the acronym for Intra Uterine Insemination.

As used herein the term "IVF" refers hereinafter as the acronym for In Vitro Fertilization.

As used herein the term "USB" refers hereinafter as the acronym for Universal Serial Bus.

As used herein the term "(S)" refers hereinafter as the acronym for Semen sample insertion orifice.

As used herein the term "(M)" refers hereinafter as the acronym for sperm support medium insertion, and drawing the medium and harvested cells orifice.

As used herein the term "(IEC)" refers hereinafter as the acronym for International Electro technical Commission.

As used herein the term "(ISO)" refers hereinafter as the acronym for International Organization for Standardization.

As used herein the term "(AAMI)" refers hereinafter as the acronym for Association of Advancement of Medical Instrumentation.

As used herein the term "(ANSI)" refers hereinafter as the acronym for American National Standards Institute.

As used herein the term "(BS)" refers hereinafter as the acronym for British Standards.

As used herein the term "side by side configuration" refers hereinafter to the configuration in which the first chamber and the second chamber are not co-axial. i.e., the configuration as illustrated in FIG. 5C, in which each couple of first and second chambers are positions adjacently to a second couple.

As used herein the term "pile" refers hereinafter to a configuration in which the first and second chambers are place one on top of other.

Figure 5D:
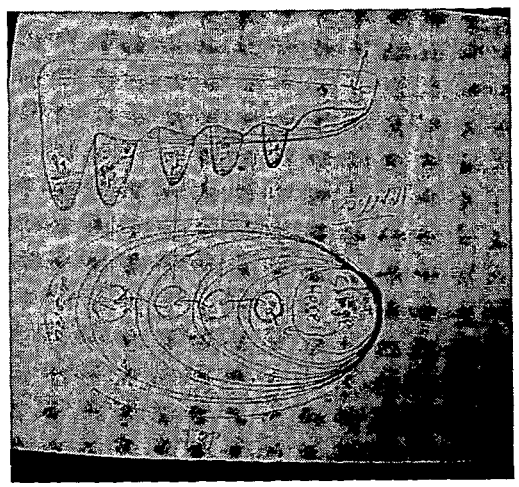

In FIG. 5D another view of the same embodiment is illustrated.

Such a separator can be used to separate different population within a single sample (e.g., motile sperm cell, slow progressive motile sperm cells, rapid progressive motile perm cells et cetera).

It is a main aspect of the invention that the sperm separation system is adapted to isolate an elite quality segment of motile spermatozoa population for further use in fertility treatments such as IUI or IVF.

It is indicated that the sperm separation by the system of the present invention can be performed with all approved sperm mediums as commonly practiced.

The biologic sample may be, for example, a semen sample, a vaginal secretion sample, a biologic cells sample, cervical mucus, or any other sample of biologic matter collected from a human or any other animal.

One embodiment of the sperm separation system of the present invention is a processing/assay device, alternatively heating device that may be used to hold said sperm separation device. said heating device (i.e., incubation means) further used to maintain temperature required for any of selected assay, further may be include computer interface for operation, management of assay, management of data.

After use, the cartridge, alternatively sperm separation device or separator may be removed from the processing/assay device, alternatively heating device and discarded.

Alternatively, the sperm separation device or separator may be stored (such as in cooled or cryogenic storage), along with its contents, for future testing, analysis and/or treatment of the sample.

The device, alternatively separator may be configured such that only a part of it, containing portion of sample or the treated sample, is removed and stored for further testing, analysis and/or treatment.

The incubation means, alternatively heating device may be relatively easy to operate and its operation may require no special laboratory training, so that a nurse, a physician, or any other caregiver may operates it in what is often referred to as a "point of care"—a clinic, a medical institution or the like. Furthermore, the processing/assay device, alternatively heating device may still be operated at the field, such as with portable apparatuses, tools or disposable units, at home or in a laboratory.

Another aspect of some embodiments relates to incubation means, alternatively heating device adapted to receive a receptacle, such as a condom or any sample collection cup, namely the sperm separation device of the present invention, containing a reproductive system sample such as semen, a vaginal secretion, any type of cells found in the vagina, cervical mucus and/or the like.

In case the sample is semen, the processing/assay device, alternatively heating device may be used for assessing, using at least one assay, one or more parameters pertaining to the semen sample and/or for treating the sperm cells sample.

The incubation means, alternatively heating device may include an extraction mechanism for extracting the semen sample from the receptacle and for transporting the semen sample towards one or more assay locations where the semen sample is assessed.

Optionally, the user is the reproductive system sample provider, and, accordingly, the incubation means, alternatively heating device may be adapted for use by a non-medically trained person. The incubation means, alternatively heating device may be therefore offered to consumers either as a prescription medical device or as an over-the-counter (OTC) non-prescription device.

The sperm separation device, alternatively separator may be essentially rigid or essentially flexible, and may include an actuator interface for interfacing with an external means of pressure vacuum creation, so as to transport the biologic sample towards one or more assay and/or treatment ports.

A further aspect of some embodiments relates to a cells separation system. When used with sperm cells, it is adapted to assess motility of sperm cells and/or to isolate motile sperm cells of the semen sample for IUI, vaginal insemination, or IVF purposes. The cells separation system may also be used for separating other types of motile cells from immotile cells.

The sperm separation device may include a first chamber adapted to contain at least a portion of a semen sample, and a second chamber adapted to receive motile cells upon introduction of a separation-enabling agent alternatively support medium, into the first chamber.

According to certain embodiments of the invention, the separation-enabling agent alternatively support medium, may be a fluid in gas or liquid form, Solid with required wet ability characteristics, a gel and/or any other suitable substance. After the separation, the first chamber may include an enriched population of immotile cells while the second chamber may include an enriched population of motile cells.

The sperm separation device is optionally enclosed within a cartridge, which is, in turn, adapted for insertion into the incubation means, alternatively heating device.

Alternatively, the sperm separation device may be used as a standalone device, separated from a cartridge, and incubation means, alternatively heating device detailed above.

This invention of sperm separation system is intended for sperm separation procedure, in which culture medium is layered over liquefied semen sample and during a subsequent incubation of 10 to 60 minutes, preferably 30 minutes the motile sperm cells migrate from the lower semen layer into the upper culture medium.

It is possible to aspirate top layer of sperm enriched medium from first chamber with height limited actuator, or side aspirating actuator.

Radius $R_1$, depth $D_1$ and volume, $V_1$, are dimensioned for negligible fluid remains within second chamber.

It should be pointed out that in a specific case where the gravity of medium is higher than the semen sample, reversed population is anticipated. In such a case, it is possible to aspirate sperm enriched medium from the bottom of the first chamber with height limited actuator, or side aspirating actuator.

It is a further embodiment of the present invention to provide the Sperm Separation device as a disposable Kit.

The Disposable Sperm Separation Kit is a very compact and simple for use kit for sperm preparation, aimed to separate motile sperm cells from a semen sample.

All items needed for one single procedure are included within the Disposable Kit with no need of any additional laboratory equipment, requiring minor attention and handling.

The Principle of Operation of the aforementioned kit:

Sperm Separation Disposable Kit enables the best spermatozoa (progressively motile and morphology wise) to migrate from the original semen sample to the sperm support medium, in a very natural way without mechanical handling.

The immotile and/or dead sperm cells, round cells and debris stay in the original semen. The harvested sperm cells population is suitable for insemination or for in vitro fertilization.

Progressively motile and normal morphology sperm cells are the prerequisite for fertilization and embryo development.

The sperm separation system of the present invention turns the clinic into a "one stop shop" for:
1) Diagnostics 2) Treatment of male infertility.

Thus, according to a further main aspect, the present invention provides a diagnostic system:

The benefits of the sperm separation/diagnostic system:
1. the system is located (a) near the patient at point of care (POC) or, (b) at doctor's clinics;
2. the system provides an OTC (Over The Counter) diagnostic system at home;
3. the diagnostic system can facilitate infertility diagnostic screening and decrease frustration, anxiety and uncertainty
4. the sperm separation system provides an automated multi parameter assay
5. the analysis is performed within a controlled and sealed environment such that no contamination of the environment is conducted.
6. Optical imaging technology Optical imaging and algorithm for numeric diagnostic results are based on:
Motile sperm cells concentration
Semen volume
Early semen screening diagnostic gives:
valuable information assisting the doctor in deciding upon further investigation or treatment
shorter time to treatment
ability to ease the psychological stress and reduce anxiety prior to the 12 month timeline
control: allowing couples to determine decisions about fertility planning
Couples within the initial stage (12 months) of conceiving efforts, as an initial fertility diagnostic screening
Couples going through fertility treatments (IVF, IUI)
Infertile couples seeking a second opinion
Single men in the fertile stage, no children need for rapid results, faster diagnostic benefits, better patient care by improving the time to treatment (TAT)
Sperm cells concentration
Motile sperm cells concentration
Semen volume
Semen pH
Leukocytes concentration
Reference is now made to the Figs:

The Sperm separation device 140 may be adapted to assess motility of sperm cells or any other cells of the biologic sample. Additionally or alternatively, sperm separation device 140 may be adapted to isolate motile sperm cells of the semen sample for IUI, vaginal insemination, and/or IVF purposes.

Sperm separation device 140 may be based upon the principle that motile cells (such as, for example, sperm cells) have swimming abilities, whereas immotile cells lack these abilities, at least to some extent. Therefore, sperm separation device 140 is constructed such that motile cells move, essentially using their own swimming capabilities, to a different location, while sediment of immotile cells is left behind.

Figure 1B:
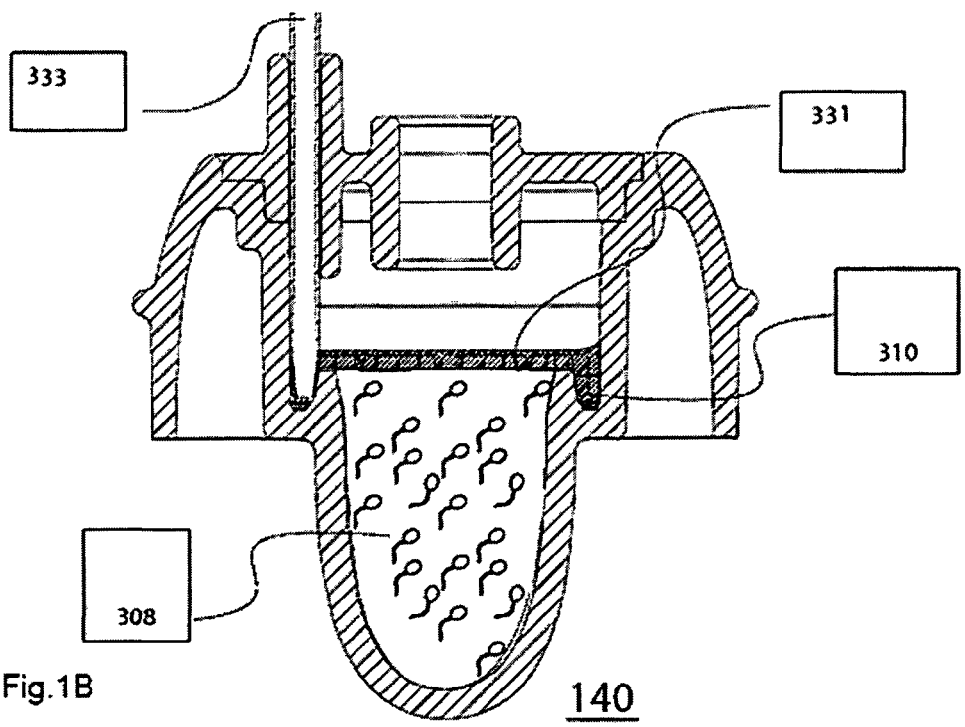
FIG. 1B shows a perspective view of a sperm separation device 140.
Figure 1C:
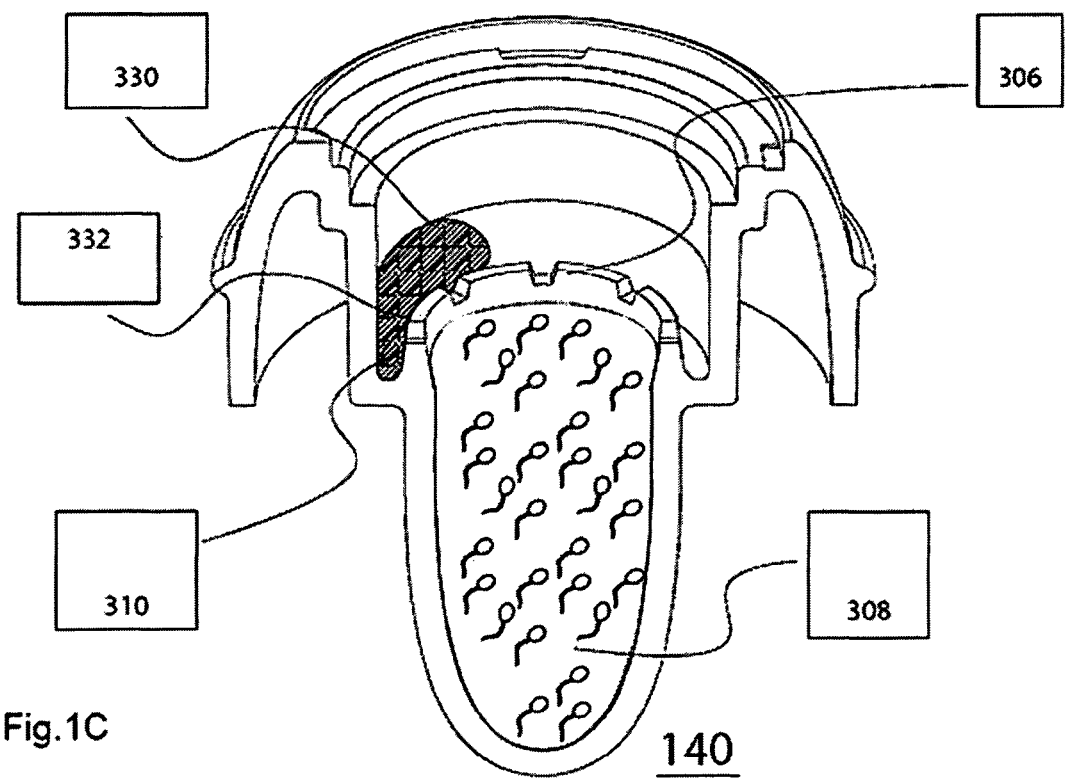
FIG. 1C shows a perspective view of the rim 306 within the sperm separation device 140.

Reference is made to FIG. 1A, 1B, 1C, in which sperm separation device 140 in more detail. The device may include cover 334, which is used to guide actuators (Not shown) to position. biologic sample (such as semen) 308 is inserted via central opening marked S, and separation-enabling agent alternatively support medium, 310, may be inserted via peripheral opening marked M. Harvested assay is removed from sperm separation device 140, via M opening.

Of cores, M opening may be in center of cover, and S in periphery.

The insertion and extraction of the sample or the separation agent is performed via a cannula, needle, syringe or any other actuator (333).

Inserted needle or cannula, in FIG. 1B, is via peripheral opening, showing no interface with sample 308. Separation-enabling agent alternatively support medium, 310, is inserted via said cannula, and is in overplayed on sample 308, to create fluid interface, 331 between 308 and 310.

Figure 3A:
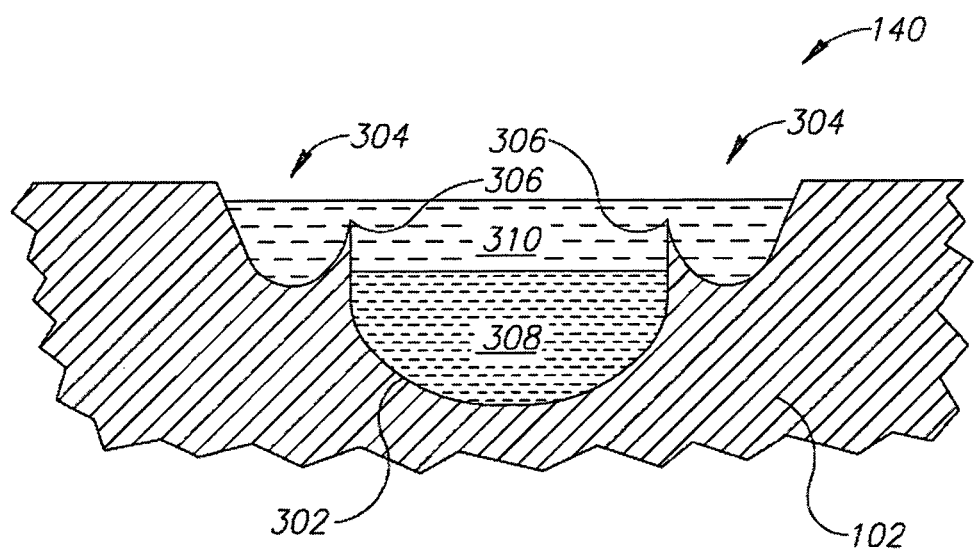
FIG. 3A shows a cross-sectional schematic view of a sperm separation device.
Figure 3B:
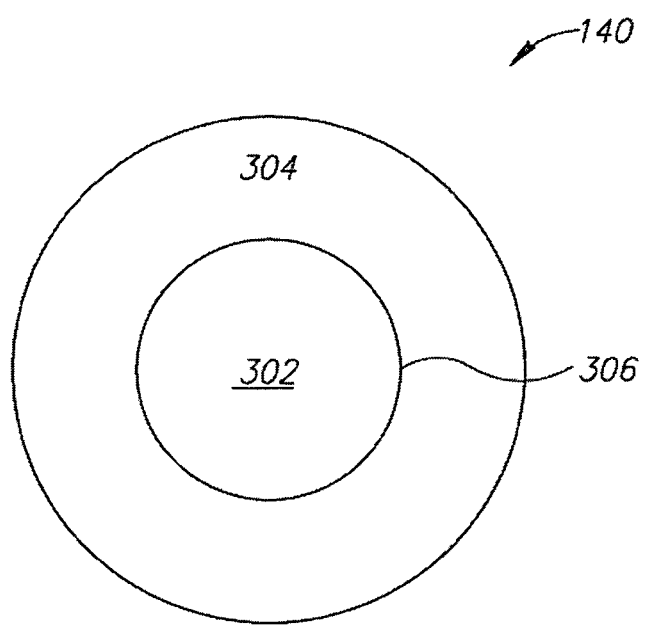
FIG. 3B shows a top schematic view of a sperm separation device.

FIG. 1C, and FIGS. 3A, 3B, describe the behavior of separation-enabling agent alternatively support medium, 310, when inserted to peripheral chamber 304. When inserted, the fluid 310, starts to flow between the peripheral chamber 304 and central chamber 302, separated by a crenellated shaped rim 306.

The separation-enabling agent, alternatively support medium, 310, flows in peripheral chamber.

The surface tension of separation-enabling agent alternatively support medium, 310, keeps fluid in peripheral chamber, which is dimensioned with surface roughness and crenellations, smaller then the breaking force required to brake surface tension of separation-enabling agent alternatively support medium, 310, hence the separation-enabling agent alternatively support medium, 310, continue to flow and fill the periphery chamber 304.

As more separation-enabling agent alternatively support medium, 310 in introduced, the separation-enabling agent alternatively support medium 310 meniscus is building up, until surface tension is weaker them the meniscus hydraulic build up, and it breaks. The separation-enabling agent alternatively support medium, 310 is flowing from periphery 304 onto the sample 308 inside central chamber 302

Figure 1D:
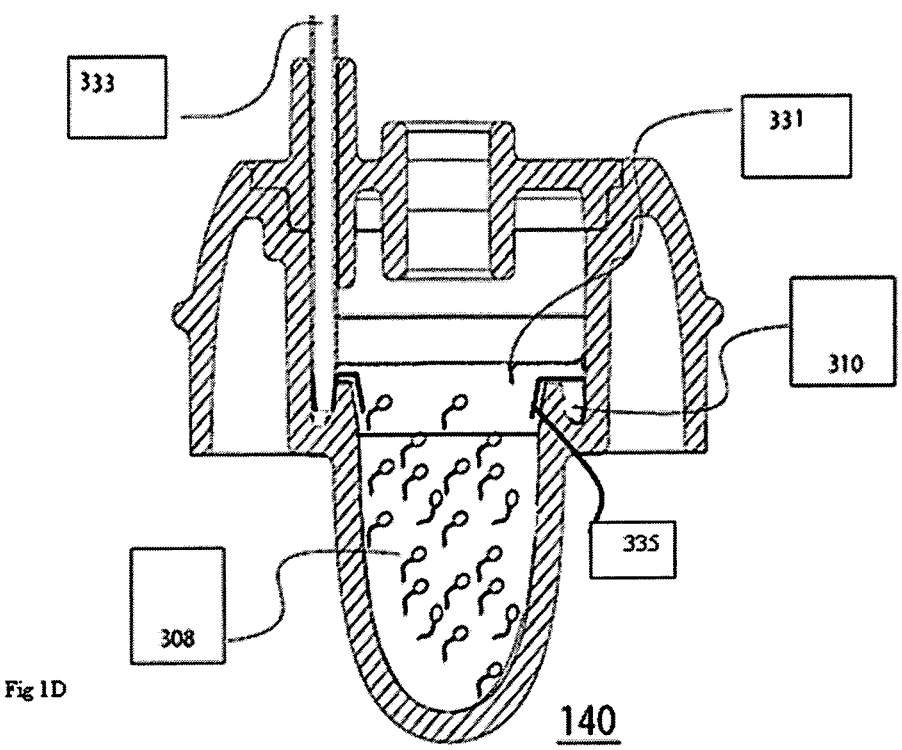
FIGS. 1D-1E illustrates another embodiment of the present invention.
Figure 1E:
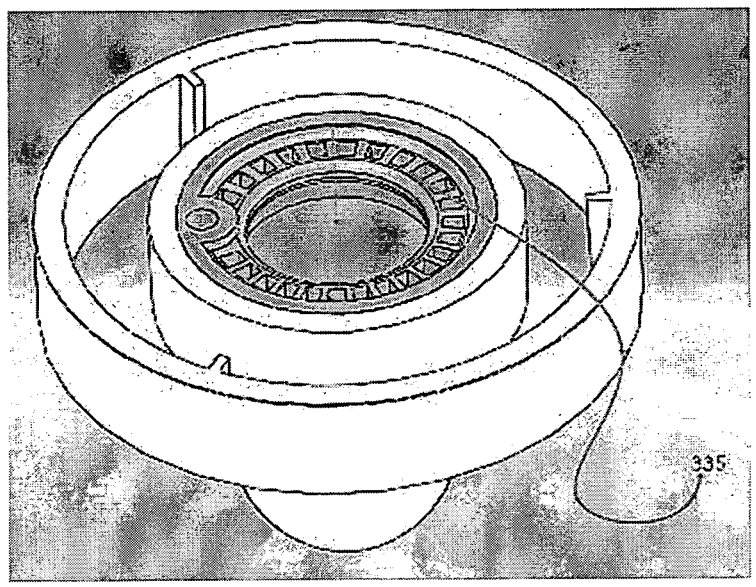

According to another embodiment of the present invention a lip 335 is provided. Reference is now made to FIGS. 1D-1E. In order to facilitate the flow of the separation-enabling agent alternatively support medium, 310 a lip 335 (see FIG. 1D) is mounted adjacent to rim 306. The distance between rim 306 and lip 335 is dimensioned in such a manner, that when separation-enabling agent (or alternatively support medium) 310 is introduced, the separation-enabling agent (or alternatively support medium) 310 meniscus does not break until separation-enabling agent (or alternatively support medium) 310 flows within periphery 304.

When all periphery is full, the hydraulic head, together with adhesive/cohesive forces, allow the separation-enabling agent (or alternatively support medium), 310 to flow from periphery 304 onto the sample 308 inside the central chamber 302.

Lip 335 may be shaped as a flat disk, a bevel disk, perforated disk or mesh, either concentric, unidirectional or radial projected. Mesh size in a range of 5×5 micron sq up to 3000×3000 micron void size.

FIG. 1E illustrates the same as FIG. 1D in which a top view is given, Reference is now made to FIGS. 3A and 3B, which show sperm separation device 140 in more detail. FIG. 3A is a cross-sectional view and FIG. 3B is a top view.

Sperm separation device 140 may include two chambers: a central chamber 302 shaped as a dimple in main body 102, and a peripheral chamber 304 shaped as a shallower, circumferential depression around the central chamber.

In order to operate sperm separation device 140, a biologic sample (such as semen) 308 is deposited inside central chamber 302, while keeping the sample's level below a rim 306. Rim 306, may be dimensioned and designed with specific surface roughness or serration in order to facilitate required surface tension capabilities for specific sample/reagent combination.

As one of the important characteristics of a liquid material is its ability to freely wet the surface of the object being inspected. At the liquid-solid surface interface, if the molecules of the liquid have a stronger attraction to the molecules of the solid surface than to each other (the adhesive forces are stronger than the cohesive forces), wetting of the surface occurs. Alternately, if the liquid molecules are more strongly attracted to each other than the molecules of the solid surface (the cohesive forces are stronger than the adhesive forces), the liquid beads-up and does not wet the surface of the part.

One way to quantify a liquid's surface wetting characteristics is to measure the contact angle of a drop of liquid placed on the surface of an object. The contact angle is the angle formed by the solid/liquid interface and the liquid/vapor interface measured from the side of the liquid. Liquids wet surfaces when the contact angle is less than 90 degrees. For a fluid material to be effective, the contact angle should be as small as possible. In fact, the contact angle for full wetting most is very close to zero degrees.

Wetting ability of a liquid is a function of the surface energies of the solid-gas interface, the liquid-gas interface, and the solid-liquid interface. The surface energy across an interface or the surface tension at the interface is a measure of the energy required to form a unit area of new surface at the interface. The intermolecular bonds or cohesive forces between the molecules of a liquid cause surface tension. When the liquid encounters another substance, there is usually an attraction between the two materials. The adhesive forces between the liquid and the second substance will compete against the cohesive forces of the liquid. Liquids with weak cohesive bonds and a strong attraction to another material (or the desire to create adhesive bonds) will tend to spread over the material. Liquids with strong cohesive bonds and weaker adhesive forces will tend to bead-up or form a droplet when in contact with another material.

In liquid penetrating testing, there are usually three surface interfaces involved, the solid-gas interface, the liquid-gas interface, and the solid-liquid interface. For a liquid to spread over the surface of a part, two conditions must be met. First, the surface energy of the solid-gas interface must be greater than the combined surface energies of the liquid-gas and the solid-liquid interfaces. Second, the surface energy of the solid-gas interface must exceed the surface energy of the solid-liquid interface.

Fluid wetting characteristics are also largely responsible for its ability to fill a void. fluid materials are often pulled into surface defects or roughness by capillary action. The capillary force driving the fluid into a crack is a function of the surface tension of the liquid-gas interface, the contact angle, and the size of the opening. The driving force for the capillary action can be expressed as the following formula:

$$\text{Force} = 2\pi r \sigma_{LG} \cos \theta$$

Where:

r=radius of the opening (2 pr is the line of contact between the liquid and the solid tubular surface); $\sigma_{LG}$=liquid-gas surface tension; θ=contact angle.

Since pressure is the force over a given area, it can be written that the pressure developed, called the capillary pressure, is $$\text{Capillary Pressure} = (2\sigma_{LG} \cos \theta)/r$$

The above equations are for a cylindrical defect but the relationships of the variables are the same for a flow with a noncircular cross section. Capillary pressure equations only apply when there is simultaneous contact of the fluid along the entire length of the crack opening and a liquid front forms that is an equidistant from the surface. A liquid surface could take-on a complex shape as a consequence of the various deviations from flat parallel walls that an actual crack could have. In this case, the expression for pressure is $$\text{Capillary Pressure}=2(\sigma_{SG}-\sigma s_{SL})/r=2\Sigma/r$$

Where:

$\sigma_{SG}$=the surface energy at the solid-gas interface; $\sigma_{SL}$=the surface energy at the solid-liquid interface; r=the radius of the opening; $\Sigma$=the adhesion tension ($\sigma_{SG}-\sigma_{SL}$);

Therefore, at times, it is the adhesion tension that is primarily responsible for a fluid movement into a flaw and not the surface energy of the liquid-gas interface. Adhesion tension is the force acting on a unit length of the wetting line from the direction of the solid. The wetting performance of the fluid is degraded when adhesion tension is the primary driving force.

However, other factors are also acting in the comparison. These methods include the density, viscosity, and volatility of the liquid, which do not enter into the capillarity equations, but may have an effect on the inspection as will be discussed.

Said rim 306 is crenellated shaped such that semen cells are crossing through the crenellations in said crenellated shaped rim 306 into the peripheral chamber 304. A separation-enabling agent alternatively support medium, 310, such as a Ringer's solution, Hartmann's solution, Saline, Hyaluronic acid, Phosphor buffered saline (PBS), and/or any other sperm washing medium of HTF such as available from Irvine scientific, Santa Ana, Calif. USA, or sperm selection medium is then introduced into central chamber 302 and/or into peripheral chamber 304, such that the separation-enabling agent alternatively support medium, covers both the entirety of central chamber 302 and at least a portion of peripheral chamber 304.

Then, semen sample 308 and separation-enabling agent alternatively support medium, 310 may be left for a period of optionally 10 to 60 minutes in a temperature of optionally 30-39 Celsius degrees, preferably at 35.5-37.5 Celsius degrees, most preferably at 36.8 Celsius degrees in incubation means (i.e., heating device) allowing motile cells to swim up through separation-enabling agent alternatively support medium, 310 and at least partially into peripheral chamber 304. After the specified period, the motile cells may be collected, manually or automatically, from peripheral chamber 304.

It should be emphasized that the central chamber 302 is characterized by pre-determined radius R, depth D and volume, V. Furthermore, the peripheral chamber 304 is characterized by pre-determined 3D dimensions selected from radius $R_1$, depth $D_1$ and volume, $V_1$; the dimensions of the two chamber are provided such that said $D_1$ is substantially smaller than D; $V_1$ is substantially smaller than V. In such a configuration, the isolated sperm sample will not be diluted when crossing into the second chamber.

Furthermore, according to another embodiment of the present invention, volume, $V_1$ equals to volume, V such that, again, the isolated sperm sample will not be diluted when crossing into the second chamber.

Figure 5E:
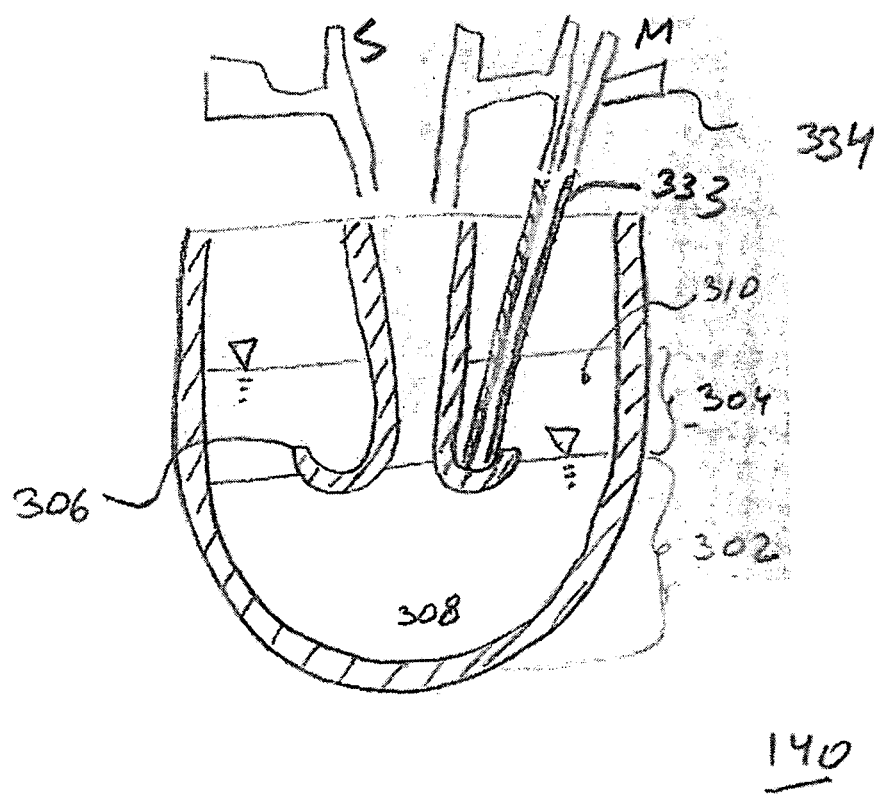
Figure 5F:
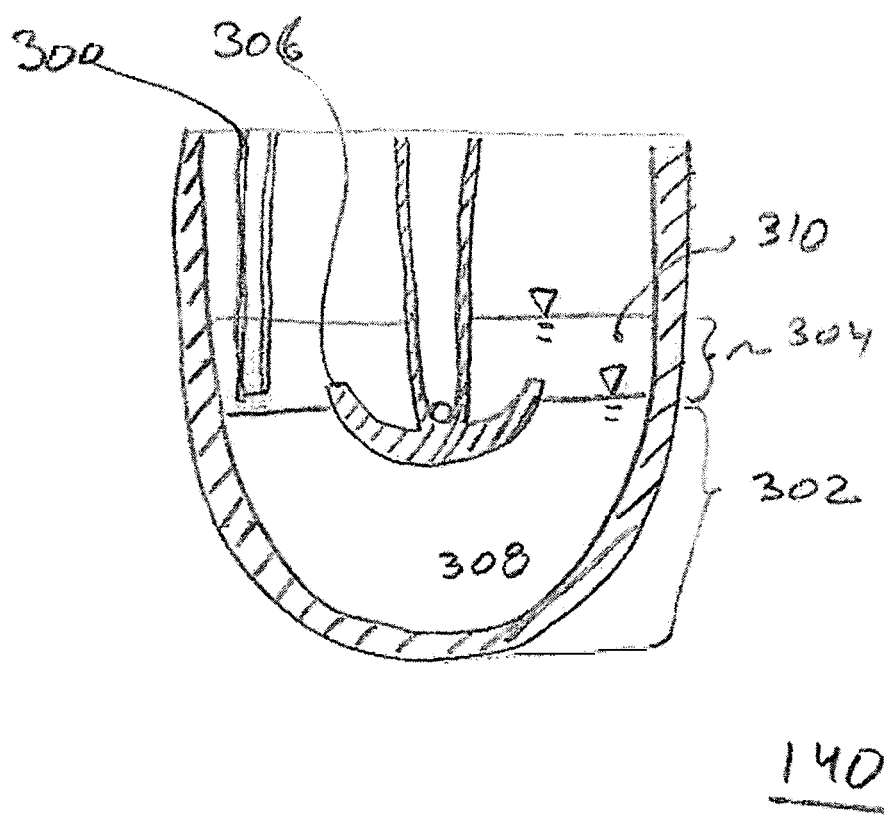

It should be further emphasized, as will be demonstrated in FIG. 5C, that the second chamber may be positioned in a side by side manner, i.e., the second chamber is not peripheral and circumferentially encircles said first chamber.

according to another embodiment, as will be demonstrated in FIG. 5E-5F, that the second chamber may be positioned in a pile configuration, i.e., one on top of the other.

It should be yet further emphasized that the predetermined 3D dimensions of the first and/or second chamber is not limited to circular and can have any cross sectional area having n ribs, where n is an integer greater than or equals to 3 (e.g. when n=3, the cross sectional area is a triangle; when n=4, the cross sectional area is a rectangular; when n=5, the cross sectional area is a pentagon et cetera).

It should be pointed out that the thermoregulation of the procedure is provided by incubation mean (i.e., the heating means) 200. The incubation means are provided as part of the sperm separation system SSS and are adapted to socket at least one of said sperm separation device 140 and to homogeneously thermoregulate the temperature within the same. The incubation means are illustrated in FIGS. 2C-S as numerical reference 200.

Sperm separation device 140 may also be operated inversely—a sample may be deposited in peripheral chamber 304 keeping its level below rim 306; a separation-enabling agent alternatively support medium, may be introduced into central chamber 302 while overflowing rim 306 onto the peripheral chamber; and the components may be left to allow motile cells to swim up from the peripheral chamber into the central chamber.

Generally, a sperm separation device such as system 140 or any other system may be constructed according to the principle that a first chamber is adapted to contain a semen sample, and a second chamber is adapted to receive motile cells upon introduction of a separation-enabling agent alternatively support medium, into the first chamber. In the examples given above, respectively, each of central chamber 302 and peripheral chamber 304 may be the first or the second chamber.

Sperm separation device 140 may be used to assess motility of sperm cells of the semen sample, and/or to isolate motile sperm cells of the semen sample for intra uterine insemination (WI), vaginal insemination and/or in-vitro fertilization (IVF) purposes. Reference is now made to FIG. 5a showing a schematic illustration of an opaque semen sample container 150. The sample container is developed in order to collect and deliver semen sample from the user to the laboratory or the Clinic. The sample container has the ability to measure the volume of the semen so the procedure performer would be able to make decisions regarding the semen volume (to make the procedure or not . . . to decide which separators volume to use est . . . ).

Additionally—since many psychological and physical aspects regarding the delivering of a semen sample are involved, the sample container is designed to deal with some more of those aspects:
  1. Temperature shock
  2. Exposure to bright light
  3. The ease of use
  4. The general look of the sample cup
  5. External cover to clock the content;

One of the main advantages of the semen sample container 150 is the fact that the same is opaque, hence several physiological aspect of the user is dealt with.

According to one embodiment of the invention, the sperm cells container comprises a conic shape tube 410 for collecting and storing the semen sample until used by the sperm separation system. The conic shaped container enables holding the semen sample within a small volume, allowing high recovery of the sperm cells loaded on the sperm separation system.

Reference is now made to FIGS. 5B-5C which illustrates different embodiments of the present invention.

In FIG. 5B, a plurality of central 302 and peripheral 304 chambers are illustrated; each of which is bounded by a crenellated shaped rim 306. Such a configuration may be used so as to enables several assessment simultaneously.

In FIGS. 5C-5D the side by side configuration is illustrated. According to said embodiment, the two chambers are not are co-axial, but rather positioned one next to the other.

In FIGS. 5E-5F, a schematic description of the pilepile configuration is illustrated. According to said embodiment, the two chambers are not co-axial, but rather positioned one the other the other.

Reference is made to FIGS. 5E, 5F, in which sperm separation device 140 in more detail. The device may include cover 334, (shown in FIG. 5E. Not shown in FIG. 5F) which is used to guide actuators 333 to position. A biologic sample (such as semen) 308 is inserted via central opening marked S, and separation-enabling agent alternatively support medium, 310, may be inserted via peripheral opening marked M. Harvested assay is removed from sperm separation device 140, via M opening.

Of cores, M opening may be in center of cover, and S in periphery.

The insertion and extraction of the sample or the separation agent is performed via a cannula, needle, syringe or any other actuator (333).

Inserted needle or cannula, in FIGS. 5E, 5F, is via peripheral opening, showing no interface with sample 308. Separation-enabling agent alternatively support medium, 310, is inserted via said cannula, and is in overplayed on sample 308, to create fluid interface, 331 between 308 and 310.

When the separation-enabling agent alternatively support medium, 310, is inserted, the same starts to flow between the peripheral chamber 304 and central chamber 302, separated by rim 306.

The separation-enabling agent, alternatively support medium, 310, flows in peripheral chamber.

The surface tension of separation-enabling agent alternatively support medium, 310, keeps fluid in peripheral chamber, which is dimensioned with surface roughness and openings, smaller then the breaking force required to brake surface tension of separation-enabling agent alternatively support medium, 310, hence the separation-enabling agent alternatively support medium, 310, continue to flow and fill the periphery 304.

As more separation-enabling agent alternatively support medium, 310 in introduced, the separation-enabling agent alternatively support medium 310 meniscus is building up, until surface tension is weaker them the meniscus hydraulic build up, and it breaks. The separation-enabling agent alternatively support medium, 310 is flowing from periphery 304 onto the sample 308 inside central chamber 302.

Figure 2A:
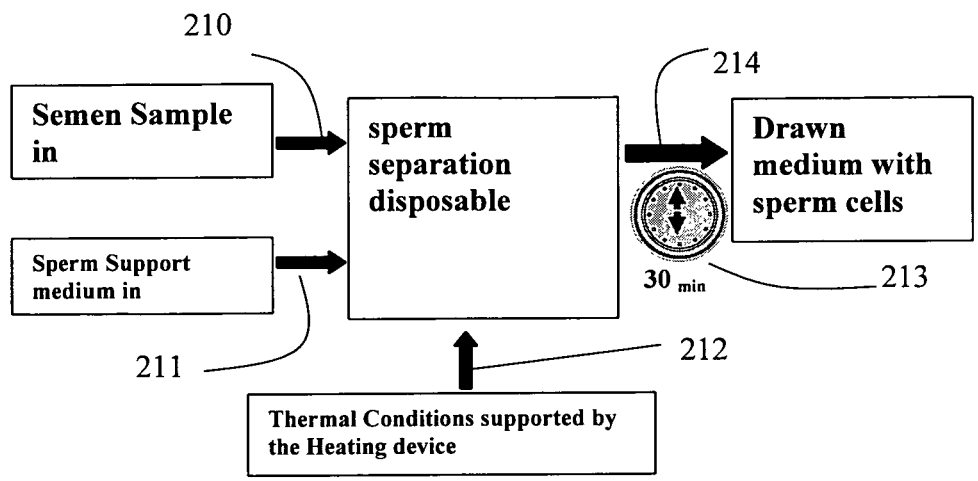
FIG. 2A shows block diagram of operation of the sperm separation system including the heating device (incubation means)
Figure 2B:
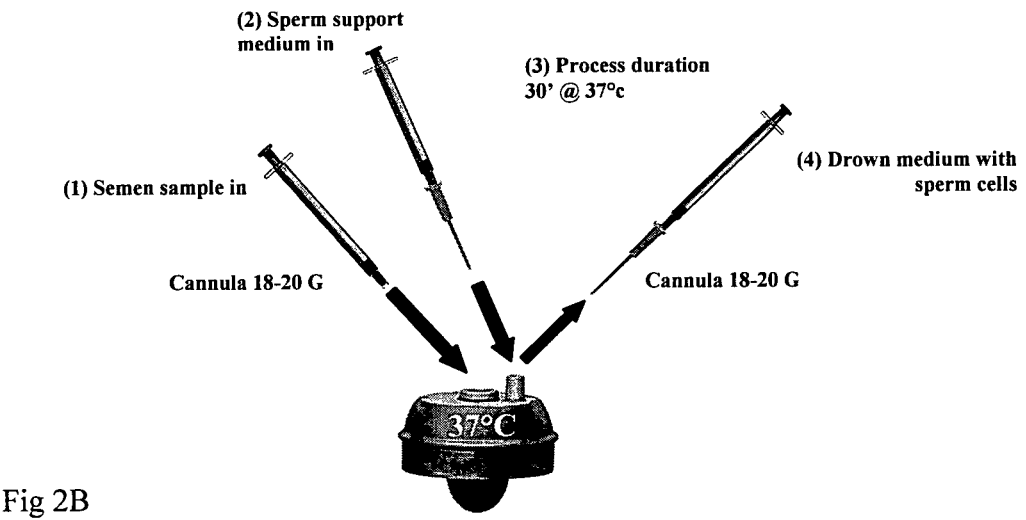
FIG. 2B shows description of operation of the sperm separation device.
Figure 4A:
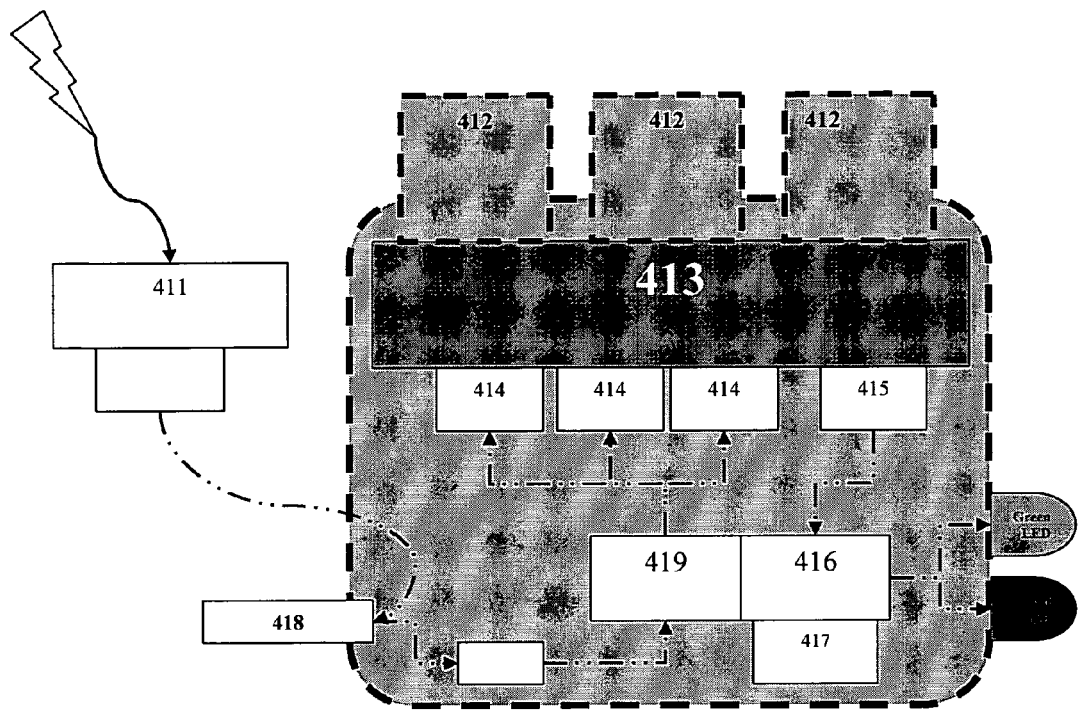
FIG. 4A illustrates a cross-sectional view of a incubation means (e.g., heating device), 200.
Figure 4B:
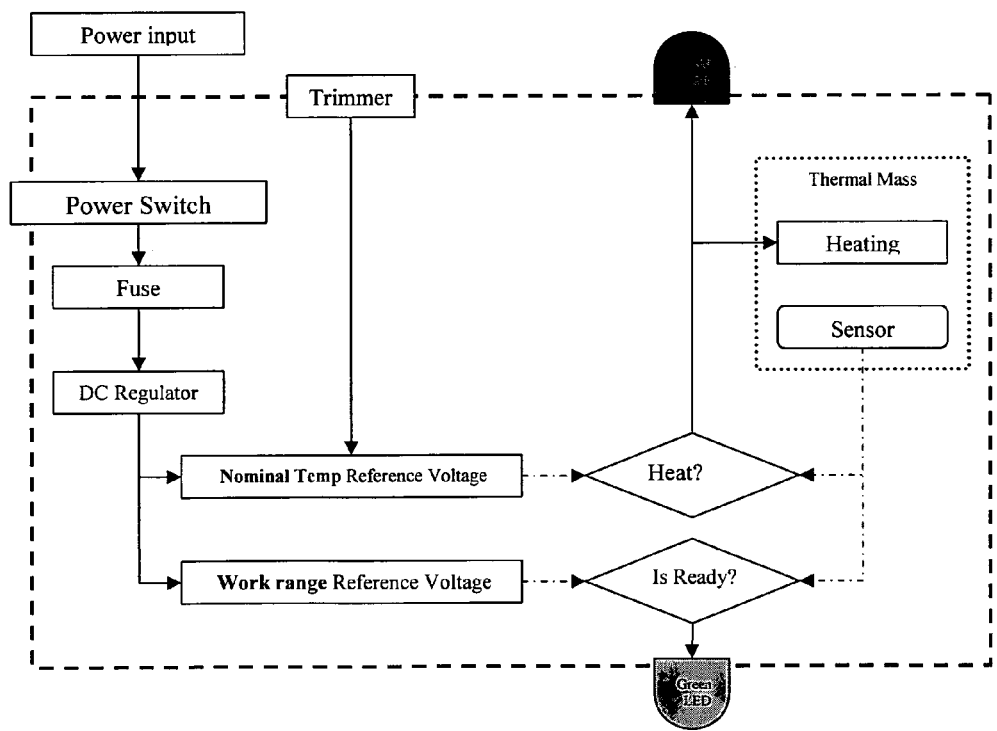
FIG. 4B shows a schematic controlling diagram of the heating device.

Generally speaking, the method of using the sperm separation system of the present invention involves in, inserting a semen sample into the sperm separation device (see step 210, FIG. 2A, step 1, FIG. 2B); inserting the sperm support medium (see step 211, FIG. 2A, step 2, FIG. 2B); thermoregulating the sperm separation device via the incubation means (see step 212, FIG. 2A, step 3, FIG. 2B); awaiting approx. 30 minutes (see step 213, FIG. 2A); and, drawing the medium with the isolated sperm cells (see step 214, FIG. 2A, step 4, FIG. 2B). Reference is now made to FIGS. 4A-4B which illustrate the heating device (incubation means). The heating device may comprise the following elements:
 (a) at least one separator interface 412 into which the sperm separator device is inserted;
 (b) Thermal Mass-Heat Integrator 413
 (c) Common host PC or USB Power adaptor, 411;
 (d) at least one heat units 414;
 (e) at least one heat sensor, 415;
 (f) a control circuit 416;
 (g) a calibration trimer 417;
 (h) a power switch 418;
 (i) a power circuit 419 in communication with the heat units 414.

Such an arrangement may be realized using analogue electronic circuitry, requires no software for its operation, using offset/gain combinations and comparators such as LM 339 and others, heat sensor such as LM 135 and others, available from leading manufacturers. Another possibility is to use digital electronics by incorporating the heating device with local μProcessor/μController, or with general purpose Personal computer as a host. Reference is now made to FIG. 4B which illustrates the operational mode of the heating device. According to one embodiment of the present invention, the heating device is provided with means (e.g., LEDS) adapted to indicate whether the device is ready to be operated. For example, in FIG. 4B, red light led indicates that the device is not ready to operate and a green light led indicates that the device is ready to be used. Of coursecourse, information may be presented on general purpose Personal computer as a host, or locally on common LCD screen, or any audio/video announcement system.

As described above, it is one object of the present invention to provide a naturally based Sperm Separation System (SSS) for separation of at least a portion of sperm cell populations (SCP) characterized by (i) motility in a range between about 5 μm/s to about 15 μm/s at 37°; (ii) slow progressive motility in a range between about 15 μm/s at 37° to about 25 μm/s at 37°; (iii) rapid progressive motility of at least 25 μm/s at 37° and 20 μm/s at 20°; (iv) at least 90% motile sperm cells, having an average of at least 32% normal morphology; or any combination thereof, within an original semen sample, such that an enriched SCP sample is obtained; said SSS comprising:
 a. a sperm separation device, comprising:
  i) at least one first chamber adapted to contain at least a portion of said original semen sample; said first chamber is characterized by pre-determined 3D shape and volume, V; said first chamber is bounded by a rim such that said original semen sample is kept below said rim; wherein said rim is crenellated shaped; and,
  ii) at least one second chamber in physical communication with said first chamber and said rim; said second chamber is characterized by pre-determined 3D shape and volume, $V_1$, wherein said $V_1$ is substantially smaller than V;
   said second chamber is adapted to reside said enriched SCP sample; said enriched SCP sample comprising at least a portion of said SCP crossing through the crenellations in said crenellated shaped rim such that said separation of said SCP from said original semen sample is obtained and said enriched SCP sample is provided;
 b. incubation means, adapted to socket at least one of said cell separation device and to homogeneously thermoregulate the temperature within the same;
 wherein said pre-determined 3D shape of said first and second chambers and said crenellations in said rim enables at least one of the following is held true:
  i) efficacy of said SSS is at least 95%;
  ii) the total number of motile CSP separated into said second chamber is at least $4*10^6$ as examined with phase contrast or light microscopes, when said original semen sample is a NORMAL sample as defined by WHO 1999 Appendix IA clause 2.5 and comprises at least $5*10^6$ [motile CSP/ml];
  iii) the concentration of motile CSP separated into said second chamber is at least $4*10^6$ [cell/ml] as measured with phase contrast or light microscopes when the concentration of motile CSP in said original semen sample is at least $5*10^6$ [motile sperm cell/ml];

iv) the total number of progressive motile CSP separated into said second chamber is at least $2*10^6$ as measured with phase contrast or light microscopes, when said original semen sample comprises at least $2.5*10^6$ [progressive motile CSP/ml];

v) the average percentage of CSP having normal morphology in said enriched sample is at least 32% in as measured with phase contrast or microscopes when said original semen sample comprises an average of at least 18% CSP having normal morphology.

It is another object of the present invention to provide the SSS as define above, wherein said $V_1$ equals to said V.

It is another object of the present invention to provide the SSS as define above, wherein said first chamber is dimpled-shaped.

It is another object of the present invention to provide the SSS as define above, wherein said first chamber and said second are co-axial such that said second chamber is peripheral and circumferentially encircles said first chamber.

It is another object of the present invention to provide the SSS as define above, wherein said first chamber and said second are in a side by side configuration.

It is another object of the present invention to provide the SSS as define above, wherein said first chamber and said second are in a pile configuration.

It is another object of the present invention to provide the SSS as define above, wherein said pre-determined 3D shape of said first chamber is characterized by a cross sectional area of circular and is defined by radius R.

It is another object of the present invention to provide the SSS as define above, wherein said pre-determined 3D shape of said second chamber is characterized by a cross sectional area of circular and is defined by radius $R^1$.

It is another object of the present invention to provide the SSS as define above, wherein said pre-determined 3D shape of said first chamber is characterized by a cross sectional area having n ribs where n is an integer higher than or equals to 3, or any combination thereof.

It is another object of the present invention to provide the SSS as define above, wherein said pre-determined 3D shape of said second chamber is characterized by a cross sectional area having n ribs where n is an integer higher than or equals to 3, or any combination thereof.

It is another object of the present invention to provide the SSS as define above, wherein said SSS increases the efficacy of said separation and the enrichment of said SCP within said enriched SCP sample such that said increase is greater than the sum of said pre-determined 3D shape of said first and second chamber effectiveness and said crenellations in said rim effectiveness.

It is another object of the present invention to provide the SSS as define above, wherein said SCP are adapted to cross through or above the crenellations in said crenellated shaped rim into said second chamber upon introduction of a support medium into either said first chamber and/or said second chamber such that said support medium is in liquid communication with at least a portion of said original semen sample.

It is another object of the present invention to provide the SSS as define above, wherein at least one of the following is held true:

i) the total number of motile CSP separated into said second chamber is at least $4*10^6$ as examined with phase contrast or light microscopes, when said original semen sample is a NORMAL sample as defined by WHO 1999 Appendix IA clause 2.5;

ii) the concentration of motile CSP separated into said second chamber is at least $4*10^6$ [cell/ml] as measured with phase contrast or light microscopes when said original semen sample is a NORMAL sample as defined by WHO 1999 Appendix IA clause 2.5;

iii) the total number of progressive motile CSP separated into said second chamber is at least $2*10^6$ as measured with phase contrast or light microscopes, when said original semen sample is a NORMAL sample as defined by WHO 1999 Appendix IA clause 2.5;

iv) the average percentage of CSP having normal morphology in said enriched sample is at least 32%, as measured with phase contrast or light microscopes when said original semen sample is a NORMAL sample as defined by WHO 1999 Appendix IA clause 2.5.

It is another object of the present invention to provide the SSS as define above, wherein at least one of the following is held true:

i) the average % of motile sperm cells in said enriched sample in said second chamber is increased by an average of at least 210% relatively to the average % motile sperm cells in said original semen sample, as measured with phase contrast or light microscopes;

ii) the % of progressive motile CSP in said enriched sample in said second chamber is increased by an average of at least 290% relatively to the average % progressive motile CSP in said original semen sample, as measured with phase contrast or light microscopes;

iii) the % of CSP having normal morphology in said enriched sample in said second chamber is increased by an average of at least 260% relatively to the average % of CSP having normal morphology in said original semen sample, as measured with phase contrast or light microscopes.

It is another object of the present invention to provide the SSS as define above, wherein at least one of the following is held true:

a. the average % of motile sperm cells isolated into said enriched sample is multiplied by at least 2.0 relatively to the average % motile sperm cells in said original semen sample as measured with phase contrast or light microscopes;

b. the average % of progressive motile sperm cells isolated into said second chamber is multiplied by at least 1.4 relatively to the average % of progressive motile sperm cells in said original semen sample as measured with phase contrast or light microscopes;

c. the % of decrease said CSP having abnormal round cells morphology isolated into said second chamber is about 99% as measured with phase contrast or light microscopes.

It is another object of the present invention to provide the SSS as define above, wherein said isolated sperm cells are depleted of round non motile cells selected from group of round non sperm cells, immature sperm cells, dead sperm cells or any combination thereof.

It is another object of the present invention to provide the SSS as define above, wherein the average yield of separation is higher than 58%, especially about 62% relatively to said original semen sample before said separation.

It is another object of the present invention to provide the SSS as define above, wherein at least an average of at least 70% especially 84% of said isolated sperm cells are progressively motile.

It is another object of the present invention to provide the SSS as define above, wherein said SSS is further adapted to perform assays selected from a group consisting of: a sperm cells concentration assay, a semen pH assay, a leukocytes concentration threshold assay, a sperm cells motility assay, a sperm cells morphology assay, a semen volume assay, a viscosity assay and a turbidity assay.

It is another object of the present invention to provide the SSS as define above, wherein said assays is adapted to facilitate diagnosis of at least one sexually transmitted disease (STD) selected from a group consisting of: syphilis, gonorrhea, Candida, human papiloma virus (HPV), mycoplasma, ureaplasma, human immunodeficiency virus (HIV), Chlamydia, herpes simplex virus, Hepatitis B, Trichomonas and Hepatitis C.

It is another object of the present invention to provide the SSS as define above, wherein said SSS is sealed such that no contamination of the environment outside said cartridge is performed.

It is another object of the present invention to provide the SSS as define above, additionally comprising a reagent adapted to, upon contact with said original sperm sample, to yield a reaction and/or a colored compound indicating (i) existence; or, (ii) concentration of a component in said original or enriched sample; (iii) a result of said at least one assay.

It is another object of the present invention to provide the SSS as define above, wherein said reagent is selected from a group consisting of cell support medium, labeling compounds, markers, peptide, color-changeable pad or any combination thereof.

It is another object of the present invention to provide the SSS as define above, wherein said original sample is selected from a group consisting of: a semen sample, a vaginal secretion sample, a vaginal cell sample, a blood sample, a urine sample, a saliva sample, a lymph sample or any combination thereof.

It is another object of the present invention to provide the SSS as define above, wherein said SSS is made of substantially rigid materials or a substantially flexible materials or any combination thereof.

It is another object of the present invention to provide the SSS as define above, further comprising at least one sensor adapted to interface with said cartridge to facilitate said at least one assay.

It is another object of the present invention to provide the SSS as define above, further comprising a control adapted to perform at least one action selected from a group consisting of: (i) receive a reading from said at least one sensor, said sensor is in communication with said cartridge; (ii) analyze said reading; (iii) analysis readings received based upon said at least one of said assays; and (iv) output said analysis of said original sperm sample.

It is another object of the present invention to provide the SSS as define above, wherein said cell separation device is socketed in said incubation means for a pre-determined period of about 10 minutes to about 60 minutes.

It is another object of the present invention to provide the SSS as define above, wherein said incubation means are adapted to thermoregulate the temperature within said cell separation device to a temperature of about 30 Celsius degrees and about 39 Celsius degrees, more preferably about 35.5 Celsius degrees to about 37.5 Celsius degrees.

It is another object of the present invention to provide the SSS as define above, wherein said temperature is about 37 Celsius degrees.

It is another object of the present invention to provide the SSS as define above, wherein said cell separation device additionally comprising a cover; said cover comprises at least two orifices; said orifices are adapted to enable guided entry or aspiration of fluids aspiration means or actuators to either said first central chamber or said second chamber.

It is another object of the present invention to provide the SSS as define above, wherein said actuators are selected from a group consisting of needle, cannula, pipette, syringe any positive displacement system such as a peristaltic pump or any combination thereof.

It is another object of the present invention to provide the SSS as define above, wherein said cell separation device additionally comprising at least one orifice adapted to enable entry or aspiration of fluids aspiration means or actuators either to said first central chamber or said second chamber.

It is another object of the present invention to provide the SSS as define above, wherein said actuators are selected from a group consisting of needle, cannula, pipette, syringe any positive displacement system such as a peristaltic pump or any combination thereof.

It is another object of the present invention to provide the SSS as define above, wherein said SCP are collected from said second chamber manually or automatically.

It is another object of the present invention to provide the SSS as define above, further adapted to assess motility of sperm cells and/or isolate motile sperm within an enriched semen sample for assisting fertility or diagnose sperm cells.

It is another object of the present invention to provide the SSS as define above, further adapted to assess motility of sperm cells in said original or enriched semen sample, and/or isolate motile sperm of said original or enriched semen sample for fertility treatments selected from a group consisting of: intra uterine insemination (IUI), vaginal insemination, and in-vitro fertilization (IVF).

It is another object of the present invention to provide the SSS as define above, wherein said rim is configured with specific surface roughness or serration to facilitate required surface tension, surface energy, capillary forces capabilities for specific sample/reagent combination.

It is another object of the present invention to provide the SSS as define above, wherein said support medium is selected from a group consisting of Ringer's solution, Hartmann's solution, Saline Hyaluronic acid, Phosphor buffered saline (PBS) or any other sperm preparation or separation or washing medium adapted to facilitate said separation.

It is another object of the present invention to provide the SSS as define above, wherein said first central chamber of said SSS is adapted to contain an original semen sample having a volume measurement ranging from about 0.1 ml to about 10 ml.

It is another object of the present invention to provide the SSS as define above, wherein said SSS is adapted for diagnostics of male infertility.

It is another object of the present invention to provide the SSS as define above, wherein said SSS is disposable.

It is another object of the present invention to provide the SSS as define above, wherein said SSS is reusable and may be configured for multi-use.

It is another object of the present invention to provide a naturally based method for separating at least a portion of sperm cell populations (SCP) characterized by (i) motility in a range between about 5 µm/s to about 15 µm/s at 37°; (ii) slow progressive motility in a range between about 15 µm/s at 37° to about 25 µm/s at 37°; (iii) rapid progressive motility of at least 25 µm/s at 37° and 20 µm/s at 20°; (iv) at least 90% motile sperm cells, having an average of at least 32% normal morphology; or any combination thereof, within an original semen sample into an enriched SCP sample. The method comprises steps selected inter alia from:

a. providing a cell separation device, comprising:
   i) at least one first chamber; said first chamber is bounded by a rim; wherein said rim is crenellated shaped; said first chamber is characterized by pre-determined 3D shape and volume, V; and,
   ii) at least one second chamber in physical communication with said first chamber and said rim;
b. configuring said second chamber with pre-determined 3D shape and volume, $V_1$, wherein said $V_1$ is substantially smaller than V;
c. obtaining incubation means;
d. socketing said cell separation device within said incubation means;
e. depositing said original semen sample within said first chamber such that said original semen sample is kept below said rim;
f. introducing a support medium into either said first chamber and/or said second chamber such that said support medium is in liquid communication with at least a portion of said original semen sample; thereby residing at least a portion of said SCP crossing through the crenellations in said crenellated shaped rim within said second chamber; and,
g. separating said SCP from said original semen sample into said enriched sample;

wherein said step (b) of configuring said second chamber with predetermined 3D shape and performing said steps (d-g) while constantly and homogeneously thermoregulating the temperature within said cell separation device enables at least one of the following to be held true:

i) efficacy of said SSS is at least 95%;
ii) the total number of motile CSP separated into said second chamber is at least $4*10^6$ as examined with phase contrast or light microscopes, when said original semen sample is a NORMAL sample as defined by WHO 1999 Appendix IA clause 2.5 and comprises at least $5*10^6$ [motile CSP/ml];
iii) the concentration of motile CSP separated into said second chamber is at least $4*10^6$ [cell/ml] as measured with phase contrast or light microscopes when the concentration of motile CSP in said original semen sample is at least $5*10^6$ [motile sperm cell/ml];
iv) the total number of progressive motile CSP separated into said second chamber is at least $2*10^6$ as measured with phase contrast or light microscopes, when said original semen sample comprises at least $2.5*10^6$ [progressive motile CSP/ml];
v) the average percentage of CSP having normal morphology in said enriched sample is at least 32% in as measured with phase contrast or microscopes when said original semen sample comprises an average of at least 18% CSP having normal morphology.

It is another object of the present invention to provide the method as define above, additionally comprising step of configuring said first chamber as dimpled-shaped.

It is another object of the present invention to provide the method as define above, additionally comprising step of configuring said $V_1$ to be equal to said V.

It is another object of the present invention to provide the method as define above, additionally comprising step of configuring said first chamber and said second in a co-axial manner such that said second chamber is peripheral and circumferentially encircles said first chamber.

It is another object of the present invention to provide the method as define above, additionally comprising step of configuring said first chamber and said second are in a side by side configuration.

It is another object of the present invention to provide the method as define above, additionally comprising step of configuring said first chamber and said second in a pile configuration It is another object of the present invention to provide the method as define above, additionally comprising step of configuring said pre-determined 3D shape of said first chamber with a circular cross sectional area having radius R.

It is another object of the present invention to provide the method as define above, additionally comprising step of configuring said pre-determined 3D shape of said second chamber with a circular cross sectional area having radius $R^1$.

It is another object of the present invention to provide the method as define above, additionally comprising step of configuring said pre-determined 3D shape of said first chamber with a cross sectional area having n ribs where n is an integer higher than or equals to 3, or any combination thereof.

It is another object of the present invention to provide the method as define above, additionally comprising step of configuring said pre-determined 3D shape of said second chamber with a cross sectional area having n ribs where n is an integer higher than or equals to 3, or any combination thereof.

It is another object of the present invention to provide the method as define above, additionally comprising step of enabling said SCP to cross through or above the crenellations in said crenellated shaped rim into said second chamber upon introduction of a support medium into either said first chamber and/or said second chamber such that said support medium is in liquid communication with at least a portion of said original semen sample.

It is another object of the present invention to provide the method as define above, wherein said steps (d-f) is performed while constantly and homogeneously thermoregulating the temperature within said cell separation device such that at least one of the following to be held true:

i) the total number of motile CSP separated into said second chamber is at least $4*10^6$ as examined with phase contrast or light microscopes, when said original semen sample is a NORMAL sample as defined by WHO 1999 Appendix IA clause 2.5;
ii) the concentration of motile CSP separated into said second chamber is at least $4*10^6$ [cell/ml] as measured with phase contrast or light microscopes when said original semen sample is a NORMAL sample as defined by WHO 1999 Appendix IA clause 2.5;
iii) the total number of progressive motile CSP separated into said second chamber is at least $2*10^6$ as measured with phase contrast or light microscopes, when said original semen sample is a NORMAL sample as defined by WHO 1999 Appendix IA clause 2.5;
iv) the average percentage of CSP having normal morphology in said enriched sample is at least 32%, as measured with phase contrast or light microscopes when said original semen sample is a NORMAL sample as defined by WHO 1999 Appendix IA clause 2.5.

It is another object of the present invention to provide the method as define above, wherein said steps (d-f) is performed while constantly and homogeneously thermoregulating the temperature within said cell separation device such that at least one of the following to be held true:

i) the average % of motile sperm cells in said enriched sample in said second chamber is increased by an average of at least 210% relatively to the average % motile sperm cells in said original semen sample, as measured with phase contrast or light microscopes;
ii) the % of progressive motile CSP in said enriched sample in said second chamber is increased by an average of at least 290% relatively to the average % progressive motile CSP in said original semen sample, as measured with phase contrast or light microscopes;
iii) the % of CSP having normal morphology in said enriched sample in said second chamber is increased by an average of at least 260% relatively to the average % of CSP having normal morphology in said original semen sample, as measured with phase contrast or light microscopes.

It is another object of the present invention to provide the method as define above, wherein said steps (d-f) is performed while constantly and homogeneously thermoregulating the temperature within said cell separation device such that at least one of the following to be held true:
a. the average % of motile sperm cells isolated into said enriched sample is multiplied by at least 2.0 relatively to the average % motile sperm cells in said original semen sample as measured with phase contrast or light microscopes;
b. the average % of progressive motile sperm cells isolated into said second chamber is multiplied by at least 1.4 relatively to the average % of progressive motile sperm cells in said original semen sample as measured with phase contrast or light microscopes;
c. the % of decrease said CSP having abnormal round cells morphology isolated into said second chamber is about 99% as measured with phase contrast or light microscopes.

It is another object of the present invention to provide the method as define above, wherein said step of separating said SCP from said original semen sample additionally comprising step of providing said separated SCP depleted of round non motile cells selected from group of round non sperm cells, immature sperm cells, dead sperm cells or any combination thereof.

It is another object of the present invention to provide the method as define above, wherein said step of separating said SCP from said original semen sample additionally comprising step of providing said separated SCP with an average of at least 70%, especially 84% progressively motile sperm cells.

It is another object of the present invention to provide the method as define above, wherein said step of separating said SCP from said original semen sample additionally comprising step of providing an average yield separation which is higher than 58%, especially 62% in average relatively to said original semen sample before said separation.

It is another object of the present invention to provide the method as define above, additionally comprising step of performing assays selected from a group consisting of: a sperm cells concentration assay, a semen pH assay, a leukocytes concentration threshold assay, a sperm cells motility assay, a sperm cells morphology assay, a semen volume assay, a viscosity assay and a turbidity assay.

It is another object of the present invention to provide the method as define above, additionally comprising step of facilitating diagnosis of at least one sexually transmitted disease (STD) selected from a group consisting of: syphilis, gonorrhea, Candida, human papiloma virus (HPV), mycoplasma, ureaplasma, human immunodeficiency virus (HIV), Chlamydia, herpes simplex virus, Hepatitis B, Trichomonas and Hepatitis C.

It is another object of the present invention to provide the method as define above, additionally comprising step of providing said SSS as a SSS sealed such that no contamination of the environment outside said cartridge is provided.

It is another object of the present invention to provide the method as define above, additionally comprising step of providing said SSS with a reagent adapted to, upon contact with said original or enriched sample, to yield a reaction and/or a colored compound indicating (i) existence; or, (ii) concentration of a component in said original or enriched sample; (iii) a result of said at least one assay.

It is another object of the present invention to provide the method as define above, additionally comprising step of selecting said reagent from a group consisting of cell support medium, labeling compounds, markers, peptide, color-changeable pad or any combination thereof.

It is another object of the present invention to provide the method as define above, additionally comprising step of selecting said original sample is selected from a group consisting of: a semen sample, a vaginal secretion sample, a vaginal cell sample, a blood sample, a urine sample, a saliva sample, a lymph sample or any combination thereof.

It is another object of the present invention to provide the method as define above, additionally comprising step of configuring said SSS to be made of substantially rigid materials or a substantially flexible materials or any combination thereof.

It is another object of the present invention to provide the method as define above, wherein said step of socketing said cell separation device within said incubation means is performed for a pre-determined period of about 10 minutes to about 60 minutes.

It is another object of the present invention to provide the method as define above, wherein said step of homogeneously thermoregulating the temperature within said cell separation device, thermoregulates the temperature to about 30 Celsius degrees and about 39 Celsius degrees, more preferably about 35.5 Celsius degrees to about 37.5 Celsius degrees.

It is another object of the present invention to provide the method as define above, wherein said step of providing said cell separation device provides the same with a cover; said cover comprises at least two openings said orifices are adapted to enable guided entry or aspiration of fluids aspiration means or actuators to either said first central chamber or said second chamber.

It is another object of the present invention to provide the method as define above, additionally comprising step of selecting said actuators from a group consisting of needle, cannula, pipette, syringe any positive displacement system such as a peristaltic pump or any combination thereof.

It is another object of the present invention to provide the method as define above, wherein said step of providing said cell separation device provides the same with one orifice adapted to enable entry or aspiration of fluids aspiration means or actuators either to said first central chamber or said second chamber.

It is another object of the present invention to provide the method as define above, additionally comprising step of selecting said actuators from a group consisting of needle, cannula, pipette, syringe any positive displacement system such as a peristaltic pump or any combination thereof.

It is another object of the present invention to provide the method as define above, additionally comprising step of collecting said SCP from said second chamber manually or automatically.

It is another object of the present invention to provide the method as define above, additionally comprising step of assessing motility of sperm cells and/or isolate motile sperm within an enriched semen sample for assisting fertility.

It is another object of the present invention to provide the method as define above, additionally comprising step of assessing motility of sperm cells in said enriched semen sample, and/or isolate motile sperm of said semen sample for fertility treatments selected from a group consisting of: intra uterine insemination (IUI), vaginal insemination, and in-vitro fertilization (IVF).

It is another object of the present invention to provide the method as define above, additionally comprising step of configuring said rim with specific surface roughness surface energy, capillary forces or serration to facilitate required surface tension capabilities for specific sample/reagent combination.

It is another object of the present invention to provide the method as define above, additionally comprising step of selecting said support medium from a group consisting of Ringer's solution, Hartmann's solution, Saline Hyaluronic acid, Phosphor buffered saline (PBS) or any other sperm preparation/separation/washing medium adapted to facilitate said separation.

It is another object of the present invention to provide the method as define above, wherein said first central chamber of said SSS is adapted to contain an original semen sample having a volume measurement ranging from about 0.1 ml to about 10 ml.

It is another object of the present invention to provide the method as define above, wherein said SSS is adapted for diagnostics of male infertility.

It is still object of the present invention to provide the method as define above, additionally comprising step of configuring said SSS as disposable.

It is lastly an object of the present invention to provide the method as define above, additionally comprising step of configuring said SSS for multi-use.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

EXAMPLES

Examples are given in order to prove the embodiments claimed in the present invention. The example, which is a clinical test, describes the manner and process of the present invention and set forth the best mode contemplated by the inventors for carrying out the invention, but are not to be construed as limiting the invention.

Example 1

Figure 2G:
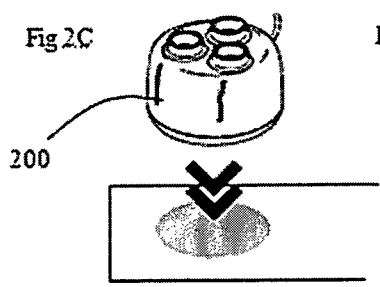
FIG. 2C-2S shows schematic illustration of the procedure of using the sperm separation system.
Figure 2G:
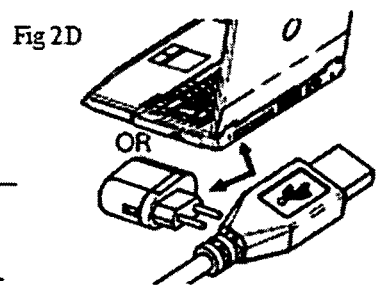
Figure 2G:
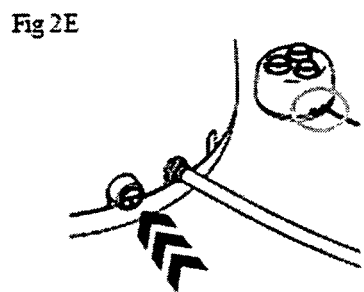
Figure 2G:
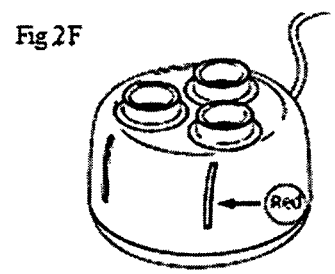
Figure 2G:
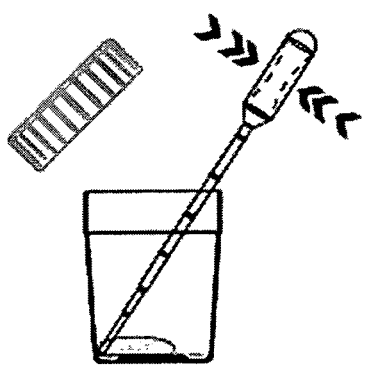
Figure 2H:
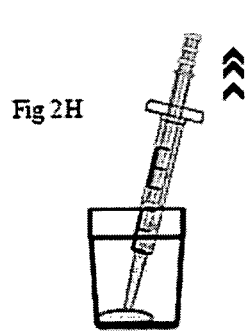
Figure 2I:
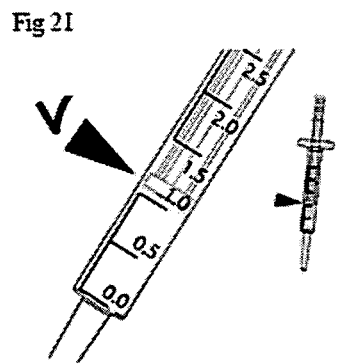
Figure 2J:
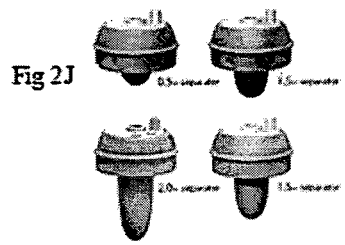
Figure 2K:
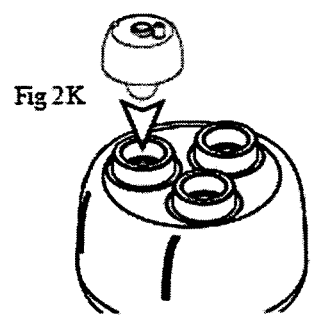
Figure 2L:
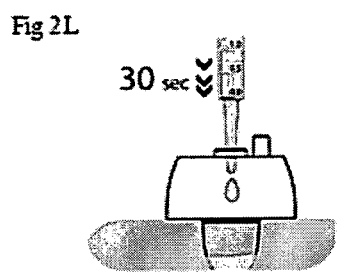
Figure 2M:
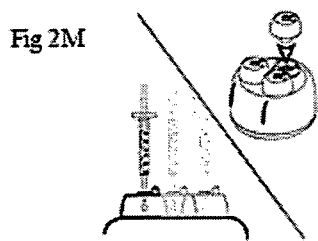

Methods of Using the Sperm Separation System SSS in Laboratories, Clinics and Home Use Method:
The following is the procedure guidelines for using sperm or other cells separation system:

1. In FIG. 2C the heating device (i.e., the incubation means) 200 is placed (e.g., on the physician's desk; In FIG. 2D: the heating device 200 is connected (e.g., to a PC).
2. FIG. 2E to FIG. 2F: the heating device 200 is turned on at least 30 minutes before use (so as to achieve the desired temperature).
3. In FIG. 2G, after the collected semen sample has been liquefied for 30 min within the collection apparatus or semen sample container 150, an actuator in a form of 1 ml or 3 ml sterile plastic pipette is used for homogenizing the sample (about 1 ml sample is raised and lowered 10 times).
4. Optionally, the semen sample is assessed for sperm cells concentration, motility and morphology characters using the light microscope. This assessment may be used as standard of practice in a laboratory, as specified in WHO laboratory manual for the examination of human semen and sperm cervical mucus interaction fourth edition (WHO, 1999), or using any commercially available tools and methods such as Spermac Stain available from Fertipro NV Belgium for morphology, Baby start for concentration assay available from Lake consumer products Inc USA, Quick Check for pH and/or Leucocytes available from MES Israel, Eosin-Nigrosin staining kit for sperm cells vitality assessment from Estar Technologies ltd., Israel.
5. In FIG. 2H a semen sample is loaded into a syringe; in FIG. 2I the volume of the sample is read.
6. FIG. 2J, the sperm separation device 140 or separator used for sperm or other cells separation is chosen (i.e., from different volumes if 0.5 ml, 1 ml, 1.5 ml and 2 ml).
7. FIG. 2K: the sperm separation device or separator chosen is placed in the appropriate cavity in the heating device 200.
8. The temperature is set for 37° C.
9. FIG. 2L, the cannula is entered to the central orifice in lid
10. In FIGS. 2L, 2M, the exact semen sample volume is gently lowered into of the sperm separation device or separator (recommended 30-60 sec for the entire volume of the syringe) using the syringe as an actuator.
11. FIGS. 2N, and 2O, a new 1 ml syringe or an actuator is used to draw 0.8 ml of sperm support medium pre heated to 37° C.
12. In FIG. 2P, the cannula is entered to the farthest orifice in lid and hence, the medium is gently lowered into the separator (i.e., sperm separator device) of the present invention.
13. FIG. 2Q, the physician is required to wait for 30 minutes till the procedure is completed.
14. If required, a new 1 ml syringe an actuator is used with a new cannule or needle 18 or 20G.
15. in FIG. 2R, the cannule is entered into the farthest orifice in lid until it reaches the bottom of the separator.
16. the medium with harvested sperm cells or other cells is gently raised.
17. FIG. 2S, the harvested sperm cells are transferred to a 2 ml eppendorf tube, or other acceptable container.
18. The drawn harvested sperm cells are ready for assessment.
19. Optionally or alternatively, remove Needle or cannula from syringe actuator, and incorporate insemination catheter, as available from Cook medical, USA, or other source
20. Optionally, Assess semen sample for sperm cells concentration, motility and morphology characters using the light microscope. This assessment may be used as standard of practice in a laboratory, as specified in WHO laboratory manual for the examination of human semen and sperm cervical mucus interaction fourth edition (WHO, 1999), or using any commercially available tools and methods such as Spermac Stain available from Fertipro NV Belgium for morphology, Baby start for concentration assay available from Lake consumer products Inc USA, Quick Check for pH and/or Leucocytes available from MES Israel, Eosin-Nigrosin staining kit for sperm cells vitality assessment from Estar Technologies ltd., Israel.

21. Of course, other system options are present (as depositing the semen sample in the farthest orifice and medium in the central orifice in lid), and some of the steps may be omitted (For example for home use there is no need to fill CRF), or incorporate several operations with single actuator.

As described above, incubation means (i.e., heating device) is provided with the SSS.

The Heating Device is a unique heating system, designed specifically to fit the separation device of the present invention.

The heating Device enables the sperm separation procedure to be performed at the optimal temperature. The Heating Device is simple to operate and contains:
Power switch: Push Button—toggle between on and off, marked as
it is provided with means adapted to visually indicate (e.g., via leds) that the heating device is ready to use or not. Green LED indicating: "Ready for use", Red LED indicating: "Heating on"
USB connector to a USB port Principle of Operation—Heating Device The Heating Device is desktop mounted, capable of maintaining temperature required for the sperm separation process, and consists of resistive load heaters, thermally controlled, factory calibrated. The Heating Device requires preheat time of up to 45 min, before starting the sperm separation procedure.

Principle of Operation—Cells Separation Device

The system of the present invention enables the best spermatozoa (progressively motile and morphology wise) to migrate from the original semen sample to the sperm support medium, in a very natural way without mechanical handling.

The immotile and/or dead sperm cells, round cells and debris stay in the original semen. The harvested sperm cells population is suitable for insemination or for in vitro fertilization.

Progressively motile and normal morphology sperm cells are the prerequisite for fertilization and embryo development. However, more factors contribute for successful fertilization, hence the separating procedure is not a guarantee for the ovum fertilization occurrence and for further embryo normal development.

Preparation Before Use

The patient is required to collect his ejaculated semen sample into a sterile, clean, wide-mouthed container (as described in FIG. 5a) after 3-7 days of abstention.

The sperm cells isolation procedure using the system of the present invention should start within an hour post the ejaculation.

Reference is now made to FIGS. 2c-2f which illustrates the use of the heating device (i.e., the incubation means).

1. a dose of sperm support medium is allowed to be heated up from the storage temperature to room temperature.
2. the Heating Device (incubation means), 200 is placed on a working platform/desk in a clear area.
3. the Heating Device is connected to one of the following power sources:
   AC-USB Power adapter
   Desktop PC USB port.
4. the system is switched on, using the rear power switch (the LED indicators should flash momentarily).

The incubation means may be supplied with visual means adapted to indicate whether the device is operable. For example, in case a red light on—the heating device is not working or not heated enough.

5. Within predetermined amount of time (e.g., 45 min), a Green light should switch on, indicating that the system has reached the normal working temperature.
6. When the Green LED has switched on the system is ready for use.
7. 1 ml sterile plastic pasture pipette is used, which slowly and gently raise and lower about 1 ml sample 10 times without creating bobbles, in order to homogenize the semen sample (see FIG. 2G).

The following protocol is used in order to load the semen sample (see FIG. 2H-K):

8. a dispensing 2.5 ml syringe is used for drawing the semen sample from the container and read the total sample volume (of cores any other volume may be used).
9. the disposable separators (i.e., the sperm separation device) intend to be used is chosen for sperm cells separation (Consult with the following table).
10. separator is placed in the appropriate cavity in the Heating Device (e.g., incubation means).
11. Confirm that the separator is aligned properly.

Recommended Separators for a Given Semen Sample Volume

The following table summarizes which separators to use:

| Separator | Semen Volume | | | | | | | | | | |
|---|---|---|---|---|---|---|---|---|---|---|---|
| | <0.5 ml | 0.5 ml | >0.5 ml <1 ml | 1 ml | 1.5 ml | 2 ml | 2.5 ml | 3 ml | 3.5 ml | 4 ml | 4.5 ml |
| 0.5 ml | Add medium to 0.5 ml and use this separator | + | | | + | + | | + | + | + | |
| 1.0 ml | | | Add medium to 1 ml and use this separator | + | + | | + | + | + | | + |

-continued

| Separator | <0.5 ml | 0.5 ml | >0.5 ml <1 ml | 1 ml | 1.5 ml | 2 ml | 2.5 ml | 3 ml | 3.5 ml | 4 ml | 4.5 ml |
|---|---|---|---|---|---|---|---|---|---|---|---|
| 1.5 ml | | | | | + | + | + | | + | + | |
| 2.0 ml | | | | | | | | + | + | + | |

It should be pointed out that in case that the semen volume is between the volumes mentioned in the table above, a medium should be added in order to reach the nearest higher volume and then use the recommended separators.

For example: if the semen volume is 2.3 ml add 0.2 ml medium and then use the separators recommended for 2.5 ml semen.

Loading the semen sample is performed as follows (sec FIG. 2L-M):
12. the dispensing syringe is inserted into the [S] orifice in lid and gently lower the exact semen volume into the separator (i.e., the sperm separation device) using the syringe. It should take approximately 30sec.
13. Repeat this step for the other two separators intend to be use.

Loading the medium (see FIG. 2N-Q)
14. A 1 ml syringe is taken and draw 0.8 ml from the sperm support medium (of cores any other volume may be used, as may be defined by the 3D3D dimensions of the chambers).
15. The cannula is inserted into the [M] orifice in lid and gently lower the medium into the separator.
16. Repeat the former two stages (loading the medium) for the other two separators intended to be used.
17. Wait approx. 30 min for the completion of the procedure; during this time the motile sperm cells will swim from the middle cone to the sperm support medium placed in the periphery.

Drawing the medium post procedure is performed as follows (see FIG. 2R-S):
18. a new 1 ml syringe is taken. (of course any other volume can be used)
19. the cannula is inserted into the [M] orifice in lid, until it reaches the bottom of the separator. Then the medium is gently raised with harvested sperm cells, and transferred to an eppendorf tube (repeat the former stages (drawing & transferring medium) for the other two separators used).
20. The sample is ready for further use.
21. Dispose all separators and components of Disposable Kit.

Conformity to Europe standard; The system of the present invention is compliance with the following standards:
(j) IEC 60601-1 (1998)+A 1 (1991); A2 (1995) Medical electrical equipment—Part 1-1: General requirements for safety—Safety requirements for medical electrical systems;
(k) IEC 60601-1-2 (2001) Medical electrical equipment—Part 1-2: General requirements for safety—Electromagnetic compatibility;
(l) ANSI/AAMI/ISO 14971 Medical devices—Application of risk management to medical devices (2007);
(m) AAMI HE74:2001 Human factors design process for medical devices;
(n) BS EN 980:1997 Graphical symbols for use in the labeling of medical devices.

Example 2

Laboratory Test Plan Demonstrating the Efficacy of the Sperm Separation System of the Present Invention (Seaforia)

Purpose

The purpose of this laboratory test plan was to evaluate the efficacy of the Sperm Separation System.

Design

In the experiment, 21 volunteers randomly selected from the general population were recruited through an advertisement to donate semen samples. Each sample was evaluated by routine laboratory methods before and after using the Sperm Separation System. The results were analyzed using 3 statistical methods.

The Sperm Separation System is intended to separate motile sperm cells in the semen. Currently there are several techniques for sperm cell separation, all of them requiring laboratory skills and equipment. The Sperm Separation System is a complete system that can be used in the doctor's office, in clinics and in laboratories. The system is simple to operate, requires no preliminary training, and can be performed by doctors and healthcare professionals. The system is based on the original swim-up technique, with the culture medium layered over liquefied semen. After an incubation of 30 minutes, the motile sperm cells migrate from the lower semen layer into the upper culture medium.

Participants

Twenty one volunteers were randomly selected from the general population and recruited to donate semen samples. Donors ranged in age between 23 and 33 years; their average duration of abstinence was 3.6 days. Sixteen semen samples were divided into two independent samples. Thirty six actual semen samples were obtained from 20 participants, as follows: the samples of 17 participants were divided into two, and 2 samples (one of the divided and one of the undivided) were excluded falling into exclusion criteria, total 36 cases (17×2+4−2=36).

Methods

Basic semen sample analysis of the original sample, as well as of the pre- and post-separation fractions, was performed according to World Health Organization WHO criteria (WHO, 1999), and included evaluation of semen volume, sperm cell concentration, percentage of motile spermatozoa from the total sperm count, and percentage of progressively motile sperm cells from the motile ones. Morphological evaluation of sperm cells was performed by light microscopy.

The following parameters were calculated and analyzed using cumulative and proportional statistical analyses: sperm cell transfer rate (%) (Sperm cells transfer rate (%)=(total sperm cells post procedure/total motile sperm cells pre procedure)×100, transfer rate was calculated post procedure), percentage of motile sperm cells, percentage of sperm cells with progressive motility, percentage of decrease in round cell concentration, and yield of sperm cell separation (Yield (%)=(v×c×pm %)/(V×C×PM %)×100 where v is the final preparation volume, V is the volume of semen used, c is the sperm concentration in the final preparation, pm % is the progressive motility of the prepared sperm population, C is the semen sperm concentration, and PM % is the progressive motility of spermatozoa in the semen (Mortimer D, 2000).

In addition, a T-test was performed to analyze the following parameters: percentage of normal morphology sperm cells, total number of motile sperm cells, and total number of progressively motile sperm cells.

Subject Eligibility and Enrollment

Twenty one volunteers were recruited by advertisement for the laboratory test. Whenever the semen sample volume allowed it, the original samples were divided into two independent samples.

Subject inclusion criteria
Capable and willing to sign a consent form and participate in the study
18<Age<45
Male
Subject exclusion criteria
Semen volume <0.6 ml
Sperm cells concentration of <5×10$^6$/ml or <2×10$^6$/ejaculate motile sperm cells
Main Outcome Measures Main outcome measures were defined as the achievement of a notable improvement in at least 3 out of 5 pre-defined semen parameters, and total improvement in at least 90% of the semen samples. Notable improvement was defined as a 20% difference between the baseline and the end process measurements using the Sperm Separation System.

Sperm Separation Procedure

Participants donated a semen sample. The sample was collected in a special sterile cup. Donors were instructed to collect all the semen in the cup and firmly close it after ejaculation. Donors were instructed to deliver the ejaculate immediately post-ejaculation. A qualified lab technician received the semen samples and labeled them with a CRF number and subject initials. The lab technician began semen assessment 30-60 minutes post-ejaculation (30 minutes is the time required for liquefaction).

In case of high semen viscosity post-liquefaction time, the semen sample had to be liquefied mechanically using a plastic Pasteur pipette.

The following data were collected during baseline assessment:

Demographic information
Semen volume, sperm cells concentration, motility and morphology Sperm separation was conducted using the Sperm Separation System.

The concentration, motility and morphological characters of the sperm cells were measured once again post-separation, in the drawn medium.

Results

Thirty six samples were included in the current report (two samples were excluded). System effectiveness was evaluated by comparing the baseline (pre procedure semen) and post-procedure measurements or calculations. Results show that a significant improvement was achieved by using the Sperm Separation System in all 5 parameters. All 36 samples achieved a significant improvement in at least 3 out of 5 primary end points. Furthermore, 32 out of 36 semen samples achieved improvement in all 5 primary end-points. The average improvement for each end-point was as follows:

1. Transfer rate: 50% (95% confidence interval [CI]: 92% to 100%)
2. Percentage of motile sperm cells: 46% (95% CI: 92% to 100%)
3. Percentage of sperm cells with progressive motility: 48% (95% CI: 81% to 99%)
4. Percentage of decrease in round cells concentration: 99% (95% CI: 92% to 100%)
5. Yield of separation: 62% (95% CI: 74% to 97%).

In a proportional analysis, an improvement of >100% was found in all examined parameters, comparing the isolated sperm cell population with the original semen sample.

Three additional factors were analyzed by comparing the baseline vs. the post-procedure measurements. It was found that:

1. There was a significant improvement of normal morphology
2. The total number of motile sperm cells in the original semen sample was significantly larger than in the post-procedure measurements
3. The total number of progressively motile sperm cells in the drawn volume was similar in the baseline and in post-procedure measurements.

Statistical and Sample Size Considerations

The primary efficacy evaluation analysis of the Sperm Separation System, based on a comparison with baseline measurements, summarizes the percentage of procedure that showed a notable improvement in 3 out of 5 tested parameters.

A total of 36 samples were used to achieve a notable improvement in at least 3 out of 5 pre-defined semen parameters in end process measurements vs. baseline evaluation, based on continuous parameters, and maintaining a type I error of 5% (i.e., α=0.05) and a power of at least 80% (total improvement in at least 90% of the semen samples). The results were analyzed by cumulative and proportional calculations.

Three additional factors were assessed or calculated: the percentage of normal morphology sperm cells, the total number of motile sperm cells and the total number of progressively motile sperm cells.

Note that 2 samples were not used because of exclusion criteria unrelated to the procedure.

Results and Statistical Analysis

Demographics and Basic Characteristics

A total of twenty one samples were collected between Dec. 17, 2008 and Jan. 4, 2009. As was specified in the protocol, most of the samples (17) were divided into two independent samples.

Most samples were eligible for the study based on the inclusion and exclusion criteria. Two samples were excluded because of low sperm cells concentration (CRF #15 & #20), leaving 36 samples included in the current report.

The age range of the donors was 23-33 years (average 26, SD 2.7 years). Average duration of abstinence was 3.6 days. The basic characteristics of the donor population and basic experimental data are summarized in, table 1.

TABLE 1

The basic characteristics of the donor population and basic experimental data

| | Average ± STD | Range | Median |
|---|---|---|---|
| Age | 26.2 ± 2.69 | 23-33 | 25 |
| Duration of abstinence (days) | 3.6 ± 0.68 | 3-5 | 4 |
| Analysis time from ejaculation (min) | 33.5 ± 14.74 | 10-70 | 30 |
| Sample volume[1] (ml) | 0.9 ± 0.37 | 0.6-2.0 | 0.75 |

Summary of Procedures
Baseline measurements are presented in Table 2.

| CRF No. | pH | Sperm cell concentration [cells/ml] × $10^6$ | Motile sperm cell concentration [cells/ml] × $10^6$ | % of motile sperm cells | Round cell concentration [cell/ml] × $10^6$ | % of P.M | Morphology of sperm cells (%) | | | | |
|---|---|---|---|---|---|---|---|---|---|---|---|
| | | | | | | | Normal | Head defect | Middle piece defect | Tail defect | Cytoplasmic droplet |
| 001 | 7.8 | 31.3 | 15.9 | 50.80 | 0.55 | 16 | 18 | 72 | 6 | 12 | 4 |
| 002 | 7.8 | 34.7 | 16.3 | 46.97 | 0.47 | 16 | 30 | 68 | 0 | 32 | 0 |
| 003 | 7.8 | 58.1 | 29.4 | 50.60 | 0.23 | 20 | 28 | 60 | 2 | 20 | 0 |
| 004 | 7.8 | 60.6 | 29.1 | 48.02 | 0.23 | 24 | 14 | 80 | 2 | 38 | 2 |
| 005 | 8 | 40.9 | 20.3 | 49.63 | 0.77 | 40 | 34 | 54 | 4 | 26 | 0 |
| 006 | 8 | 44.4 | 21.6 | 48.65 | 0.70 | 20 | 26 | 64 | 0 | 36 | 0 |
| 007 | 8 | 61.3 | 28.1 | 45.84 | 0.31 | 25 | 26 | 62 | 2 | 26 | 2 |
| 008 | 8 | 52.8 | 24.4 | 46.21 | 0.38 | 43 | 26 | 54 | 2 | 54 | 2 |
| 009 | 8 | 65.6 | 29.4 | 44.82 | 0.62 | 52 | 18 | 68 | 2 | 24 | 6 |
| 010 | 8 | 70.6 | 30.6 | 43.34 | 0.62 | 52 | 22 | 58 | 4 | 38 | 12 |
| 011 | 7.8 | 40.3 | 14.1 | 34.99 | 0.54 | 35 | 30 | 50 | 20 | 22 | 4 |
| 012 | 7.8 | 40.3 | 11.9 | 29.53 | 0.53 | 32 | 40 | 50 | 2 | 12 | 4 |
| 013 | 7.6 | 30.6 | 13.8 | 45.10 | 2.34 | 52 | 0 | 68 | 2 | 30 | 22 |
| 014 | 7.6 | 25.0 | 9.7 | 38.76 | 2.81 | 33 | 2 | 82 | 14 | 60 | 4 |
| 016 | 8 | 61.9 | 22.2 | 35.86 | 0.63 | 36 | 32 | 48 | 8 | 34 | 0 |
| 017 | 8 | 69.7 | 25.0 | 35.87 | 1.00 | 67 | 22 | 66 | 8 | 28 | 2 |
| 018 | 7.8 | 26.9 | 16.6 | 61.71 | 0.23 | 39 | 28 | 60 | 4 | 22 | 0 |
| 019 | 7.8 | 31.3 | 16.9 | 53.99 | 0.16 | 36 | 36 | 60 | 0 | 30 | 0 |
| 021 | >8 | 5.3 | 1.9 | 35.40 | 0.62 | 31 | 26 | 66 | 8 | 22 | 2 |
| 022 | 7.8 | 13.1 | 4.4 | 33.44 | 1.63 | 60 | 18 | 78 | 4 | 40 | 0 |
| 023 | 7.8 | 11.6 | 2.8 | 24.22 | 1.33 | 50 | 26 | 58 | 4 | 26 | 2 |
| 024 | 7.6 | 65.3 | 30.3 | 46.40 | 1.56 | 48 | 30 | 58 | 6 | 36 | 0 |
| 025 | 7.6 | 69.4 | 32.5 | 46.83 | 1.95 | 48 | 34 | 50 | 4 | 12 | 0 |
| 026 | 8 | 47.2 | 25.0 | 52.97 | 0.94 | 23 | 48 | 50 | 6 | 16 | 4 |
| 027 | 8 | 47.8 | 21.9 | 45.82 | 0.31 | 36 | 26 | 70 | 10 | 32 | 2 |
| 028 | 7.8 | 40.9 | 20.9 | 51.10 | 0.54 | 64 | 18 | 68 | 4 | 48 | 2 |
| 029 | 7.8 | 64.1 | 30.9 | 48.21 | 0.23 | 56 | 26 | 60 | 4 | 10 | 0 |
| 030 | 7.6 | 50.9 | 24.1 | 47.35 | 0.62 | 32 | 28 | 54 | 22 | 14 | 0 |
| 031 | 7.6 | 51.3 | 21.3 | 41.52 | 0.94 | 44 | 16 | 68 | 10 | 24 | 0 |
| 032 | 7.6 | 43.8 | 20.0 | 45.66 | 0.31 | 35 | 18 | 72 | 10 | 26 | 8 |
| 033 | 8 | 51.6 | 25.9 | 50.19 | 0.94 | 23 | 20 | 60 | 4 | 54 | 8 |
| 034 | 8 | 42.5 | 19.1 | 44.94 | 0.62 | 33 | 12 | 56 | 12 | 64 | 0 |
| 035 | 7.8 | 15.9 | 5.9 | 37.36 | 0.23 | 17 | 8 | 74 | 4 | 46 | 4 |
| 036 | 7.8 | 27.8 | 10.9 | 39.21 | 0.47 | 31 | 16 | 74 | 0 | 46 | 2 |
| 037 | 7.6 | 15.6 | 5.3 | 34.00 | 2.10 | 8 | 4 | 86 | 14 | 50 | 4 |
| 038 | 7.6 | 12.8 | 8.1 | 63.52 | 0.47 | 17 | 12 | 70 | 4 | 46 | 2 |
| Avg | 7.8 | 42.3 | 19.1 | 44.4 | 0.8 | 35.9 | 22.7 | 63.8 | 5.9 | 32.1 | 2.9 |
| STD | 0.16 | 18.68 | 8.82 | 8.26 | 0.65 | 14.77 | 10.42 | 9.77 | 5.28 | 14.26 | 4.29 |
| Min | 7.60 | 5.31 | 1.88 | 24.22 | 0.16 | 8.00 | 0.00 | 48.00 | 0.00 | 10.00 | 0.00 |
| Max | 8.00 | 70.60 | 32.50 | 63.52 | 2.81 | 66.67 | 48.00 | 86.00 | 22.00 | 64.00 | 22.00 |
| Median | 7.80 | 43.15 | 20.60 | 45.83 | 0.62 | 34.78 | 26.00 | 63.00 | 4.00 | 30.00 | 2.00 |

The collected data before separation is summarized in Table 3.

TABLE 3

Summary of the data pre-separation

| CRF No. | Volume of medium inserted (µl) | Volume of semen inserted (µl) | Total number of sperm cells inserted × $10^6$ | Total number of motile sperm cells inserted × $10^6$ | Total number of progressively motile sperm cells inserted × $10^6$ |
|---|---|---|---|---|---|
| 001 | 800 | 500 | 15.7 | 8.0 | 1.3 |
| 002 | 800 | 500 | 17.4 | 8.2 | 1.3 |
| 003 | 800 | 500 | 29.1 | 14.7 | 2.9 |
| 004 | 800 | 500 | 30.3 | 14.6 | 3.5 |
| 005 | 800 | 500 | 20.5 | 10.2 | 4.1 |
| 006 | 800 | 500 | 22.2 | 10.8 | 2.2 |
| 007 | 800 | 500 | 30.7 | 14.1 | 3.5 |
| 008 | 800 | 500 | 26.4 | 12.2 | 5.2 |
| 009 | 800 | 500 | 32.8 | 14.7 | 7.6 |
| 010 | 800 | 500 | 35.3 | 15.3 | 8.0 |
| 011 | 800 | 500 | 20.2 | 7.1 | 2.5 |
| 012 | 800 | 500 | 20.2 | 6.0 | 2.0 |
| 013 | 800 | 500 | 15.3 | 6.9 | 3.6 |
| 014 | 800 | 500 | 12.5 | 4.8 | 1.6 |
| 016 | 800 | 500 | 31.0 | 11.1 | 4.0 |
| 017 | 800 | 500 | 34.9 | 12.5 | 8.3 |
| 018 | 800 | 500 | 13.5 | 8.3 | 3.2 |
| 019 | 800 | 500 | 15.7 | 8.5 | 3.0 |
| 021 | 800 | 500 | 2.7 | 0.9 | 0.3 |
| 022 | 800 | 500 | 6.6 | 2.2 | 1.3 |
| 023 | 800 | 500 | 5.8 | 1.4 | 0.7 |
| 024 | 800 | 500 | 32.7 | 15.2 | 7.3 |
| 025 | 800 | 500 | 34.7 | 16.3 | 7.8 |
| 026 | 800 | 500 | 23.6 | 12.5 | 2.9 |
| 027 | 800 | 500 | 23.9 | 11.0 | 3.9 |
| 028 | 800 | 500 | 20.5 | 10.5 | 6.7 |
| 029 | 800 | 500 | 32.1 | 15.5 | 8.7 |
| 030 | 800 | 500 | 25.5 | 12.1 | 3.9 |
| 031 | 800 | 500 | 25.7 | 10.7 | 4.7 |

TABLE 3-continued

Summary of the data pre-separation

| CRF No. | Volume of medium inserted (μl) | Volume of semen inserted (μl) | Total number of sperm cells inserted $\times 10^6$ | Total number of motile sperm cells inserted $\times 10^6$ | Total number of progressively motile sperm cells inserted $\times 10^6$ |
|---|---|---|---|---|---|
| 032 | 800 | 500 | 21.9 | 10 | 3.5 |
| 033 | 800 | 500 | 25.8 | 13.0 | 3.0 |
| 034 | 800 | 500 | 21.3 | 9.6 | 3.2 |
| 035 | 800 | 500 | 8.0 | 3.0 | 0.5 |
| 036 | 800 | 500 | 13.9 | 5.5 | 1.7 |
| 037 | 800 | 500 | 7.8 | 2.7 | 0.2 |
| 038 | 800 | 500 | 6.4 | 4.1 | 0.7 |
| Avg | | | 21.2 | 9.5 | 3.5 |
| STD | | | 9.34 | 4.41 | 2.4 |
| Min | | | 2.66 | 0.94 | 0.2 |
| Max | | | 35.30 | 16.25 | 8.7 |
| Median | | | 21.58 | 10.30 | 3.2 |

All repeated measurements were carried out with identical inserted semen volume. The total number of cells, as shown in Table 3, was widely distributed.

The measured data post-separation is summarized in Table 4.

TABLE 4

Summary of the data post-separation

| CRF No. | Volume of medium drawn from the system (out) (μl) | Volume of semen left in the system (in) (μl) | Sperm cells concentration in drawn volume [cells/ml] $\times 10^6$ | Motile sperm cells concentration in drawn volume [cells/ml] $\times 10^6$ | Total number of motile sperm cells in drawn volume $\times 10^6$ | Total number of progressively motile sperm cells in drawn volume $\times 10^6$ | % of motile sperm cells in drawn volume |
|---|---|---|---|---|---|---|---|
| 001 | 480 | 580 | 6.9 | 6.6 | 3.15 | 3.0 | 95.35 |
| 002 | 465 | 595 | 5.6 | 5.6 | 2.62 | 2.1 | 100.00 |
| 003 | 470 | 565 | 13.4 | 12.5 | 5.88 | 5.6 | 93.28 |
| 004 | 435 | 575 | 18.8 | 17.5 | 7.61 | 5.4 | 93.09 |
| 005 | 485 | 510 | 12.5 | 11.9 | 5.77 | 3.8 | 95.20 |
| 006 | 445 | 590 | 11.6 | 9.7 | 4.31 | 2.8 | 83.53 |
| 007 | 440 | 500 | 10.3 | 9.7 | 4.26 | 3.6 | 94.08 |
| 008 | 440 | 540 | 10.3 | 8.8 | 3.85 | 3.7 | 84.95 |
| 009 | 425 | 600 | 17.8 | 15.0 | 6.38 | 5.4 | 84.27 |
| 010 | 485 | 590 | 10.6 | 6.9 | 3.34 | 2.7 | 64.91 |
| 011 | 400 | 615 | 4.7 | 4.1 | 1.62 | 0.8 | 86.57 |
| 012 | 445 | 620 | 4.7 | 4.7 | 2.09 | 1.1 | 100.00 |
| 013 | 430 | 645 | 5.9 | 5.3 | 2.28 | 1.7 | 89.39 |
| 014 | 465 | 655 | 5.6 | 5.3 | 2.47 | 1.6 | 94.32 |
| 016 | 490 | 655 | 15.3 | 14.7 | 7.20 | 7.2 | 96.08 |
| 017 | 425 | 640 | 12.8 | 11.9 | 5.06 | 4.0 | 92.97 |
| 018 | 425 | 640 | 10.9 | 10.0 | 4.25 | 4.3 | 91.74 |
| 019 | 465 | 645 | 11.6 | 9.7 | 4.51 | 4.0 | 83.53 |
| 021 | 500 | 650 | 0.9 | 0.9 | 0.47 | 0.5 | 100.00 |
| 022 | 445 | 615 | 1.3 | 0.9 | 0.42 | 0.3 | 75.04 |
| 023 | 480 | 620 | 1.6 | 1.3 | 0.60 | 0.5 | 80.13 |
| 024 | 480 | 485 | 15.9 | 15.0 | 7.20 | 7.2 | 94.34 |
| 025 | 420 | 620 | 25.6 | 22.5 | 9.45 | 9.0 | 87.89 |
| 026 | 470 | 640 | 12.2 | 11.3 | 5.31 | 5.0 | 92.62 |
| 027 | 460 | 585 | 19.1 | 17.5 | 8.05 | 6.0 | 91.62 |
| 028 | 405 | 540 | 15.3 | 14.7 | 5.95 | 6.0 | 96.08 |
| 029 | 465 | 610 | 15.9 | 14.4 | 6.70 | 6.7 | 90.57 |
| 030 | 415 | 540 | 11.3 | 10.0 | 4.15 | 3.3 | 88.50 |
| 031 | 460 | 620 | 15.3 | 13.8 | 6.35 | 6.0 | 90.20 |
| 032 | 460 | 550 | 6.9 | 6.3 | 2.88 | 2.6 | 90.84 |
| 033 | 450 | 615 | 16.9 | 14.4 | 6.48 | 4.9 | 85.21 |
| 034 | 515 | 630 | 16.3 | 13.8 | 7.11 | 5.7 | 84.66 |
| 035 | 355 | 665 | 8.1 | 6.56 | 2.33 | 2.0 | 80.69 |
| 036 | 390 | 625 | 8.4 | 7.5 | 2.93 | 2.8 | 88.86 |
| 037 | 445 | 625 | 1.6 | 1.6 | 0.69 | 0.6 | 100.00 |
| 038 | 530 | 565 | 1.6 | 1.6 | 0.83 | 0.7 | 100.00 |
| Avg | 451.7 | 598.9 | 10.7 | 9.5 | 4.3 | 3.7 | 90.0 |
| STD | 35.40 | 46.18 | 5.95 | 5.36 | 2.42 | 2.3 | 7.52 |
| Min | 355.0 | 485.00 | 0.94 | 0.94 | 0.42 | 0.3 | 64.91 |
| Max | 530.00 | 665.00 | 25.60 | 22.50 | 9.45 | 9.0 | 100.00 |
| Median | 455.00 | 615.00 | 11.10 | 9.69 | 4.26 | 3.7 | 91.23 |

TABLE 4-continued

Summary of the data post-separation

| CRF No. | Round cells conc. In drawn volume [cell/ml] × 10⁶ | % of P.M in drawn volume | Morphology of sperm cells (%) | | | | |
|---|---|---|---|---|---|---|---|
| | | | Normal | Head defect | Middle piece defect | Tail defect | Cytoplasmic droplet |
| 001 | 0 | 95 | 14 | 70 | 2 | 40 | 4 |
| 002 | 0 | 81 | 30 | 60 | 4 | 42 | 2 |
| 003 | 0 | 95 | 20 | 82 | 2 | 30 | 4 |
| 004 | 0.077 | 71 | 14 | 76 | 4 | 18 | 0 |
| 005 | 0 | 67 | 44 | 48 | 2 | 46 | 0 |
| 006 | 0 | 65 | 46 | 40 | 4 | 46 | 4 |
| 007 | 0 | 85 | 30 | 48 | 2 | 36 | 0 |
| 008 | 0 | 96 | — | — | — | — | — |
| 009 | 0 | 85 | 26 | 58 | 0 | 50 | 0 |
| 010 | 0 | 80 | 16 | 54 | 0 | 26 | 2 |
| 011 | 0 | 47 | 40 | 48 | 4 | 26 | 0 |
| 012 | 0 | 55 | 40 | 32 | 8 | 60 | 4 |
| 013 | 0 | 74 | 15 | 75 | 0 | 40 | 0 |
| 014 | 0 | 63 | 8 | 66 | 6 | 54 | 0 |
| 016 | 0 | 100 | 42 | 52 | 2 | 28 | 0 |
| 017 | 0 | 80 | 18 | 74 | 2 | 30 | 0 |
| 018 | 0 | 100 | 26 | 66 | 2 | 34 | 0 |
| 019 | 0 | 89 | 36 | 54 | 0 | 28 | 0 |
| 021 | 0 | 100 | — | — | — | — | — |
| 022 | 0 | 83.3 | — | — | — | — | — |
| 023 | 0 | 83.3 | — | — | — | — | — |
| 024 | 0 | 100 | 36 | 46 | 4 | 44 | 0 |
| 025 | 0 | 95 | 30 | 46 | 2 | 32 | 0 |
| 026 | 0 | 95 | 54 | 28 | 8 | 12 | 0 |
| 027 | 0 | 75 | 38 | 54 | 2 | 18 | 0 |
| 028 | 0 | 100 | 14 | 72 | 2 | 32 | 0 |
| 029 | 0 | 100 | 16 | 76 | 4 | 40 | 0 |
| 030 | 0 | 80 | 30 | 62 | 6 | 32 | 0 |
| 031 | 0 | 95 | 32 | 56 | 2 | 6 | 0 |
| 032 | 0 | 90 | 20 | 76 | 0 | 48 | 2 |
| 033 | 0 | 75 | 32 | 50 | 4 | 34 | 0 |
| 034 | 0 | 80 | 36 | 48 | 0 | 26 | 0 |
| 035 | 0 | 85 | 18 | 72 | 0 | 26 | 0 |
| 036 | 0 | 95 | 10 | 78 | 2 | 46 | 0 |
| 037 | 0 | 86 | — | — | — | — | — |
| 038 | 0 | 81 | — | — | — | — | — |
| Avg | 0.0 | 84.1 | 27.7 | 58.9 | 2.7 | 34.3 | 0.7 |
| STD | 0.01 | 13.36 | 12.01 | 14.25 | 2.25 | 12.30 | 1.44 |
| Min | 0.00 | 47.37 | 8.00 | 28.00 | 0.00 | 6.00 | 0.00 |
| Max | 0.08 | 100.00 | 54.00 | 82.00 | 8.00 | 60.00 | 4.00 |
| Median | 0.00 | 85.00 | 30.00 | 57.00 | 2.00 | 33.00 | 0.00 |

1.1. Efficacy

Results of the efficacy testing of the Sperm Separation System by comparing or calculating the difference between baseline measurements and post-procedure measurements are summarized in Table 5 (statistical analysis only).

TABLE 4

Difference between baseline and post-procedure measurements

| CRF No. | Transfer rate (%) | Improvement of normal morphology (%) | Improvement of % of motile sperm cells (%) | Improvement of % PM | Decrease in round cell conc. (%) | % Yield |
|---|---|---|---|---|---|---|
| 001 | 41.5 | -4.0 | 44.6 | 79.0 | 100.0 | 125.4 |
| 002 | 32.1 | 0.0 | 53.0 | 65.0 | 100.0 | 77.7 |
| 003 | 42.8 | -8.0 | 42.7 | 74.7 | 100.0 | 102.9 |
| 004 | 56.2 | 0.0 | 45.1 | 47.4 | 66.5 | 80.1 |
| 005 | 59.7 | 10.0 | 45.6 | 26.7 | 100.0 | 49.4 |
| 006 | 47.8 | 20.0 | 34.9 | 45.0 | 100.0 | 75.4 |
| 007 | 32.3 | 4.0 | 48.2 | 60.0 | 100.0 | 50.4 |
| 008 | 37.1 | ND | 38.7 | 52.7 | 100.0 | 37.8 |
| 009 | 51.5 | 8.0 | 39.5 | 33.0 | 100.0 | 37.7 |
| 010 | 33.6 | -6.0 | 21.6 | 28.0 | 100.0 | 22.5 |
| 011 | 26.6 | 10.0 | 51.6 | 12.6 | 100.0 | 12.7 |
| 012 | 35.1 | 0.0 | 70.5 | 23.0 | 100.0 | 17.8 |
| 013 | 37.0 | 15.0 | 44.3 | 21.7 | 100.0 | 23.6 |
| 014 | 54.0 | 6.0 | 55.6 | 29.8 | 100.0 | 39.6 |
| 016 | 67.5 | 10.0 | 60.2 | 64.0 | 100.0 | 67.4 |
| 017 | 43.5 | -4.0 | 57.1 | 13.3 | 100.0 | 18.8 |
| 018 | 55.8 | -2.0 | 30.0 | 60.9 | 100.0 | 88.4 |
| 019 | 63.8 | 0.0 | 29.5 | 53.5 | 100.0 | 85.5 |

TABLE 4-continued

Difference between baseline and post-procedure measurements

| CRF No. | Transfer rate (%) | Improvement of normal morphology (%) | Improvement of % of motile sperm cells (%) | Improvement of % PM | Decrease in round cell conc. (%) | % Yield |
|---|---|---|---|---|---|---|
| 021 | 49.9 | ND | 64.6 | 68.8 | 100.0 | 56.5 |
| 022 | 25.4 | ND | 41.6 | 23.3 | 100.0 | 11.8 |
| 023 | 53.3 | ND | 55.9 | 33.3 | 100.0 | 21.6 |
| 024 | 50.4 | 6.0 | 47.9 | 52.0 | 100.0 | 48.8 |
| 025 | 66.2 | −4.0 | 41.1 | 47.0 | 100.0 | 61.4 |
| 026 | 45.9 | 6.0 | 39.7 | 71.7 | 100.0 | 99.7 |
| 027 | 80.2 | 12.0 | 45.8 | 39.0 | 100.0 | 76.4 |
| 028 | 59.3 | −4.0 | 45.0 | 36.0 | 100.0 | 47.3 |
| 029 | 47.9 | −10.0 | 42.4 | 44.0 | 100.0 | 41.3 |
| 030 | 38.9 | 2.0 | 41.1 | 48.0 | 100.0 | 45.8 |
| 031 | 66.1 | 16.0 | 48.7 | 51.0 | 100.0 | 59.3 |
| 032 | 31.6 | 2.0 | 45.2 | 55.2 | 100.0 | 37.4 |
| 033 | 58.7 | 12.0 | 35.0 | 52.0 | 100.0 | 95.7 |
| 034 | 87.9 | 24.0 | 39.7 | 46.7 | 100.0 | 94.5 |
| 035 | 97.2 | 10.0 | 43.3 | 68.3 | 100.0 | 184.6 |
| 036 | 60.4 | −6.0 | 49.7 | 64.5 | 100.0 | 73.2 |
| 037 | 26.1 | ND | 66.0 | 77.7 | 100.0 | 95.4 |
| 038 | 20.3 | ND | 36.5 | 64.3 | 100.0 | 63.0 |
| Avg | 50 | 4 | 46 | 48 | 99 | 62 |
| STD | 18 | 9 | 10 | 18 | 6 | 36 |
| Min | 20 | −10 | 22 | 13 | 67 | 12 |
| Max | 97 | 24 | 70 | 79 | 100 | 185 |
| Median | 49 | 3 | 45 | 50 | 100 | 58 |

ND = not done

Table 5 shows that a significant improvement has been achieved in all parameters with the Sperm Separation System of the present invention.

The summary of improvement per primary objective end-point is summarized in Table 6.

TABLE 6

The improvement per primary objective end-point

| End-point | Average Improvement Rate (%) | Pass Rate | 95% C.I |
|---|---|---|---|
| Sperm cell transfer rate (%) | 50 | 36/36 | 92-100 |
| Percentage of motile sperm cells | 46 | 36/36 | 92-100 |
| Percentage of sperm cells with progressive motility | 48 | 34/36 | 81-99 |
| Percentage of decrease in round cells concentration | 99 | 36/36 | 92-100 |
| Yield of separation (%) | 62 | 32/36 | 74-97 |

As shown above, cumulative improvement in all the primary end-points was proven to be statistically significant.

Significant improvement was defined as a margin of at least 20% between the baseline and the post-procedure measurement.

Success was defined as significant improvement in at least 3 out of 5 tested parameters. According to the data presented above, all 36 samples achieved a significant improvement in at least 3 out of 5 primary end-points. Furthermore, 32 out of 36 samples improved in all 5 primary end-points.

Three additional factors were analyzed by comparing baseline and post-procedure measurements, as shown in Table 7A and 7B.

Table 7: Analysis of additional factors

TABLE 7A

| | Improvement of normal morphology (%) | Total motile sperm cells in drawn volume * $10^6$ |
|---|---|---|
| Mean | 131.0% | 4.29 |
| Std. Deviation | 73.5% | 2.42 |
| Minimum | 61.5% | .42 |
| Maximum | 400.0% | 9.45 |
| Median | 111.1% | 4.26 |

As shown in Table 7, both factors have achieved significant improvement as a result of the sperm separation procedure with the Sperm Separation System of the present invention.

TABLE 7B

| | Ratio of total motile post/total motile pre % | Total no of PM sperm cells * $10^6$ pre | Total no of PM sperm cells * $10^6$ post |
|---|---|---|---|
| Mean | 44.4 | 3.57 | 3.68 |
| Std. Deviation | 15.2 | 2.44 | 2.26 |
| Minimum | 19.1 | .21 | .35 |
| Maximum | 78.4 | 8.65 | 8.98 |
| Median | 43.0 | 3.22 | 3.65 |

A paired sample T-test was conducted to detect significant differences in the total number of PM cells. The results are presented in Table 8.

TABLE 8

Difference in the total number of PM cells

| | Mean | N | Std. Deviation | Std. Error Mean |
|---|---|---|---|---|
| Total no of PM sperm cells * $10^6$ post | 3.683 | 36 | 2.2611 | .3768 |
| Total no of PM sperm cells * $10^6$ pre | 3.571 | 36 | 2.4444 | .4074 |

TABLE 8-continued

Difference in the total number of PM cells

| | Paired Differences | | | | | | | |
|---|---|---|---|---|---|---|---|---|
| | | | Std. Error | 95% Confidence Interval of the Difference | | | | Sig. (2- |
| | Mean | Std. Deviation | Mean | Lower | Upper | t | df | tailed) |
| Total no of PM sperm cells * 10^6 post − Total no of PM sperm cells * 10^6 pre | .1119 | 1.8473 | .3079 | −.5131 | .7369 | .363 | 35 | .719 |

The average improvement was found to be 0.1119, but this margin was not statistically significant (P-value>0.05).

The improvement of basic post-procedure measurements was analyzed as a proportion over the baseline evaluation, as shown in Table 9.

TABLE 9

Proportion analysis of the improvement of post-procedure measurements over baseline measurements

| | N | Mean | Std. Deviation | Std. Error | 95% Confidence Interval for Mean | | Minimum | Maximum |
|---|---|---|---|---|---|---|---|---|
| | | | | | Lower Bound | Upper Bound | | |
| Improvement of normal morphology (%) | 29 | 1.31 | .73 | .14 | 1.03 | 1.59 | .62 | 4.00 |
| Improvement of % of motile sperm cells (%) | 36 | 2.10 | .46 | .08 | 1.94 | 2.26 | 1.49 | 3.39 |
| Improvement of % PM | 36 | 2.90 | 1.81 | .30 | 2.29 | 3.51 | 1.20 | 10.71 |
| Decrease in round cell conc. (%) (0.1% error margin is introduced into equation) | 36 | 1.00 | .02 | .00 | .99 | 1.00 | .86 | 1.00 |

As shown in Table 9, for most parameters the improvement in all groups was at least 100% (i.e., equal to 1.0 in Table 9).

In the next table, table 10, the data post procedure are analyzed proportionally to the data pre procedure

TABLE 10 data post procedure analysis proportionally to the data pre procedure
Data analyzed post separation (Proportional)

| CRF No. | Transfer rate (%) | Improvement of normal morphology (%) | Improvement of % of motile sperm cells (%) | Improvement of % P.M | Decrease in round cells conc. (%) * | % Yield | Ratio of total motile post/ total motile pre % | Total no of PM sperm cells *10^6 post | Total no of PM sperm cells *10^6 pre | Total motile sperm cells in drawn volume *10^6 |
|---|---|---|---|---|---|---|---|---|---|---|
| 001 | 41.54 | 78% | 188% | 594% | >100% | 125.40 | 39.61 | 2.99 | 1.27 | 3.15 |
| 002 | 32.12 | 100% | 213% | 506% | >100% | 77 70 | 32.12 | 2.12 | 1.30 | 2.62 |
| 003 | 42.84 | 71% | 184% | 474% | >100% | 102.93 | 39.97 | 5.57 | 2.94 | 5.88 |
| 004 | 56.21 | 100% | 194% | 298% | >100% | 80.08 | 52.32 | 5.44 | 3.49 | 7.61 |

TABLE 10-continued data post procedure analysis proportionally to the data pre procedure
Data analyzed post separation (Proportional)

| CRF No. | Transfer rate (%) | Improvement of normal morphology (%) | Improvement of % of motile sperm cells (%) | Improvement of % P.M | Decrease in round cells conc. (%) * | % Yield | Ratio of total motile post/total motile pre % | Total no of PM sperm cells *10^6 post | Total no of PM sperm cells *10^6 pre | Total motile sperm cells in drawn volume *10^6 |
|---|---|---|---|---|---|---|---|---|---|---|
| 005 | 59.73 | 129% | 192% | 167% | >100% | 49.36 | 56.86 | 3.85 | 4.06 | 5.77 |
| 006 | 47.80 | 177% | 172% | 325% | >100% | 75.36 | 39.93 | 2.80 | 2.16 | 4.31 |
| 007 | 32.26 | 115% | 205% | 340% | >100% | 50.37 | 30.35 | 3.62 | 3.51 | 4.26 |
| 008 | 37.15 | no data | 184% | 222% | >100% | 37.80 | 31.56 | 3.68 | 5.25 | 3.85 |
| 009 | 51.46 | 144% | 188% | 163% | >100% | 37.70 | 43.37 | 5.42 | 7.64 | 6.38 |
| 010 | 33.60 | 73% | 150% | 154% | >100% | 22.45 | 21.81 | 2.67 | 7.96 | 3.34 |
| 011 | 26.61 | 133% | 247% | 136% | >100% | 12.66 | 23.04 | 0.77 | 2.45 | 1.62 |
| 012 | 35.08 | 100% | 339% | 172% | >100% | 17.78 | 35.08 | 1.15 | 1.90 | 2.09 |
| 013 | 37.02 | no data | 198% | 142% | >100% | 23.62 | 33.09 | 1.68 | 3.59 | 2.28 |
| 014 | 54.03 | 400% | 243% | 189% | >100% | 39.64 | 50.96 | 1.56 | 1.61 | 2.47 |
| 016 | 67.54 | 131% | 268% | 278% | >100% | 67.36 | 64.89 | 7.20 | 4.00 | 7.20 |
| 017 | 43.52 | 82% | 259% | 120% | >100% | 18.75 | 40.46 | 4.05 | 8.33 | 5.06 |
| 018 | 55.81 | 93% | 149% | 256% | >100% | 88.40 | 51.20 | 4.25 | 3.25 | 4.25 |
| 019 | 63.83 | 100% | 155% | 249% | >100% | 85.52 | 53.32 | 4.03 | 3.04 | 4.51 |
| 021 | 49.89 | no data | 282% | 320% | >100% | 56.47 | 49.89 | 0.47 | 0.29 | 0.47 |
| 022 | 25.40 | no data | 224% | 139% | >100% | 11.77 | 19.06 | 0.35 | 1.31 | 0.42 |
| 023 | 53.30 | no data | 331% | 167% | >100% | 21.62 | 42.70 | 0.50 | 0.70 | 0.60 |
| 024 | 50.38 | 120% | 203% | 208% | >100% | 48 8 | 47.52 | 7.20 | 7.27 | 7.20 |
| 025 | 66.17 | 88% | 188% | 198% | >100% | 61.40 | 58.15 | 8.98 | 7.80 | 9.45 |
| 026 | 45.87 | 113% | 175% | 412% | >100% | 99.66 | 42.49 | 5.03 | 2.88 | 5.31 |
| 027 | 80.24 | 146% | 200% | 208% | >100% | 76.41 | 73.52 | 6.04 | 3.94 | 8.05 |
| 028 | 59.30 | 78% | 188% | 156% | >100% | 47.34 | 56.97 | 5.95 | 6.69 | 5.95 |
| 029 | 47.85 | 62% | 188% | 179% | >100% | 41.31 | 43.34 | 6.70 | 8.65 | 6.70 |
| 030 | 38.92 | 107% | 187% | 250% | >100% | 45.82 | 34.44 | 3.32 | 3.86 | 4.15 |
| 031 | 66.08 | 200% | 217% | 216% | >100% | 59.34 | 59.61 | 6.03 | 4.69 | 6.35 |
| 032 | 31.65 | 111% | 199% | 259% | >100% | 37.4 | 28.75 | 2.59 | 3.48 | 2.88 |
| 033 | 58.73 | 160% | 170% | 326% | >100% | 95.72 | 50.04 | 4.86 | 2.98 | 6.48 |
| 034 | 87.90 | 300% | 188% | 240% | >100% | 94.51 | 74.42 | 5.69 | 3.18 | 7.11 |
| 035 | 97.18 | 225% | 216% | 510% | >100% | 184.60 | 78.41 | 1.98 | 0.50 | 2.33 |
| 036 | 60.40 | 63% | 227% | 310% | >100% | 73.24 | 53.67 | 2.79 | 1.68 | 2.93 |
| 037 | 26.15 | no data | 294% | 1071% | >100% | 95.35 | 26.15 | 0.59 | 0.21 | 0.69 |
| 038 | 20.34 | no data | 157% | 486% | >100% | 63 | 20.34 | 0.67 | 0.68 | 0.83 |
| Average | 49.55 | 131.01% | 210.06% | 289.94% | >100% | 61.85 | 44.43 | 3.68 | 3.57 | 4.29 |

* >100% - no round cells were found post separation

Another analysis was performed by presenting all variables as Means±SD. The average parameter values of the original semen samples were demonstrated using descriptive statistics methods. Semen sample parameters in the pre- and post-separation fractions were compared using T-tests.

The results showed that no statistical difference was obtained between the original semen sample and the inserted fraction in the frequency of any of the examined sperm cells parameters. Comparison between the pre- and post-separation fractions of the basic sperm parameters is shown in Table 11.

As shown in Table 11, on average 49.7±18.5% (range: 20-100%) of the original motile sperm cells was transferred using the Sperm Separation System of the present invention (Table 11). The transferred sperm cells exhibited significant improvement over the original semen sample in 7 of the 10 sperm cells parameters examined in this laboratory test (detailed in Table 10). The percentages of motile spermatozoa, progressively motile spermatozoa, and morphologically normal spermatozoa were significantly increased (t=−26.6, t=−15.8, t=−2.6, p≦0.01, Table 11), while the percentages of defective sperm cells, including spermatozoa with head defects and cytoplasmic droplets, as well as round form non-sperm cells, were significantly reduced post-separation (t=3.2, t=8.2, and t=7.3, respectively, p≦0.01, Table 11). When the original semen samples were subdivided into those with normal (≧50%) and low (<50%) motility, the transferred sperm cells were statistically similar in each of the examined parameters.

Note that the frequency of motile and progressively motile sperm cells in the post-separation fraction was 55% and 31% higher than in the original fraction.

TABLE 11

Comparison between pre- and post-use of the sperm separation system fractions on basic sperm parameters

| Sperm parameter | Original semen sample (M ± SD) | Pre M ± SD | Post M ± SD | t | P≦ |
|---|---|---|---|---|---|
| Volume (ml) | 1.1 ± 0.4 | 0.05 ± 0.0 | 0.05 ± 0.01 | | |
| Sperm cells concentration ([cells/ml] * 10^6) | 42.3 ± 19.6 | 42.3 ± 18.7 | 10.6 ± 5.9 | 13.7 | 0.01 |

TABLE 11-continued

Comparison between pre- and post-use of the sperm separation system fractions on basic sperm parameters

| Sperm parameter | Original semen sample (M ± SD) | Pre M ± SD | Post M ± SD | t | P≦ |
|---|---|---|---|---|---|
| Concentration of motile sperm cells (* 10^6) | 19.1 ± 8.8 | 19.1 ± 8.8 | 9.5 ± 5.3 | 10.5 | 0.01 |
| Total number of motile spermatozoa (* 10^6) | 193.1 ± 10.8 | 9.5 ± 4.4 | 4.3 ± 2.4 | 11 | 0.01 |
| Percent of motile spermatozoa (%) | 44.4 ± 8.3 | 44.4 ± 8.2 | 90.0 ± 7.5 | −26.6 | 0.01 |
| Percent of progessively motile spermatozoa (%) | 35.9 ± 14.8 | 35.9 ± 14.8 | 84.0 ± 13.6 | −15.8 | 0.01 |
| Total number of progressively motile spermatozoa (* 10^6) | 84.9 ± 13.8 | 3.5 ± 2.4 | 3.7 ± 2.3 | | N.S |
| Morphologically normal spermatozoa (%) | 22.7 ± 10.4 | 23.5 ± 10.6 | 27.7 ± 12.0 | −2.6 | 0.01 |
| Percent of head defects (%) | 63.8 ± 9.8 | 62.8 ± 9.2 | 58.9 ± 14.2 | 3.2 | 0.01 |
| Percent of middle piece defects (%) | 5.9 ± 5.3 | 5.9 ± 5.5 | 2.7 ± 2.2 | | N.S |
| Percent of tail defects (%) | 32.1 ± 14.1 | 30.6 ± 14.2 | 32.3 ± 12.3 | | N.S |
| Cytoplasmic droplet (%) | 4.5 ± 2.3 | 3.1 ± 4.7 | 0.7 ± 1.4 | 8.2 | 0.01 |
| Round non-sperm cells ([cell/ml] * 10^6) | 0.8 ± 0.6 | 0.6 ± 0.1 | 0.0 ± 0.0 | 7.3 | 0.01 |

2. Safety

No adverse event was reported or recorded throughout the procedure or during the follow-up period. Therefore, it can be concluded that the Sperm Separation System of the present invention is safe for use.

3. Discussion

The primary function of the novel Sperm Separation System is to separate motile sperm cells from the original semen sample. Three statistical analyses (cumulative, proportional, and T-test) proved the efficacy of the Sperm Separation System:

1. The results of the cumulative analysis show that all 36 semen samples achieved a significant improvement in at least 3 out of 5 primary end-points by much more than 20%. Furthermore, 32 out of 36 samples improved in all 5 primary end-points. Statistically, in at least 90% of procedures the efficacy parameter of success was shown to be as good as expected (the actual success rate was a perfect 100%).
2. The proportional analysis showed more then 100% improvement in all assessed parameters.
3. Results of the T-test analysis showed that:
    a. About 50% of inserted motile sperm cells were isolated using the Sperm Separation System.
    b. About 90% of the isolated sperm cells were motile, with 84% having progressive motility. There is strong support in the literature that sperm motility is an independent factor affecting IUI-related pregnancy (Zhao et al., 2004; Wainer et al., 2004). Moreover, Tomlinson et al. (1996) suggested that the percentage of progressively motile sperm cells is one of the most predictive parameters for JUT success.
    c. In the isolated fraction a high percent of sperm cells were morphology wise: Normal sperm morphology in general, and sperm head morphology specifically, were significantly improved post-separation. It is widely accepted that these sperm parameters are important contributors to IUI success (Guven, 2008, Grigoriou, 2005, Berkovitz et al., 1999).

The significant decrease in round non-sperm cells in the post-separation fraction compared with the original semen is also an indication of the effectiveness of the system. Bacteria and dead spermatozoa produce oxygen radicals that have a negative effect on the ability to fertilize the ovum (Boomsma, 2007). The purity of the post-separation fraction is very important for IUI or other ART. The difference in the total number of progressively motile spermatozoa before and after the separation was not statistically significant. Regarding total number of pre- and post-procedure motile spermatozoa, it has been observed that the fraction of progressively motile spermatozoa represents mainly (85%) the sperm cells population that was isolated with the Sperm Separation System. Almost all the important original population of progressively motile spermatozoa was isolated with the sperm separation system.

In view of the fact that the sperm cells parameters of isolated spermatozoa derived from sperm cells with normal and low motility were statistically similar (unpublished data), it appears that the Sperm Separation System may be used in cases of normo-zoospermia and asteno-zoospermia, a possibility that should be investigated further in larger groups. No adverse event was observed throughout the procedure, proving that the Sperm Separation System is safe for use.

The Sperm Separation System is based on the original swim-up technique: the culture medium is layered over liquefied semen for a 30-minute incubation period during which the motile sperm cells migrate from the semen layer into the culture medium. This migration step is considered to be functionally equivalent to the process by which human spermatozoa escape from the ejaculate and colonize the cervical mucus (Mortimer, 2000). Furthermore, Aitken and Clarkson (1988) discovered that the centrifugal pellet of the unselected population of human spermatozoa causes irreversible damage to the spermatozoa, which can impair, or even destroy entirely, their fertilizing ability. Therefore, sperm separation with resembles the natural process, and does not use a centrifuge, which could cause possible damage as a result of mechanical handing. In summary, the Sperm Separation System enables selective isolation based on the natural swimming ability of the sperm cells. At the end of the procedure, the medium, which initially contained no sperm cells, becomes sperm-cells enriched. The separated sperm cells population is characterized by the presence of sperm cells with progressive motility (the sperm cells with the highest potential for fertilizing the ovum) and a high percentage of normal morphology. These features demonstrate that the novel Sperm Separation System is an excellent vehicle for selectively isolating in a natural way the best sperm cell population for fertilizing the ovum using IUI or IVF.

4. Conclusions

The results from the clinical study of the Sperm Separation System demonstrated the following:
1. The Sperm Separation System is safe for use.
2. The efficacy of the Sperm Separation System was proven to produce a statistically significant improvement in the following 5 end-points:
   Sperm cell transfer rate (%)
   Percentage of motile sperm cells
   Percentage of sperm cells with progressive motility
   Percentage of decrease in round cell concentration
   Yield of separation (%)
3. The efficacy of the Sperm Separation System was proven to produce a statistically significant improvement in the first of 3 following objective factors:
   Percentage of normal morphology sperm cells
   Total number of motile sperm cells
   Total number of progressively motile sperm cells
4. The significant improvement in most semen samples was better than the expected threshold of 20%, and it applied to more than the minimal 3 out of 5 tested parameters.
5. In all 36 semen samples (100%), the procedure performed with the Sperm Separation System successfully improved the quality of the semen sample in at least 3 out of 5 tested parameters, achieving all primary end-points.

The analysis presented above demonstrates that the Sperm Separation System is safe and effective for use.

Therefore, It can be concluded that based on the statistical analysis in 100% of procedures the Sperm Separation System was found to be very effective. The system was shown to be an excellent vehicle for isolation of the progressively motile sperm cell population with the highest potential to fertilize the ovum by intra uterine insemination (IUI) or in vitro fertilization (IVF).

Example 3

A Second Laboratory Test Plan

Aim

Efficacy evaluation of the sperm separation system of the present invention's separation procedures using STL (matrix) separators of different inserted semen volumes: 0.5 versus 1.5 and/or 2.0 ml.

Experimental Steps

Assess semen sample according to the WHO guidelines
   Inclusion criteria:
Semen sample volume enables dilution up to $\leq \times 1.25$ in order to conduct the procedure
Sperm cells concentration a $\geq 10 \times 10^6$ sperm cells/ml
Motile sperm cells concentration a $\geq 5 \times 10^6$ sperm cells/ml
1. According to the original semen sample volume and sperm cells concentration, decide which combination of separators to choose: 1 separator of 0.5 ml versus 1 separator of 1.5 ml and/or 2.0 ml, as many as the volume allows for extra separators. Conduct a dilution, if necessary.
2. Follow the procedure as detailed in example 2 and perform sperm separation techniques using the separators (in the chosen combination in line 1) with minimal time interval between the separators. The incubation period: 30 min.
3. Draw the medium out from the separators post incubation.
4. Assess the sperm cells in the uppermost layer post procedures and record the results.

Results:

A total of 19 samples of semen were collected between Mar. 3, 2010 and Mar. 24, 2010. 2 samples were excluded due to low sperm cells concentration (repetition 2) or due to high dilution performed (repetition 14).

Table 1 presents basic information and the assessment of the original semen samples.

TABLE 1 basic information and the assessment of the original semen samples (A + B)

A. donations 1-10

| Repetition no. | | 1 | 2 | 3 | 4 | 5 | 6 | 7 | 8 | 9 | 10 |
|---|---|---|---|---|---|---|---|---|---|---|---|
| Date | | 3.3.10 | 3.3.10 | 3.3.10 | 3.3.10 | 9.3.10 | 9.3.10 | 10.3.10 | 10.3.10 | 10.3.10 | 16.3.10 |
| Donor code | | OK | GR | TM | YM | TM | NK | NN | YH | YM | SG |
| Abstaining duration (days) | | 3 | 4 | 3 | 5 | 3 | 7 | 3 | 3.5 | 3 | 3 |
| Original Semen sample volume (ml) | | 6.5 | 4.0 | 3.0 | 3.0 | 2.3 | 3.5 | 3.0 | 3.8 | 3.0 | 2.6 |
| Semen sample pH | | >8.0 | 8.0 | 7.8 | 7.6 | 7.8 | 7.8 | 8.0 | 8.0 | 7.8 | 8.0 |
| Semen sample viscosity (N-normal, L-low, M-medium, H-high) | | l | n | n | n | n | n | h | m | n | n |
| Original sperm cells conc. ($\times 10^6$/ml) | | 17.2 | 11.3 | 43.0 | 76.0 | 39.7 | 64.0 | 66.0 | 51.0 | 42.0 | 43.0 |
| Semen sample dilution | Y/N | N | N | Y | Y | N | Y | Y | Y | Y | Y |
| | Final volume (ml) | — | — | 4.5 | 7.0 | — | 4.5 | 4.8 | 4.5 | 4.0 | 4.5 |
| | Dilution factor | — | — | 1.5 | 2.3 | — | 1.3 | 1.6 | 1.2 | 1.3 | 1.7 |
| Semen assessment | Sperm cells conc. ($\times 10^6$/ml) | 17.2 | 11.3 | 28.8 | 34.7 | 39.7 | 47.8 | 39.1 | 39.1 | 56.3 | 29.7 |
| | Motile sperm cells conc. ($\times 10^6$/ml) | 8.1 | 3.8 | 15.3 | 18.4 | 15.9 | 19.1 | 17.8 | 13.8 | 22.2 | 17.2 |
| | Round cells conc. ($\times 10^6$/ml) | 0.4 | 0.1 | 0.5 | 0.9 | 0.2 | 0.4 | 0.2 | 0.1 | 0.5 | 0.6 |

TABLE 1-continued basic information and the assessment of the original semen samples (A + B)

| | | | | | | | | | | |
|---|---|---|---|---|---|---|---|---|---|---|
| | Progressively motile sperm cells (%) | 10.0 | 61.9 | 52.6 | 60.0 | 71.4 | 60.0 | 56.0 | 56.0 | 60.0 |
| | Grade A motility (%) | 70.0 | 95.0 | 100 | 100 | 100 | 100 | 92.0 | 100 | 100 | 100 |
| | Sperm cells vitality (%) | 77.0 | 56.0 | 66.0 | 86.0 | 83.0 | 66.0 | 60.0 | 70.0 | 66.0 | 73.0 |
| | Sperm cells normal morphology (%) | 28.0 | 20.0 | 34.0 | 24.0 | 24.0 | 16.0 | 14.0 | 20.0 | 12.0 | 14.0 |
| | Head defects (%) | 68.0 | 80.0 | 62.0 | 72.0 | 68.0 | 72.0 | 66.0 | 68.0 | 82.0 | 84.0 |
| | Neck middle piece defects (%) | 4.0 | 8.0 | 0 | 2.0 | 4.0 | 6.0 | 12.0 | 14.0 | 6.0 | 4.0 |
| | Tail defects (%) | 8.0 | 40.0 | 12.0 | 50.0 | 22.0 | 20.0 | 46.0 | 10.0 | 20.0 | 34.0 |
| | Cytoplasmic droplets (%) | 0 | 2.0 | 2.0 | 0 | 0 | 0 | 0 | 0 | 2.0 | 2.0 |

B. donations 11-19

| | | | | | | | | | | |
|---|---|---|---|---|---|---|---|---|---|---|
| | Repetition no. | 11 | 12 | 13 | 14 | 15 | 16 | 17 | 18 | 19 |
| | Date | 16.3.10 | 16.3.10 | 17.3.10 | 17.3.10 | 22.3.10 | 23.3.10 | 24.3.10 | 24.3.10 | 24.3.10 |
| | Donor code | YM | YH | TM | NK | NN | NK | TM | YG | YH |
| | Abstaining duration (days) | 3 | 3 | 3 | 3 | 3 | 3 | 3 | 3 | 4 |
| | Original semen sample volume (ml) | 3.4 | 3.8 | 2.0 | 2.3 | 2.0 | 2.5 | 3 | 5.8 | 4.5 |
| | Semen sample pH | 7.8 | 8.0 | 8.0 | 7.8 | 7.8 | 7.8 | 7.6 | 7.8 | 7.8 |
| | Semen sample viscosity (N-normal, L-low, M-medium, H-high) | n | l | n | n | h | n | n | l | n |
| | Original sperm cells conc. ($\times 10^6$/ml) | 43.0 | 43.8 | 20.6 | 91.9 | 61.5 | 34.0 | 56.0 | 19.4 | 47.8 |
| Semen sample dilution | Y/N | Y | N | N | Y | Y | Y | Y | N | N |
| | Final volume (ml) | 5.0 | — | — | 8.0 | 2.5 | 3.0 | 4.5 | — | — |
| | Dilution factor | 1.5 | — | — | 3.5 | 1.3 | 1.2 | 1.5 | — | — |
| Semen assessment | Sperm cells conc. ($\times 10^6$/ml) | 40.9 | 43.8 | 20.6 | 39.7 | 49.1 | 27.2 | 27.4 | 19.4 | 47.8 |
| | Motile sperm cells conc. ($\times 10^6$/ml) | 16.3 | 16.3 | 9.4 | 15.9 | 18.1 | 14.4 | 16.6 | 11.3 | 18.8 |
| | Round cells conc. ($\times 10^6$/ml) | 0.7 | 0.9 | 0.2 | 0.2 | 1.2 | 0.4 | 0.08 | 1.0 | 1.4 |
| | Progressively motile sperm cells (%) | 80.0 | 65.0 | 36.0 | 60. | 60.0 | 20.0 | 90.48 | 35.0 | 25.0 |
| | Grade A motility (%) | 100 | 100 | 76.0 | 100 | 100 | 80.0 | 95.0 | 95.0 | 100 |
| | Sperm cells vitality (%) | 77.0 | 70.0 | N.D (N.D. - not done) | 54.0 | 51.0 | 71.0 | 82.0 | 85.0 | 55.0 |
| | Sperm cells normal morphology (%) | 14.0 | 10.0 | N.D. | 14.0 | 12.0 | 10.0 | 2.0 | 18.0 | 18.0 |

TABLE 1-continued basic information and the assessment of the original semen samples (A + B)

| | | | | | | | | | |
|---|---|---|---|---|---|---|---|---|---|
| Head defects (%) | 84.0 | 80.0 | | 70.0 | 70.0 | 88.0 | 90.0 | 68.0 | 70.0 |
| Neck & middle piece defects (%) | 4.0 | 12.0 | | 4.0 | 12.0 | 2.0 | 8.0 | 8.0 | 6.0 |
| Tail defects (%) | 16.0 | 18.0 | | 30.0 | 24.0 | 42.0 | 26.0 | 30.0 | 20.0 |
| Cytoplasmic droplets (%) | 0 | 0 | | 0 | 0 | 0 | 0 | 0 | 0 |

TABLE 2

Pre- and post-procedure semen assessment and calculations

| repetition | seperator volume (microL) | % motile sperm cells pre | % motile sperm cells post | % PM sperm cells pre | % PM sperm cells post | round cells concentration pre | round cells concentration post | Total motile sperm cells in drawn volume | Total PM sperm cells in drawn volume |
|---|---|---|---|---|---|---|---|---|---|
| 1 | 500 | 47.27 | 100.00 | 10.00 | 25.00 | 3.91E+05 | 0.00E+00 | 3.16E+06 | 7.89E+05 |
|  | 2000 | 47.27 | 68.75 | 10.00 | 25.00 | 3.91E+05 | 0.00E+00 | 2.29E+06 | 5.71E+05 |
|  | 1500 | 47.27 | 94.12 | 10.00 | 25.00 | 3.91E+05 | 0.00E+00 | 3.18E+06 | 7.94E+05 |
|  | 2000 | 47.27 | 87.50 | 10.00 | 25.00 | 3.91E+05 | 0.00E+00 | 2.21E+06 | 5.52E+05 |
| 3 | 1500 | 53.26 | 93.75 | 52.63 | 75.00 | 4.69E+05 | 0.00E+00 | 4.36E+06 | 3.27E+06 |
|  | 2000 | 53.26 | 96.67 | 52.63 | 30.00 | 4.69E+05 | 7.81E+04 | 3.72E+06 | 2.97E+06 |
|  | 500 | 53.26 | 90.32 | 52.63 | 75.00 | 4.69E+05 | 0.00E+00 | 4.38E+06 | 3.28E+06 |
| 4 | 2000 | 53.15 | 87.13 | 60.00 | 71.43 | 9.38E+05 | 7.81E+04 | 5.79E+06 | 4.14E+06 |
|  | 2000 | 53.15 | 76.47 | 60.00 | 80.00 | 9.38E+05 | 0.00E+00 | 4.23E+06 | 3.38E+00 |
|  | 1500 | 53.15 | 82.61 | 60.00 | 55.00 | 9.38E+05 | 0.00E+00 | 3.09E+00 | 2.62E+06 |
|  | 500 | 53.15 | 75.00 | 60.00 | 75.00 | 9.38E+05 | 0.00E+00 | 3.68E+06 | 2.76E+06 |
| 5 | 500 | 40.16 | 78.95 | 60.00 | 65.00 | 2.34E+05 | 0.00E+00 | 1.97E+06 | 1.28E+06 |
|  | 1500 | 40.16 | 97.22 | 60.00 | 65.00 | 2.34E+05 | 0.00E+00 | 5.63E+06 | 3.66E+06 |
| 6 | 2000 | 39.87 | 82.26 | 71.43 | 80.00 | 3.91E+05 | 0.00E+00 | 9.40E+06 | 7.52E+06 |
|  | 1500 | 39.87 | 88.57 | 71.43 | 80.00 | 3.91E+05 | 0.00E+00 | 5.13E+06 | 4.11E+06 |
|  | 500 | 39.87 | 91.49 | 71.43 | 80.00 | 3.91E+05 | 0.00E+00 | 6.79E+06 | 5.43E+06 |
| 7 | 2000 | 45.60 | 88.24 | 60.00 | 65.00 | 2.03E+06 | 0.00E+00 | 5.11E+06 | 3.32E+06 |
|  | 2000 | 45.60 | 87.80 | 60.00 | 85.71 | 2.03E+06 | 0.00E+00 | 6.47E+06 | 5.54E+06 |
|  | 500 | 45.60 | 83.33 | 60.00 | 60.00 | 2.03E+06 | 0.00E+00 | 1.63E+06 | 9.75E+05 |
| 8 | 2000 | 35.20 | 94.44 | 56.00 | 80.00 | 1.02E+06 | 0.00E+00 | 3.35E+06 | 2.68E+06 |
|  | 1500 | 35.10 | 97.37 | 56.00 | 70.00 | 1.02E+06 | 0.00E+00 | 6.82E+06 | 4.75E+06 |
|  | 500 | 35.20 | 86.36 | 56.00 | 80.00 | 1.02E+06 | 0.00E+00 | 3.33E+06 | 2.66E+06 |
| 9 | 1500 | 39.44 | 92.00 | 56.00 | 76.19 | 5.47E+05 | 0.00E+00 | 8.84E+06 | 6.74E+06 |
|  | 1500 | 39.44 | 90.48 | 56.00 | 80.95 | 5.47E+05 | 1.56E+05 | 6.77E+06 | 5.48E+06 |
|  | 500 | 39.44 | 92.00 | 56.00 | 70.00 | 5.47E+05 | 0.00E+00 | 3.88E+06 | 2.72E+06 |
| 10 | 2000 | 57.89 | 88.00 | 60.00 | 80.00 | 6.25E+05 | 0.00E+00 | 3.95E+06 | 3.16E+06 |
|  | 1500 | 57.89 | 84.21 | 60.00 | 75.00 | 6.25E+05 | 0.00E+00 | 5.95E+06 | 4.46E+06 |
|  | 500 | 57.89 | 89.13 | 60.00 | 70.00 | 6.25E+05 | 0.00E+00 | 6.60E+06 | 4.62E+06 |
| 11 | 2000 | 39.69 | 93.33 | 80.00 | 90.00 | 7.03E+05 | 0.00E+00 | 2.43E+06 | 2.19E+06 |
|  | 2000 | 39.69 | 65.38 | 80.00 | 85.00 | 7.03E+05 | 0.00E+00 | 3.19E+06 | 2.71E+06 |
|  | 500 | 39.69 | 93.33 | 50.00 | 85.00 | 7.03E+05 | 7.81E+04 | 2.21E+06 | 1.88E+06 |
| 12 | 1500 | 37.14 | 88.00 | 65.00 | 75.00 | 8.59E+05 | 0.00E+00 | 3.64E+06 | 2.73E+06 |
|  | 1500 | 37.14 | 95.00 | 65.00 | 80.00 | 8.59E+05 | 0.00E+00 | 6.06E+06 | 4.85E+06 |
|  | 500 | 37.14 | 88.00 | 65.00 | 75.00 | 8.59E+05 | 0.00E+00 | 3.30E+06 | 2.43E+06 |
| 13 | 1500 | 45.45 | 86.96 | 36.00 | 65.00 | 2.34E+05 | 0.00E+00 | 3.81E+06 | 2.48E+06 |
|  | 500 | 45.45 | 100.00 | 36.00 | 75.00 | 2.34E+05 | 0.00E+00 | 2.19E+06 | 1.64E+06 |
| 15 | 1500 | 36.91 | 89.66 | 60.00 | 80.00 | 1.17E+06 | 0.00E+00 | 4.18E+06 | 3.35E+06 |
|  | 500 | 36.94 | 92.59 | 60.00 | 70.00 | 1.17E+06 | 0.00E+00 | 3.75E+06 | 2.63E+06 |
| 16 | 2000 | 52.87 | 100.00 | 20.00 | 85.00 | 3.91E+05 | 0.00E+00 | 8.32E+06 | 7.07E+06 |
|  | 500 | 52.87 | 100.00 | 20.00 | 75.00 | 3.91E+05 | 0.00E+00 | 4.94E+06 | 3.71E+06 |
| 17 | 2000 | 58.24 | 82.00 | 90.48 | 85.00 | 7.51E+04 | 0.00E+00 | 7.43E+06 | 6.32E+06 |
|  | 1500 | 58.24 | 100.00 | 90.48 | 75.00 | 7.81E+04 | 0.00E+00 | 5.40E+06 | 4.05E+06 |
|  | 500 | 58.24 | 95.45 | 90.48 | 90.00 | 7.81E+04 | 0.00E+00 | 1.94E+06 | 1.74E+06 |

TABLE 2-continued

Pre- and post-procedure semen assessment and calculations

| repetition | seperator volume (microL) | % motile sperm cells pre | % motile sperm cells post | % PM sperm cells pre | % PM sperm cells post | round cells concentration pre | round cells concentration post | Total motile sperm cells in drawn volume | Total PM sperm cells in drawn volume |
|---|---|---|---|---|---|---|---|---|---|
| 18 | 2000 | 58.06 | 92.86 | 35.00 | 85.00 | 1.02E+06 | 0.00E+00 | 2.36E+06 | 2.00E+06 |
|  | 2000 | 58.06 | 88.24 | 35.00 | 55.00 | 1.02E+06 | 7.31E+04 | 2.65E+06 | 1.46E+06 |
|  | 500 | 58.06 | 86.67 | 35.00 | 75.00 | 1.02E+06 | 0.00E+00 | 2.07E+06 | 1.55E+06 |
| 19 | 1500 | 39.22 | 90.91 | 25.00 | 80.00 | 1.41E+06 | 0.00E+00 | 3.31E+06 | 2.65E+06 |
|  | 1500 | 39.22 | 85.71 | 25.00 | 90.00 | 1.41E+06 | 0.00E+00 | 2.95E+06 | 2.66E+06 |
|  | 500 | 39.22 | 95.45 | 25.00 | 85.00 | 1.41E+06 | 0.00E+00 | 3.51E+06 | 2.98E+06 |

TABLE 3

Pre- and post-procedure parameters proportional calculations for parameter changes in the different separators

| repetition | separator volume (microL) | the proportional change of % motile sperm cells pre/post | the proportional change of % PM sperm cells pre/post | the proportional decrease in round cells conc. (%) * |
|---|---|---|---|---|
| 1 | 500 | 211.54% | 250.00% | >100% |
|  | 2000 | 145.43% | 250.00% | >100% |
|  | 1500 | 199.10% | 250.00% | >100% |
|  | 2000 | 185.10% | 250.00% | >100% |
| 3 | 1500 | 176.02% | 142.50% | >100% |
|  | 2000 | 181.50% | 152.00% | >100% |
|  | 500 | 169.59% | 142.50% | >100% |
| 4 | 2000 | 164.02% | 119.05% | >100% |
|  | 2000 | 143.87% | 133.33% | 83.33% |
|  | 1500 | 155.42% | 141.67% | >100% |
|  | 500 | 141.10% | 125.00% | 91.67% |
| 5 | 500 | 196.59% | 108.33% | >100% |
|  | 1500 | 242.10% | 108.33% | >100% |
| 6 | 2000 | 206.32% | 112.00% | >100% |
|  | 1500 | 222.15% | 112.00% | >100% |
|  | 500 | 229.47% | 112.00% | >100% |
| 7 | 2000 | 193.50% | 108.33% | >100% |
|  | 2000 | 192.55% | 142.86% | >100% |
|  | 500 | 182.75% | 100.00% | >100% |
| 8 | 2000 | 268.31% | 142.86% | >100% |
|  | 1500 | 276.61% | 125.00% | >100% |
|  | 500 | 245.35% | 142.86% | >100% |
| 9 | 1500 | 233.24% | 136.05% | >100% |
|  | 1500 | 229.38% | 144.56% | >100% |
|  | 500 | 233.24% | 125.00% | >100% |
| 10 | 2000 | 152.00% | 133.33% | >100% |
|  | 1500 | 145.45% | 125.00% | 71.43% |
|  | 500 | 153.95% | 116.67% | >100% |
| 11 | 2000 | 235.13% | 112.50% | >100% |
|  | 2000 | 164.72% | 106.25% | >100% |
|  | 500 | 235.13% | 106.25% | >100% |
| 12 | 1500 | 236.92% | 115.38% | >100% |
|  | 1500 | 255.77% | 123.08% | >100% |
|  | 500 | 236.92% | 115.38% | 88.89% |
| 13 | 1500 | 191.30% | 180.56% | >100% |
|  | 500 | 220.00% | 208.33% | >100% |
| 15 | 1500 | 242.69% | 133.33% | >100% |
|  | 500 | 250.64% | 116.67% | >100% |
| 16 | 2000 | 189.13% | 425.00% | >100% |
|  | 500 | 189.13% | 375.00% | >100% |
| 17 | 2000 | 140.79% | 93.94% | >100% |
|  | 1500 | 171.70% | 82.89% | >100% |
|  | 500 | 163.89% | 99.47% | >100% |
| 18 | 2000 | 159.92% | 242.86% | >100% |
|  | 2000 | 151.96% | 157.14% | 92.31% |
|  | 500 | 149.26% | 214.29% | >100% |
| 19 | 1500 | 231.82% | 320.00% | >100% |
|  | 1500 | 218.57% | 360.00% | >100% |
|  | 500 | 243.41% | 340.00% | >100% |

* >100% - no round cells were found post separation

TABLE 4

Pre- and post-procedure vitality and morphology assessment and proportional calculations for parameter changes in the different separators

| repetition | separator volume (microL) | Normal morphology pre (%) | Normal morphology post (%) | the proportional change | Head defects pre (%) | Head defects post (%) | the proportional change | Sperm cells vitality pre (%) | Sperm cells vitality post (%) | the proportional change |
|---|---|---|---|---|---|---|---|---|---|---|
| 1 | 500 | 28.00 | 32.00 | 114.29% | 68.00 | 62.00 | 8.82% | 77.00 | 54.00 | 70.13% |
|  | 2000 | 28.00 | 42.00 | 150.00% | 68.00 | 50.00 | 26.47% | 77.00 | 50.00 | 64.94% |
|  | 1500 | 28.00 | 38.00 | 135.71% | 68.00 | 58.00 | 14.71% | 77.00 | 75.00 | 97.40% |
|  | 2000 | 28.00 | 42.00 | 150.00% | 68.00 | 66.00 | 2.94% | 77.00 | 60.00 | 77.92% |
| 3 | 1500 | 34.00 | 28.00 | 82.35% | 62.00 | 62.00 | 0.00% | 66.00 | 80.00 | 121.21% |
|  | 2000 | 34.00 | 32.00 | 94.12% | 62.00 | 64.00 | −3.23% | 66.00 | 73.00 | 110.61% |
|  | 500 | 34.00 | 30.00 | 88.24% | 62.00 | 60.00 | 3.23% | 66.00 | 80.00 | 121.21% |

TABLE 4-continued

Pre- and post-procedure vitality and morphology assessment and proportional calculations for parameter changes in the different separators

| repetition | separator volume (microL) | Normal morphology pre (%) | Normal morphology post (%) | the proportional change | Head defects pre (%) | Head defects post (%) | the proportional change | Sperm cells vitality pre (%) | Sperm cells vitality post (%) | the proportional change |
|---|---|---|---|---|---|---|---|---|---|---|
| 4 | 2000 | 24.00 | 26.00 | 108.33% | 70.00 | 70.00 | 0.00% | 86.00 | 87.00 | 101.16% |
|   | 2000 | 24.00 | 32.00 | 133.33% | 70.00 | 58.00 | 17.14% | 86.00 | 87.00 | 101.16% |
|   | 1500 | 24.00 | 26.00 | 108.33% | 70.00 | 72.00 | −2.86% | 86.00 | 91.00 | 105.81% |
|   | 500 | 24.00 | *** |  | 70.00 |  |  | 86.00 |  |  |
| 5 | 500 | 24.00 | 26.00 | 108.33% | 68.00 | 70.00 | −2.94% | 83.00 | 90.00 | 108.43% |
|   | 1500 | 14.00 | 34.00 | 141.67% | 68.00 | 64.00 | 5.88% | 83.00 | 95.00 | 114.46% |
| 6 | 2000 | 16.00 | 38.00 | 237.50% | 72.00 | 46.00 | 36.11% | 66.00 | 80.00 | 121.21% |
|   | 1500 | 16.00 | 24.00 | 150.00% | 72.00 | 70.00 | 2.78% | 66.00 | 83.00 | 125.76% |
|   | 500 | 16.00 | 36.00 | 225.00% | 72.00 | 54.00 | 25.00% | 66.00 | 88.00 | 133.33% |
| 7 | 2000 | 14.00 | 24.00 | 171.43% | 66.00 | 70.00 | −6.06% | 40.00 | 80.00 | 200.00% |
|   | 2000 | 14.00 | 24.00 | 171.43% | 66.00 | 66.00 | 0.00% | 40.00 | 74.00 | 185.00% |
|   | 500 | 14.00 | ** |  | 66.00 |  |  | 40.00 |  |  |
| 8 | 2000 | 10.00 | 54.00 | 540.00% | 68.00 | 46.00 | 32.35% | 70.00 | 72.00 | 102.86% |
|   | 1500 | 10.00 | 40.00 | 400.00% | 68.00 | 64.00 | 5.88% | 70.00 | 82.00 | 117.14% |
|   | 500 | 10.00 | 24.00 | 240.00% | 68.00 | 72.00 | −5.88% | 70.00 | 70.00 | 100.00% |
| 9 | 1500 | 12.00 | 24.00 | 200.00% | 82.00 | 78.00 | 4.88% | 66.00 | 87.00 | 131.82% |
|   | 1500 | 12.00 | 24.00 | 200.00% | 82.00 | 72.00 | 12.20% | 66.00 | 91.00 | 137.88% |
|   | 500 | 12.00 | 16.00 | 133.33% | 82.00 | 82.00 | 0.00% | 66.00 | 89.00 | 134.85% |
| 10 | 2000 | 24.00 | 40.00 | 166.67% | 86.00 | 56.00 | 34.88% | 73.00 | 83.00 | 113.70% |
|   | 1500 | 24.00 | 32.00 | 133.33% | 86.00 | 58.00 | 32.56% | 73.00 | 80.00 | 109.59% |
|   | 500 | 24.00 | 23.00 | 95.83% | 86.00 | 68.00 | 20.93% | 73.00 | 91.00 | 124.66% |
| 11 | 2000 | 14.00 | 88.00 | 628.57% | 84.00 | 52.00 | 38.10% | 77.00 | 95.00 | 123.38% |
|   | 2000 | 14.00 | 42.00 | 300.00% | 84.00 | 58.00 | 30.95% | 77.00 | 67.00 | 87.01% |
|   | 500 | 14.00 | 28.00 | 200.00% | 84.00 | 66.00 | 21.43% | 77.00 | 95.00 | 123.38% |
| 12 | 1500 | 12.00 | 50.00 | 416.67% | 80.00 | 50.00 | 37.50% | 70.00 | 91.00 | 130.00% |
|   | 1500 | 12.00 | 46.00 | 383.33% | 80.00 | 52.00 | 35.00% | 70.00 | 85.00 | 121.43% |
|   | 500 | 12.00 | 40.00 | 333.33% | 80.00 | 58.00 | 27.50% | 70.00 | 71.00 | 101.43% |
| 13 (The values of "pre" were taken from repetition 3 (same donor) | 1500 | 34.00 | 24.00 | 70.59% | 62.00 | 66.00 | −6.45% | 66.00 | 82.00 | 124.24% |
|   | 500 | 34.00 | ** |  | 62.00 |  |  | 66.00 |  |  |
| 15 | 1500 | 12.00 | 26.00 | 216.67% | 70.00 | 64.00 | 8.57% | 51.00 | 77.00 | 150.98% |
|   | 500 | 12.00 | 38.00 | 316.67% | 70.00 | 52.00 | 25.71% | 51.00 | 80.00 | 156.86% |
| 16 | 2000 | 10.00 | 18.00 | 180.00% | 88.00 | 74.00 | 15.91% | 71.00 | 75.00 | 105.63% |
|   | 500 | 10.00 | 26.00 | 260.00% | 88.00 | 70.00 | 20.45% | 71.00 | 93.00 | 130.99% |
| 17 | 2000 | 2 | 22 | 1100.00% | 90 | 76 | 15.56% | 82 | 81 | 98.78% |
|   | 1500 | 2 | 22 | 1100.00% | 90 | 76 | 15.56% | 82 | 90 | 109.76% |
|   | 500 | 2 | 20 | 1000.00% | 90 | 76 | 15.56% | 82 | 71 | 86.59% |
| 18 | 2000 | 18 | 28 | 155.56% | 68 | 64 | 5.88% | 85 | 75 | 88.24% |
|   | 2000 | 18 | 36 | 200.00% | 68 | 60 | 11.76% | 85 | 60 | 70.59% |
|   | 500 | 18 | 30 | 166.67% | 65 | 70 | −2.94% | 85 | 80 | 94.12% |
| 19 | 1500 | 18 | 42 | 233.33% | 70 | 56 | 20.00% | 55 | 60 | 109.09% |
|   | 1500 | 18 | 30 | 166.67% | 70 | 60 | 14.29% | 55 | 82 | 149.09% |
|   | 500 | 18 | 24 | 133.33% | 70 | 64 | 8.57% | 55 | 90 | 163.64% |

** not done (few sperm cells on the slide)

*** not done (technical reason

TABLE 5

The average proportional changes of the different separators

A. parameters regarding the sperm cells motility and the round cells concentration

| separator volume (microL) | No. of repetitions | Avg proportional change of motile sperm cells pre/post (%) | Avg proportional change of PM sperm cells pre/post | Avg proportional change in round cells conc. (%) | Avg % motile sperm cells post | Avg % PM sperm cells post |
|---|---|---|---|---|---|---|
| 500 | n = 17 | 203.1 ± 37.3 | 164.6 ± 85.0 | 94.17 ± 24.0 | 90.5 ± 7.1 | 72.4 ± 14.3 |
| 1500 | n = 16 | 214.3 ± 37.3 | 162.5 ± 78.7 | 93.79 ± 24.8 | 91.0 ± 5.0 | 73.6 ± 14.5 |
| 2000 | n = 16 | 179.6 ± 35.1 | 167.6 ± 85.9 | 81.42 ± 40.0 | 86.2 ± 9.5 | 72.3 ± 20.4 |

B. parameters regarding sperm cells morphology

| separator vol (ml) | no. of repetitions | Avg normal morphology pre (%) | Avg normal morphology post (%) | the avg proportional change | Avg head defects pre (%) | Avg head defects post (%) | the avg proportinal change |
|---|---|---|---|---|---|---|---|
| 0.5 | n = 14 | 18.00 ± 8.8 | 28.07 ± 6.8 | 243.93% ± 231.9 | 73.76 ± 9.2 | 66.0 ± 8.3 | 11.82% ± 12.0 |
| 1.5 | n = 16 | 18.25 ± 9.0 | 31.88 ± 8.8 | 258.67% ± 249.2 | 73.75 ± 8.4 | 63.88 ± 8.2 | 12.53% ± 13.2 |
| 2.0 | n = 16 | 18.25 ± 8.2 | 36.75 ± 16.6 | 280.43% ± 264.7 | 73.63 ± 9.2 | 61.00 ± 9.4 | 16.17% ± 15.3 |
| average | | 18.17 | 32.23 | 261.01% | 73.71 | 63.63 | 13.51% |

1. All separators show remarkable improvement of the average % motile, % progressively motile pre- and post-procedure.
2. The decrease in the round cells concentration is prominent in all separators.
3. The average % of motile and progressively motile sperm cells post procedure is very high in all the separators.
4. All separators show remarkable improvement of normal morphology post procedure.
5. All separators show decrease in head defects post procedure.

TABLE 6

Calculation of total motile and total progressively motile sperm cells per 0.6 and 1.0 ml of drawn post procedure medium in the different

| Repetition | Dilution factor | Motile sperm concentration pre procedure | Total inserted semen sample volume (ml) | Total volume drawn from all separators (microL) (As detailed in table 5) | Total motile sperm cells per procedure of all separators | Total PM sperm cells per procedure of all separators | Total motile sperm cells per 0.6 ml drawn | Total PM sperm cells per 0.6 ml drawn | Total motile sperm cells per 1.0 ml drawn | Total PM sperm cells per 1.0 ml drawn |
|---|---|---|---|---|---|---|---|---|---|---|
| 1 | — | 8.13E+06 | 4 | 1805 | 8.62E+06 | 2.15E+06 | 2.86E+06 | 7.16E+05 | 4.77E+06 | 1.19E+35 |
| 2 excluded | — | 3.75E+06 | 4 | 1460 | 1.22E+06 | 5.51E+05 | 5.00E+05 | 2.26E+05 | 8.33E+05 | 3.77E+05 |
| 3 | 1.5 | 1.53E+07 | 4 | 1375 | 1.25E+07 | 9.52E+06 | 5.43E+06 | 4.16E+06 | 9.35E+06 | 6.93E+05 |
| 4 | 2.33 | 1.84E+07 | 4 | 1600 | 1.10E+07 | 3.76E+06 | 4.12E+06 | 3.29E+06 | 6.37E+06 | 5.48E+06 |
| 5 | — | 1.59E+07 | 2 | 935 | 7.60E+06 | 4.94E+06 | 4.88E+06 | 3.17E+06 | 8.13E+06 | 5.28E+06 |
| 6 | 1.29 | 1.91E+07 | 4 | 1120 | 2.13E+07 | 1.71E+07 | 1.14E+07 | 9.14E+06 | 1.90E+07 | 1.52E+07 |
| 7 | 1.60 | 1.78E+07 | 4.5 | 1640 | 1.32E+07 | 9.84E+06 | 4.83E+06 | 3.60E+06 | 8.05E+06 | 6.00E+05 |
| 8 | 1.18 | 1.38E+07 | 4 | 1780 | 1.35E+07 | 1.01E+07 | 4.55E+06 | 3.41E+06 | 7.58E+06 | 5.68E+06 |
| 9 | 1.33 | 2.22E+07 | 3.5 | 1725 | 1.95E+07 | 1.49E+07 | 6.78E+06 | 5.19E+06 | 1.13E+07 | 8.66E+05 |
| 10 | 1.73 | 1.72E+07 | 4 | 1685 | 1.65E+07 | 1.22E+07 | 5.88E+06 | 4.36E+06 | 9.79E+06 | 7.27E+05 |
| 11 | 1.47 | 1.72E+07 | 4.5 | 1660 | 7.83E+06 | 5.77E+06 | 2.83E+06 | 2.45E+06 | 4.71E+06 | 4.08E+05 |
| 12 | — | 1.63E+07 | 3.5 | 1520 | 1.30E+07 | 1.01E+07 | 5.13E+06 | 3.97E+06 | 8.55E+06 | 6.61E+05 |
| 13 | — | 9.38E+06 | 2 | 1110 | 6.00E+06 | 4.12E+06 | 3.24E+06 | 2.23E+06 | 5.41E+06 | 3.71E+05 |
| 14A excluded | 3.48 | 1.25E+07 | 4 | 1725 | 6.51E+06 | 5.17E+06 | 2.26E+06 | 1.80E+06 | 3.77E+06 | 3.60E+05 |
| 14B excluded | 3.48 | 1.25E+07 | 4 | 1770 | 5.23E+06 | 4.01E+06 | 1.77E+06 | 1.36E+06 | 2.96E+06 | 2.27E+06 |

TABLE 6-continued

Calculation of total motile and total progressively motile sperm cells per 0.6 and 1.0 ml of drawn post procedure medium in the different

| Repetition | Dilution factor | Motile sperm concentration pre procedure | Total inserted semen sample volume (ml) | Total volume drawn from all separators (microL) (As detailed in table 5) | Total motile sperm cells per procedure of all separators | Total PM sperm cells per procedure of all separators | Total motile sperm cells per 0.6 ml drawn | Total PM sperm cells per 0.6 ml drawn | Total motile sperm cells per 1.0 ml drawn | Total PM sperm cells per 1.0 ml drawn |
|---|---|---|---|---|---|---|---|---|---|---|
| 15 | 1.25 | 1.81E+07 | 2 | 995 | 7.93E+06 | 5.97E+06 | 4.78E+06 | 3.60E+06 | 7.97E+06 | 6.00E+06 |
| 16 | 1.2 | 1.44E+07 | 2.5 | 1170 | 1.33E+07 | 1.08E+07 | 6.80E+06 | 5.53E+06 | 1.13E+07 | 9.21E+06 |
| 17 | 1.5 | 1.66E+07 | 4 | 1415 | 1.48E+07 | 1.21E+07 | 6.26E+06 | 5.13E+06 | 1.04E+07 | 8.56E+06 |
| 18 | — | 1.13E+07 | 4.5 | 1655 | 7.08E+06 | 5.01E+06 | 2.57E+06 | 1.82E+06 | 4.28E+06 | 3.03E+06 |
| 19 | — | 1.88E+07 | 3.5 | 1590 | 9.78E+06 | 8.29E+06 | 3.69E+06 | 3 13E+06 | 6.15E+06 | 5.22E+06 |

Since there is no known "golden standard" for end-product of sperm preparation procedure, a literature review was done together with an internal survey among professional people within the fertility arena, in order to develop a baseline threshold standard for the outcome of sperm preparation for IUI procedures.

A suggested threshold of $4 \times 10^6$ total motile sperm cells as an outcome of sperm preparation of original semen sample was chosen as a minimal threshold parameter for sperm preparation system.

Figure 6:
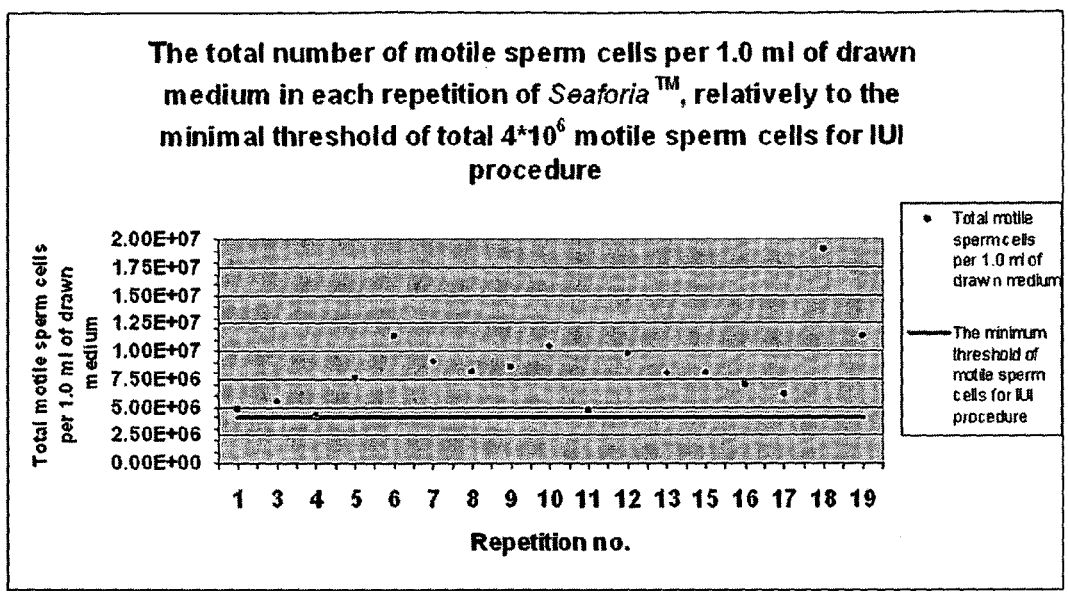
FIG. 6 shows a clinical results of using the sperm separation system as provided by the present invention. in the figure a graphic illustration of the total no. of motile sperm cells per 1 ml post separation by the sperm separation system of the present invention is provided.

According to the threshold of $4 \times 10^6$ total motile sperm cells as an outcome of sperm preparation of original semen sample, 17/17 (100%) repetitions (#1, 3-13 and 15-19, see column "total motile sperm cells per 1.0 ml drawn medium post) passed the threshold, see FIG. 6.

In the figure, the total no. of motile sperm cells in drawn medium (calculated per 1 ml) post sperm separation system procedure (using the entire original semen sample) in the 17 repetitions, relatively to a minimal threshold of $4 \times 10^6$ motile sperm cells for IUI procedure is presented.

The next section presents a comparison of basic sperm cells parameters pre- and post-using the sperm separation system fractions using separators with different volumes of inserted semen sample.

TABLE 7 t-test ($p \leq 0.01$ means significant difference) comparison of basic sperm cells parameters pre- and post-procedure of the sperm separation system fractions using separators with different volumes of inserted semen sample

| Sperm parameter | Pre M±SD | Post M±SD | t | $p \leq$ |
|---|---|---|---|---|
| A. for separator of 0.5 ml inserted semen sample ||||| 
| Percent of motile spermatozoa (%), n = 17 | 45.85 ± 8.2 | 90.48 ± 7.1 | 17.11 | 0.01 |
| Percent of progressively motile spermatozoa (%), n = 17 | 52.80 ± 21.2 | 72.4 ± 14.3 | 4.31 | 0.01 |
| Total number of progressively motile spermatozoa ($\times 10^6$), n = 17 | 4.3 ± 2.1 | 2.5 ± 1.3 | 3.39 | 0.01 |
| Total number of motile spermatozoa ($\times 10^6$), n = 17 | 7.93 ± 1.8 | 3.49 ± 1.5 | 9.26 | 0.01 |
| Morphologically normal spermatozoa (%), n = 14 | 18.0 ± 8.8 | 28.1 ± 6.8 | 4.32 | 0.01 |
| Percent of head defects (%), n = 14 | 73.8 ± 9.2 | 66.0 ± 8.3 | 3.74 | 0.01 |
| Round non-sperm cells ([cell/ml] $\times 10^6$), n = 17 | 0.7 ± 0.5 | 0.005 ± 0.02 | 6.06 | 0.01 |
| B. for separator of 1.5 ml inserted semen sample |||||
| Percent of motile spermatozoa (%), n = 16 | 43.69 ± 7.8 | 91.04 ± 5.0 | 19.58 | 0.01 |
| Percent of progressively motile spermatozoa (%), n = 16 | 53.03 ± 19.9 | 73.57 ± 14.5 | 4.40 | 0.01 |
| Total number of progressively motile spermatozoa ($\times 10^6$), n = 16 | 13.70 ± 5.9 | 3.67 ± 1.4 | 7.91 | 0.01 |
| Total number of motile spermatozoa ($\times 10^6$), n = 16 | 25.00 ± 5.7 | 4.95 ± 1.7 | 15.18 | 0.01 |
| Morphologically normal spermatozoa (%), n = 16 | 18.3 ± 9.0 | 31.9 ± 8.8 | 4.13 | 0.01 |
| Percent of head defects (%), n = 16 | 73.8 ± 8.4 | 63.9 ± 8.2 | 3.70 | 0.01 |
| Round non-sperm cells ([cell/ml] $\times 10^6$), n = 16 | 0.8 ± 0.6 | 0.01 ± 0.03 | 6.59 | 0.01 |

TABLE 7-continued t-test ($p \leq 0.01$ means significant difference) comparison of basic sperm cells parameters pre- and post-procedure of the sperm separation system fractions using separators with different volumes of inserted semen sample

| Sperm parameter | Pre M±SD | Post M±SD | t | $p \leq$ |
|---|---|---|---|---|
| C. for separator of 2.0 ml inserted semen sample | | | | |
| Percent of motile spermatozoa (%), n = 16 | 49.06 ± 7.6 | 86.19 ± 9.5 | 13.36 | 0.01 |
| Percent of progressively motile spermatozoa (%), n = 16 | 52.53 ± 24.3 | 72.32 ± 20.4 | 4.57 | 0.01 |
| Total number of progressively motile spermatozoa ($\times 10^6$), n = 16 | 17.10 ± 9.3 | 3.47 ± 2.1 | 6.43 | 0.01 |
| Total number of motile spermatozoa ($\times 10^6$), n = 16 | 30.20 ± 7.3 | 4.55 ± 2.3 | 16.47 | 0.01 |
| Morphologically normal spermatozoa (%), n = 16 | 18.25 ± 8.2 | 36.8 ± 16.6 | 4.04 | 0.01 |
| Percent of head defects (%), n = 16 | 73.6 ± 9.2 | 61.0 ± 9.4 | 4.19 | 0.01 |
| Round non-sperm cells ([cell/ml] $\times 10^6$), n = 16 | 0.8 ± 0.6 | 0.01 ± 0.03 | 5.83 | 0.01 |

Figure 7A:
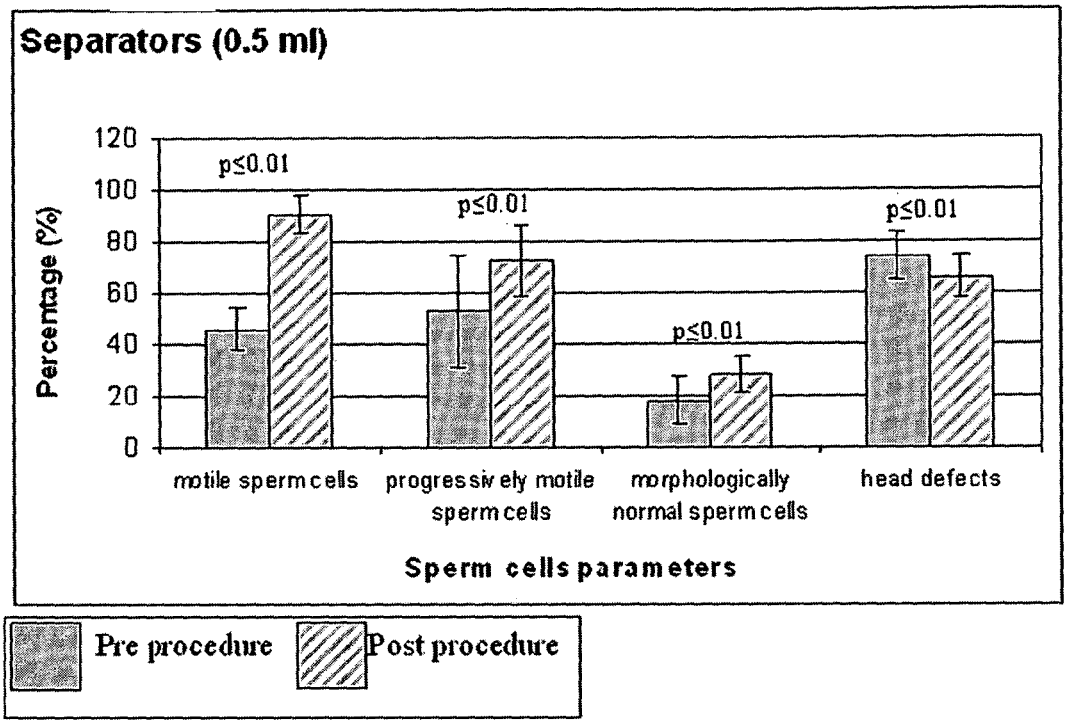
FIGS. 7A and 7B show a graphic illustration of semen parameters pre- and post separation procedure using separator adapted for 0.5 ml inserted semen sample.
Figure 7B:
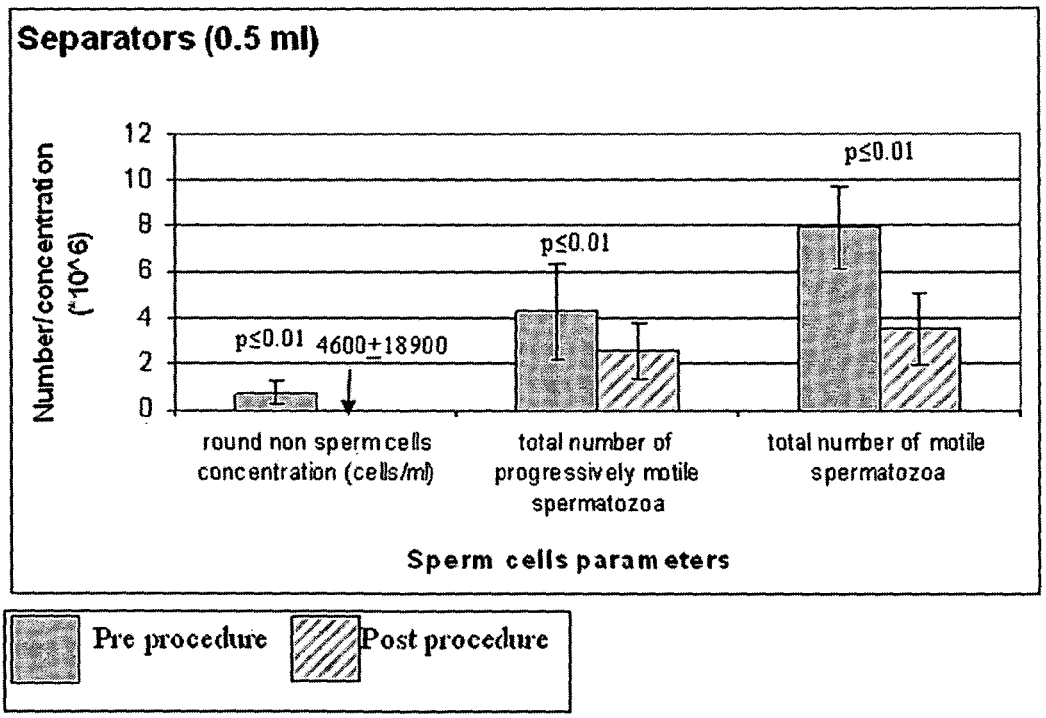

Reference is now made to FIGS. 7A and B which illustrate Semen parameters pre- and post procedure of the sperm separation system using separator of 0.5 ml inserted semen sample (n=17).

Figure 8A:
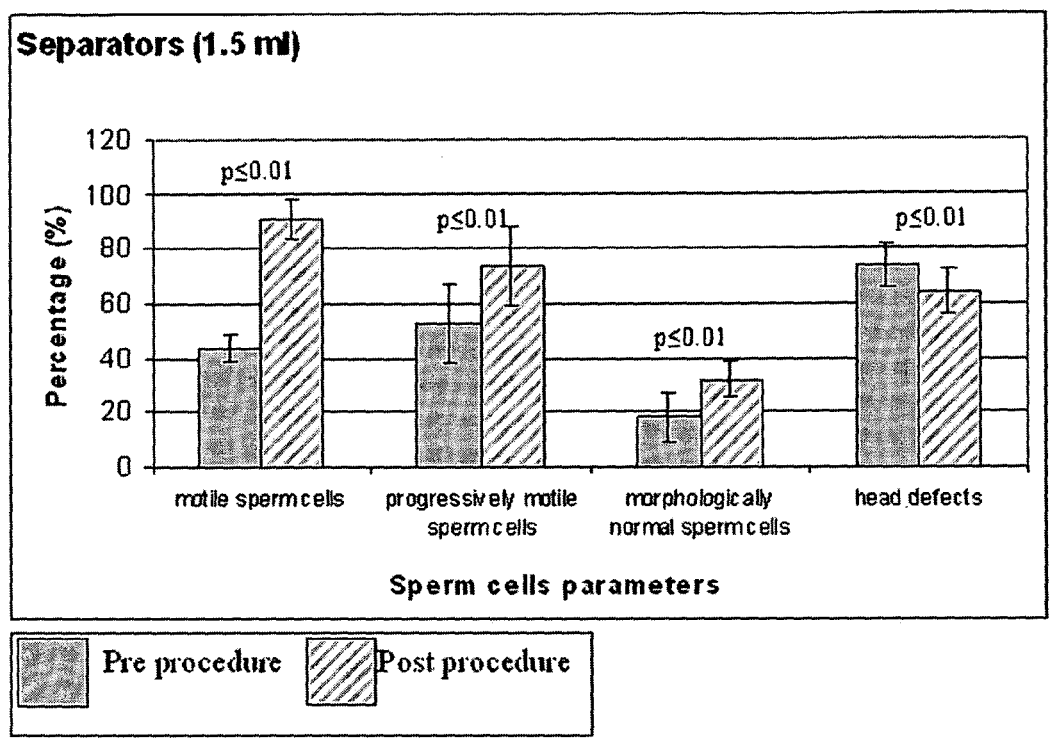
FIGS. 8A and 8B shows a graphic illustration of semen parameters pre- and post separation procedure using separator adapted for 1.5 ml inserted semen sample.
Figure 8B:
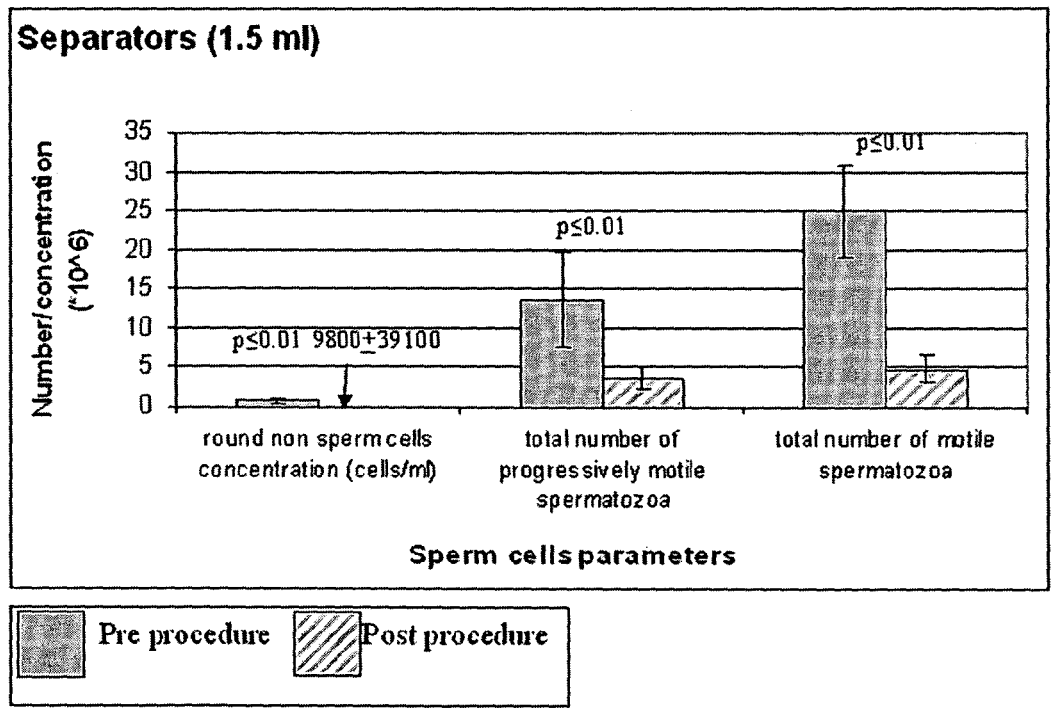

Reference is now made to FIGS. 8A and 8B which illustrates Semen parameters pre- and post procedure of the sperm separation system using separator of 1.5 ml inserted semen sample (n=16).

Figure 9A:
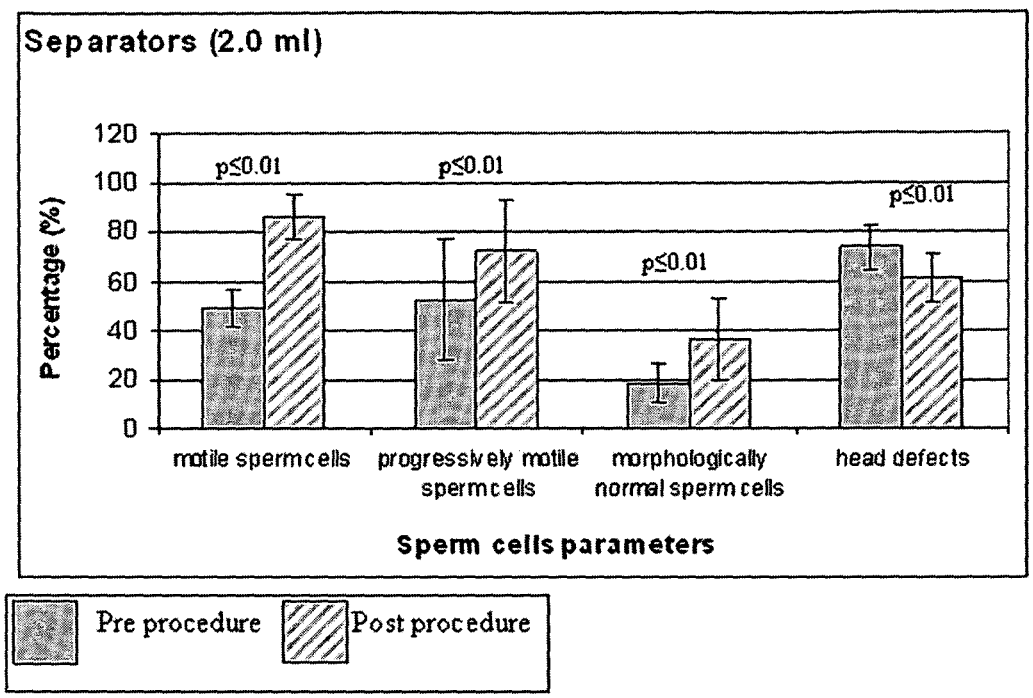
FIGS. 9A and 9B shows a graphic illustration of semen parameters pre- and post separation procedure using separator adapted for 2 ml inserted semen sample.
Figure 9B:
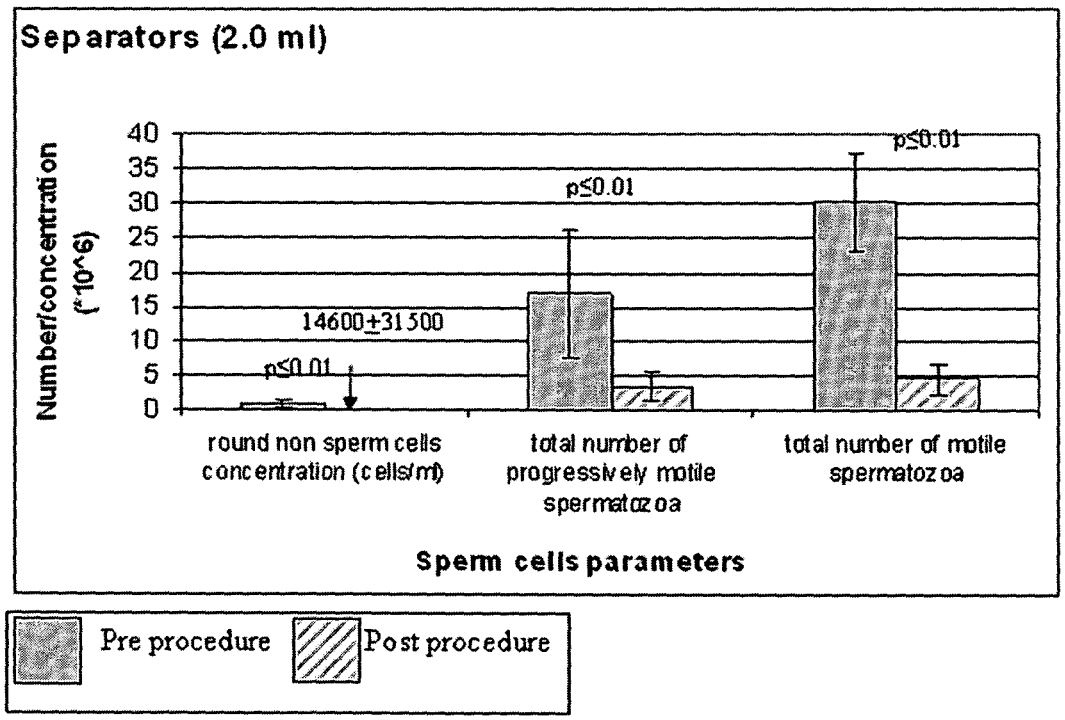

Reference is now made to FIGS. 9A and 9B which illustrate Semen parameters pre- and post use of the sperm separation system using separator of 2 ml inserted semen sample (n=16).

In order to see whether there is a significant difference in the parameters tested, we used the paired T test (the pre and post parameters were taken from the same samples). The basic assumption was that there is no difference between the pre and post parameters and the alternative assumption was that there is a difference. The statistic T value indicates how extreme the difference is in the pre and post's mean. The P value is the indication for rejecting our basic assumption, if it is smaller than 0.01, it means that the probability of getting a result such as the one we got, assuming the basic assumption is true is lower than 1 percent and that is why we reject the basic assumption.

The following Preliminary results can be summarized:

1. Calculating the total numbers of motile and progressively motile (PM) sperm cells pre and post procedure takes into account the volume of the inserted semen samples. Therefore, the separators of 1.5 and 2.0 ml are in a different starting point compared to 0.5 ml. Nevertheless, there is a significant difference between the total PM-pre and the total PM-post in all separators.

2. All the separators show significant difference of the values of % PM, % motile (trend of higher percentages in the post procedure fractions) and round cells concentration pre-post (trend of decrease in the round cells concentration in the post procedure fractions).

3. There is a significant improvement of the morphologically normal spermatozoa post procedure in comparison to the pre procedure fraction. At the same time there is a significant decrease in the percentage of head defects post procedure relatively to the pre procedure population.

The entire repetitions summary according to the chosen scoring:

| Repetition | Separator 0.5 ml | Separator 1.5 ml | Separator 2.0 ml | |
|---|---|---|---|---|
| 1 | 1 | 1 | 1 | 1 |
| 3 | 1 | 1 | 1 | |
| 4 | 1 | 1 | 1 | 1 |
| 5 | 1 | 1 | | |
| 6 | 1 | 1 | 1 | |
| 7 | 1 | | 1 | 1 |
| 8 | 1 | 1 | 1 | |
| 9 | 1 | 1 | 1 | |
| 10 | 1 | 1 | 1 | |
| 11 | 1 | | 1 | 1 |
| 12 | 1 | 1 | 1 | |
| 13 | 1 | 1 | | |
| 15 | 1 | 1 | | |
| 16 | 1 | | 1 | |
| 17 | 1 | 1 | 1 | |
| 18 | 1 | | 1 | 1 |
| 19 | 1 | 1 | 1 | |
| summary | 17/17 | 16/16 | 16/16 | |

All the different separators show 100% efficacy.

SUMMARY

Using separators with different semen volumes showed that there is no difference in the procedures results, concerning separation of the best sperm cells population regarding characters of motility and morphology (having the highest potential to reach the ovum and to fertilize it), leaving most of round non sperm cells behind.

Therefore all the separators are suitable for use in the Sperm Separation System as vehicles for sperm preparation before IUI or IVF procedures.

According to the threshold of $4 \times 10^6$ total motile sperm cells as an outcome of sperm preparation out of original semen sample, 17/17 (100%) repetitions passed the threshold.

REFERENCES

Aitken R J, Skakkebaek N E, Roman S D (2006): Male reproductive health and the environment. MJA 185: 414-415

Aitken R J, Clarkson J S (1988): Significance of reactive oxygen species and antioxidants in defining the efficacy of sperm preparation techniques. J Androl 9: 367-376

Allamaneni S S R, Agarwal A, Rama S, Ranganathan P, Sharma R K (2005): Comparative study on density gradients and swim-up preparation techniques utilizing neat and cryopreserved spermatozoa. Asian J Androl 7: 86-92

Ashkani H, Akbari A, Heydari S T (2006): Epidemiology of depression among infertile and fertile couples in Shiraz, southern Iran. Indian J Med Sci 60: 399-406.

Bartoov B, Berkovitz A, Eltes F, Kogosowski A, Menezo Y and Barak Y (2002): Real-time fine morphology of motile human sperm cells is associated with IVF-ICSI outcome. J Androl 23: 1-8

Bayasgalan G, Naranbat D, Radnaabazar J, Lhagvasuren T, Rowe P J (2004): Male infertility: risk factors in Mongolian men. Asian J Androl 6: 305-311

Bensdorp A J, Cohlen B J, Heineman M J, Vandekerckhove P (2007): Intra-uterine insemination for male subfertility. Cochrane Database Syst Rev: CD000360

Berkovitz A, Eltes F, Soffer Y, Zabludovsky N, Beyth Y, Farhi J, Levran D, Bartoov B (1999): ART success and in vivo sperm cell selection depend on the ultramorphological status of spermatozoa. Andrologia. 31:1-8

Boomsma C M, Heineman M J, Cohlen B J, Farquhar C (2007): Semen preparation techniques for intrauterine insemination. Cochrane Database Syst Rev: CD004507

Crazzolara S, Wunder D, Nageli E, Bodmer C, Graf S, Birkhauser M H (2007): Semen parameters in a fertile Swiss population. Swiss Med WKLY 137: 166-172

DSouza U J, DSouza V M, Narayana K (2004): Is today's male population really less fertile? Declining semen quality—A global phenomenon? Indian J Med Sci 58: 305-306

Evenson D P, Jost L K, Marshall D, Zinaman M J, Clegg E, Purvis K, de Angelis P and Claussen O P (1999): Utility of the sperm chromatin structure assay as a diagnostic and prognostic tool in the human fertility clinic. Hum Reprod 14: 1039-1049

Grigoriou O, Pantos K, Makrakis E, Hassiakos D, Konidaris S, Creatsas G (2005): Impact of isolated teratozoospermia on the outcome of intrauterine insemination. Fertil Steril 83: 773-775

Guven S, Gunalp G S, Tekin Y (2008): Factors influencing pregnancy rates in intrauterine insemination cycles. J Reprod Med 53: 257-265

Guzick D S, Overstreet J W, Factor-Litvak P, Brazil C K, Nakajima S T, Coutifaris C, Carson S A, Cisneros P, Steinkampf M P, Hill J A, Xu D and Vogel D L (2001): Sperm morphology, motility and concentration in fertile and infertile men. N Engl J Med 345: 1388-1393

Henkel R R and Schill W B (2003): Sperm preparation for ART. Reprod Biol Endoc 1:108-130

Jensen M S, Mabeck L M, Toft G, Thulstrup A M, Bonde J P (2005): Lower sperm counts following prenatal tobacco exposure. Hum Reprod 20: 2559-2566

Jose-Miller A B, Boyden J W (2007): Infertility. Americ Family Physic 75: 849-856

Keck C, Gerber-Schafer C, Wilhelm C, Vogelgesang D, Breckwoldt M (1997): Intrauterine insemination for treatment of male infertility. Int J Androl 20: 55-64

Mahadevan M and Baker G (1984): Assessment and preparation of semen for in vitro fertilization. In: Clinical In Vitro Fertilization Edited by: Wood C, Trounson A. Springer-Verlag, Berlin; 83-97

Mehta R H, Makwana S, Ranga G M, Srinivasan R J, Virk S S (2006): Prevalences of oligozoospermia and azoospermia in male partners of infertile couples from different parts of India. Asian J Androl 8: 89-93

Mortimer D (2000): Sperm preparation methods. J Androl 21:357-366

Nallella K P, Sharma R K, Aziz N, Aqarwal A (2006): Significance of sperm characteristics in the evaluation of male infertility. Fertil Steril 85: 629-634

Qadan L R, Ahmed A A, Kapila K A, Hassan N A, Kodaj J A, Pathan S K (2007): Male infertility in Kuwait. Etiologic and therapeutic aspects. Saudi Med J 28: 96-99

Sallmen M, Liesivouri J, Taskinen H, Lindbohm M L, Antilla A, Aalto L, Hemminki (2003): Time to pregnancy among the wives of Finnish greenhouse workers. Scand J Work Environ Health 29: 85-93

Sharp R M (2000): Lifestyle and environmental contribution to male infertility. Brit Med Bull 56:630-642

Sokol R Z, Kraft P, Fowler I M, Mamet R, Kim E, Berhance K T (2006): Exposure to environmental Ozone alters semen quality. Environ Health Perspect 114: 360-365

Su T J, Chen H F, Chen Y C, Yang Y S, Hung YT (2006): Factors related to meaning of life in Taiwanese woman treated with in vitro fertilization. J Formos Med Assoc 105: 404-413

Swai B, Poggensee G, Mtweve S, Krantz I (2006): Female genital schistosomiasis as an evidence of neglected cause for reproductive ill-health: a retrospective histopathological study from Tanzania. BMC Infect Dis 23: 134-141

Swan S H, Brazil C, Drobnis E Z, Liu F, Kruse R L, Hatch M, Redmon J B, Wang C, Overstreet J W and The study for future families research group (2003): Geographic differences in semen quality of fertile U.S. males. Environ Health Perspect 111: 414-420

The ESHRE Capri workshop group (2009): Intrauterine insemination. Hum Reprod Update. Epub ahead of print Thonneau P, Marchand S, Tallec A, Ferial M L, Ducot B, Lansac J, Lopes P, Tabaste J M, Spira A (1991): Incidence and main causes of infertility in a resident population of three French regions (1988-1989). Hum Reprod 6: 811-816

Tomlinson M J, Amissah-Arthur J B, Thompson K A, Kasraie J L, Bentick B (1996): Prognostic indicators for intrauterine insemination (IUI): statistical model for IUI success. Hum Reprod 11: 1892-1896

Toppari J, Haavisto A M, Alanen M (2002): Changes in male reproductive health and effects of endocrine disruptors in Scandinavian countries. Cad Saude Publica 18:413-420

Travison T G, Araujo A B, O'Donnell A B, Kupelian V, McKinlay J B (2007): A population-level decline in serum testosterone levels in American men. J Clinic Endoc Metab 92: 196-202

Wainer R, Albert M, Dorion A, Bailly M, Bergere M, Lombroso R, Gombault M, Selva J (2004): Influence of the number of motile spermatozoa inseminated and of their morphology on the success of intrauterine insemination. Hum Reprod 19: 2060-2065

Wolff H (1995): The biologic significance of white blood cells in semen. Fertil Steril 63: 1143-1157

World Health Organization (1999): WHO laboratory manual for the examination of human semen and sperm-cervical mucus interaction. Cambridge: Cambridge University Press.

Zhao Y, Vlahos N, Wyncott D, Petrella C, Garcia J, Zacur H, Wallach E E (2004): Impact of semen characteristics on the success of intrauterine insemination. J assist Reprod Genet 21: 143-148.

Cartz, L., Nondestructive Testing, ASM International, Materials Park, Ohio, 1995, pp. 135-136.

Tugrul, A. B., Capillarity Effect Analysis for Alternative Liquid Penetrant Chemicals, NDT & E International, Volume 30 Number 1, Published by Elsevier Science Ltd., Oxford England, February 1997, pp. 19-23.

What is claimed is:

1. A naturally based Sperm Separation System (SSS) for separation of at least a portion of sperm cell populations (SCP) characterized by (i) motility in a range between about 5 μm/s to about 15 μm/s at 37°; (ii) slow progressive motility in a range between about 15 μm/s at 37° to about 25 μm/s at 37°; (iii) rapid progressive motility of at least 25 μm/s at 37° and 20 μm/s at 20°; (iv) at least 90% motile sperm cells, having an average of at least 32% normal morphology; or any combination thereof, within an original semen sample, such that an enriched SCP sample is obtained; said SSS comprising:
   a. a sperm separation device, comprising:
      i. at least one first chamber adapted to contain at least a portion of said original semen sample; said first chamber is characterized by pre-determined 3D shape and volume, V; said first chamber is bounded by a rim such that said original semen sample is kept below said rim; wherein said rim is crenellated shaped; and,
      ii. at least one second chamber in physical communication with said first chamber and said rim; said second chamber is characterized by pre-determined 3D shape and volume, $V_1$, wherein said $V_1$ is substantially smaller than or equal to V;
         said second chamber is adapted to reside said enriched SCP sample; said enriched SCP sample comprising at least a portion of said SCP crossing through the crenellations in said crenellated shaped rim such that said separation of said SCP from said original semen sample is obtained and said enriched SCP sample is provided;
   b. incubation means, adapted to socket at least one of said cell separation device and to homogeneously thermoregulate the temperature within the same;
   wherein said pre-determined 3D shape of said first and second chambers and said crenellations in said rim enables at least one of the following is held true:
      i. efficacy of said SSS is at least 95%;
      ii. the total number of motile CSP separated into said second chamber is at least $4*10^6$ as examined with phase contrast or light microscopes, when said original semen sample is a NORMAL sample as defined by WHO 1999 Appendix IA clause 2.5 and comprises at least $5*10^6$ [motile CSP/ml];
      iii. the concentration of motile CSP separated into said second chamber is at least $4*10^6$ [cell/ml] as measured with phase contrast or light microscopes when the concentration of motile CSP in said original semen sample is at least $5*10^6$ [motile sperm cell/ml];
      iv. the total number of progressive motile CSP separated into said second chamber is at least $2*10^6$ as measured with phase contrast or light microscopes, when said original semen sample comprises at least $2.5*10^6$ [progressive motile CSP/ml];
      v. the average percentage of CSP having normal morphology in said enriched sample is at least 32% in as measured with phase contrast or microscopes when said original semen sample comprises an average of at least 18% CSP having normal morphology.

2. The SSS according to claim 1, wherein at least one of the following is being held true (a) said $V_1$ equals to said V; (b) said first chamber is dimpled-shaped; (c) said first chamber and said second are co-axial such that said second chamber is peripheral and circumferentially encircles said first chamber; (d) said first chamber and said second are in a side by side configuration; (e) said first chamber and said second are in a pile configuration; (f) said pre-determined 3D shape of said first chamber is characterized by a cross sectional area of circular and is defined by radius R; (g) said pre-determined 3D shape of said second chamber is characterized by a cross sectional area of circular and is defined by radius $R^1$; (h) said pre-determined 3D shape of said first chamber is characterized by a cross sectional area having n ribs where n is an integer higher than or equals to 3, or any combination thereof; (i) said pre-determined 3D shape of said second chamber is characterized by a cross sectional area having n ribs where n is an integer higher than or equals to 3, or any combination thereof and any combination thereof.

3. The SSS according to claim 1, wherein at least one of the following is being held true (a) said SSS increases the efficacy of said separation and the enrichment of said SCP within said enriched SCP sample such that said increase is greater than the sum of said pre-determined 3D shape of said first and second chamber effectiveness and said crenellations in said rim effectiveness; (b) said SCP are adapted to cross through or above the crenellations in said crenellated shaped rim into said second chamber upon introduction of a support medium into either said first chamber and/or said second chamber such that said support medium is in liquid communication with at least a portion of said original semen sample.

4. The SSS according to claim 1, wherein at least one of the following is held true:
   i. the total number of motile CSP separated into said second chamber is at least $4*10^6$ as examined with phase contrast or light microscopes, when said original semen sample is a NORMAL sample as defined by WHO 1999 Appendix IA clause 2.5;
   ii. the concentration of motile CSP separated into said second chamber is at least $4*10^6$ [cell/ml] as measured with phase contrast or light microscopes when said original semen sample is a NORMAL sample as defined by WHO 1999 Appendix IA clause 2.5;
   iii. the total number of progressive motile CSP separated into $^s$said second chamber is at least $2*10^6$ as measured with phase contrast or light microscopes, when said original semen sample is a NORMAL sample as defined by WHO 1999 Appendix IA clause 2.5;
   iv. the average percentage of CSP having normal morphology in said enriched sample is at least 32%, as measured with phase contrast or light microscopes when said original semen sample is a NORMAL sample as defined by WHO 1999 Appendix IA clause 2.5;
   v. the average % of motile sperm cells in said enriched sample in said second chamber is increased by an average of at least 210% relatively to the average % motile sperm cells in said original semen sample, as measured with phase contrast or light microscopes;
   vi. the % of progressive motile CSP in said enriched sample in said second chamber is increased by an average of at least 290% relatively to the average % progressive motile CSP in said original semen sample, as measured with phase contrast or light microscopes;
   vii. the % of CSP having normal morphology in said enriched sample in said second chamber is increased by an average of at least 260% relatively to the average % of CSP having normal morphology in said original semen sample, as measured with phase contrast or light microscopes;
   viii. the average % of motile sperm cells isolated into said enriched sample is multiplied by at least 2.0 relatively to the average % motile sperm cells in said original semen sample as measured with phase contrast or light microscopes;

ix. the average % of progressive motile sperm cells isolated into said second chamber is multiplied by at least 1.4 relatively to the average % of progressive motile sperm cells in said original semen sample as measured with phase contrast or light microscopes;

x. the % of decrease said CSP having abnormal round cells morphology isolated into said second chamber is about 99% as measured with phase contrast or light microscopes.

5. The SSS according to claim 1, wherein at least one of the following is being held true (a) said isolated sperm cells are depleted of round non motile cells selected from group of round non sperm cells, immature sperm cells, dead sperm cells or any combination thereof; (b) the average yield of separation is higher than 58%, relative to said original semen sample before said separation; (c) at least an average of at least 70% of said isolated sperm cells are progressively motile.

6. The SSS according to claim 1, wherein said SSS is further adapted to perform assays selected from a group consisting of: a sperm cells concentration assay, a semen pH assay, a leukocytes concentration threshold assay, a sperm cells motility assay, a sperm cells morphology assay, a semen volume assay, a viscosity assay and a turbidity assay; further wherein said assays is adapted to facilitate diagnosis of at least one sexually transmitted disease (STD) selected from a group consisting of: syphilis, gonorrhea, Candida, human papiloma virus (HPV), mycoplasma, ureaplasma, human immunodeficiency virus (HIV), Chlamydia, herpes simplex virus, Hepatitis B, Trichomonas and Hepatitis C.

7. The SSS according to claim 1, wherein said SSS is sealed such that no contamination of the environment outside said cartridge is performed.

8. The SSS according to claim 1, additionally comprising a reagent adapted to, upon contact with said original sperm sample, to yield a reaction and/or a colored compound indicating (i) existence; or, (ii) concentration of a component in said original or enriched sample; (iii) a result of said at least one assay; further wherein said reagent is selected from a group consisting of cell support medium, labeling compounds, markers, peptide, color-changeable pad or any combination thereof.

9. The SSS according to claim 1, wherein said original sample is selected from a group consisting of: a semen sample, a vaginal secretion sample, a vaginal cell sample, a blood sample, a urine sample, a saliva sample, a lymph sample or any combination thereof.

10. The SSS according to claim 1, further comprising at least one selected from a group consisting of (a) at least one sensor adapted to interface with said cartridge to facilitate said at least one assay; (b) a control adapted to perform at least one action selected from a group consisting of: (i) receive a reading from said at least one sensor, said sensor is in communication with said cartridge; (ii) analyze said reading; (iii) analysis readings received based upon said at least one of said assays; and (iv) output said analysis of said original sperm sample; any combination thereof.

11. The SSS according to claim 1, wherein said cell separation device is socketed in said incubation means for a pre-determined period of about 10 minutes to about 60 minutes; further wherein said incubation means are adapted to thermoregulate the temperature within said cell separation device to a temperature of about 30 Celsius degrees and about 39 Celsius degrees.

12. The SSS according to claim 1, wherein said cell separation device additionally comprising a cover; said cover comprises at least two orifices; said orifices are adapted to enable guided entry or aspiration of fluids aspiration means or actuators to either said first central chamber or said second chamber; further wherein said actuators are selected from a group consisting of needle, cannula, pipette, syringe any positive displacement system such as a peristaltic pump or any combination thereof.

13. The SSS according to claim 1, wherein said cell separation device additionally comprising at least one orifice adapted to enable entry or aspiration of fluids aspiration means or actuators either to said first central chamber or said second chamber; further wherein said actuators are selected from a group consisting of needle, cannula, pipette, syringe any positive displacement system such as a peristaltic pump or any combination thereof.

14. The SSS according to claim 1, further adapted to assess at least one selected from a group consisting of (a) motility of sperm cells and/or isolate motile sperm within an enriched semen sample for assisting fertility or diagnose sperm cells; (b) motility of sperm cells in said original or enriched semen sample, and/or isolate motile sperm of said original or enriched semen sample for fertility treatments selected from a group consisting of: intra uterine insemination (MI), vaginal insemination, and in-vitro fertilization (IVF).

15. The SSS according to claim 1, wherein at least one of the following is being held true (a) said rim is configured with specific surface roughness or serration to facilitate required surface tension, surface energy, capillary forces capabilities for specific sample/reagent combination; (b) said support medium is selected from a group consisting of Ringer's solution, Hartmann's solution, Saline Hyaluronic acid, Phosphor buffered saline (PBS) or any other sperm preparation or separation or washing medium adapted to facilitate said separation; (c) said first central chamber of said SSS is adapted to contain an original semen sample having a volume measurement ranging from about 0.1 ml to about 10 ml; (d) said SSS is adapted for diagnostics of male infertility; and any combination thereof.

16. A naturally based method for separating at least a portion of sperm cell populations (SCP) characterized by (i) motility in a range between about 5 µm/s to about 15 µm/s at 37°; (ii) slow progressive motility in a range between about 15 minis at 37° to about 25 µm/s at 37°; (iii) rapid progressive motility of at least 25 µm/s at 37° and 20 µm/s at 20°; (iv) at least 90% motile sperm cells, having an average of at least 32% normal morphology; or any combination thereof, within an original semen sample into an enriched SCP sample, said method comprises steps of:

a. providing a cell separation device, comprising:
      i. at least one first chamber; said first chamber is bounded by a rim; wherein said rim is crenellated shaped; said first chamber is characterized by pre-determined 3D shape and volume, V; and,
      ii. at least one second chamber in physical communication with said first chamber and said rim;
   b. configuring said second chamber with pre-determined 3D shape and volume, $V_1$, wherein said $V_1$ is substantially smaller than pr equal to V;
   c. obtaining incubation means;
   d. socketing said cell separation device within said incubation means;
   e. depositing said original semen sample within said first chamber such that said original semen sample is kept below said rim;
   f. introducing a support medium into either said first chamber and/or said second chamber such that said support medium is in liquid communication with at least a portion of said original semen sample; thereby residing at least a portion of said SCP crossing through the crenellations in said crenellated shaped rim within said second chamber; and, g. separating said SCP from said original semen sample into said enriched sample;

wherein said step (b) of configuring said second chamber with predetermined 3D shape and performing said steps (d-g) while constantly and homogeneously thermoregulating the temperature within said cell separation device enables at least one of the following to be held true:

i. efficacy of said SSS is at least 95%;

ii. the total number of motile CSP separated into said second chamber is at least $4*10^6$ as examined with phase contrast or light microscopes, when said original semen sample is a NORMAL sample as defined by WHO 1999 Appendix IA clause 2.5 and comprises at least $5*10^6$ [motile CSP/ml];

iii. the concentration of motile CSP separated into said second chamber is at least $4*10^6$ [cell/ml] as measured with phase contrast or light microscopes when the concentration of motile CSP in said original semen sample is at least $5*10^6$ [motile sperm cell/ml];

iv. the total number of progressive motile CSP separated into said second chamber is at least $2*10^6$ as measured with phase contrast or light microscopes, when said original semen sample comprises at least $2.5*10^6$ [progressive motile CSP/ml];

v. the average percentage of CSP having normal morphology in said enriched sample is at least 32% in as measured with phase contrast or microscopes when said original semen sample comprises an average of at least 18% CSP having normal morphology.

17. The method according to claim 16, additionally comprising at least one step selected from (a) configuring said first chamber as dimpled-shaped; (b) configuring said $V_1$ to be equal to said V; (c) configuring said first chamber and said second in a co-axial manner such that said second chamber is peripheral and circumferentially encircles said first chamber; (d) configuring said first chamber and said second are in a side by side configuration; (e) configuring said first chamber and said second in a pile configuration; (f) configuring said pre-determined 3D shape of said first chamber with a circular cross sectional area having radius R; (g) configuring said pre-determined 3D shape of said second chamber with a circular cross sectional area having radius $R^1$; (h) configuring said pre-determined 3D shape of said first chamber with a cross sectional area having n ribs where n is an integer higher than or equals to 3, (i) configuring said pre-determined 3D shape of said second chamber with a cross sectional area having n ribs where n is an integer higher than or equals to 3, or any combination thereof; or any combination thereof; and any combination thereof.

18. The method according to claim 16, additionally comprising step of enabling said SCP to cross through or above the crenellations in said crenellated shaped rim into said second chamber upon introduction of a support medium into either said first chamber and/or said second chamber such that said support medium is in liquid communication with at least a portion of said original semen sample.

19. The method according to claim 16, wherein said steps (d-f) is performed while constantly and homogeneously thermoregulating the temperature within said cell separation device such that at least one of the following to be held true:

i. the total number of motile CSP separated into said second chamber is at least $4*10^6$ as examined with phase contrast or light microscopes, when said original semen sample is a NORMAL sample as defined by WHO 1999 Appendix IA clause 2.5;

ii. the concentration of motile CSP separated into said second chamber is at least $4*10^6$ [cell/ml] as measured with phase contrast or light microscopes when said original semen sample is a NORMAL sample as defined by WHO 1999 Appendix IA clause 2.5;

iii. the total number of progressive motile CSP separated into said second chamber is at least $2*10^6$ as measured with phase contrast or light microscopes, when said original semen sample is a NORMAL sample as defined by WHO 1999 Appendix IA clause 2.5;

iv. the average percentage of CSP having normal morphology in said enriched sample is at least 32%, as measured with phase contrast or light microscopes when said original semen sample is a NORMAL sample as defined by WHO 1999 Appendix IA clause 2.5;

v. the average % of motile sperm cells in said enriched sample in said second chamber is increased by an average of at least 210% relatively to the average % motile sperm cells in said original semen sample, as measured with phase contrast or light microscopes;

vi. the % of progressive motile CSP in said enriched sample in said second chamber is increased by an average of at least 290% relatively to the average % progressive motile CSP in said original semen sample, as measured with phase contrast or light microscopes;

vii. the % of CSP having normal morphology in said enriched sample in said second chamber is increased by an average of at least 260% relatively to the average % of CSP having normal morphology in said original semen sample, as measured with phase contrast or light microscopes;

viii. the average % of motile sperm cells isolated into said enriched sample is multiplied by at least 2.0 relatively to the average % motile sperm cells in said original semen sample as measured with phase contrast or light microscopes;

ix. the average % of progressive motile sperm cells isolated into said second chamber is multiplied by at least 1.4 relatively to the average % of progressive motile sperm cells in said original semen sample as measured with phase contrast or light microscopes;

x. the % of decrease said CSP having abnormal round cells morphology isolated into said second chamber is about 99% as measured with phase contrast or light microscopes.

20. The method according to claim 16, wherein said step of separating said SCP from said original semen sample additionally comprising at least one step selected from (a) providing said separated SCP depleted of round non motile cells selected from group of round non sperm cells, immature sperm cells, dead sperm cells or any combination thereof; (b) providing said separated SCP with an average of at least 70%, progressively motile sperm cells; (c) providing an average yield separation which is higher than 58%, relative to said original semen sample before said separation.

21. The method according to claim 16, additionally comprising at least one step selected from (a) performing assays selected from a group consisting of: a sperm cells concentration assay, a semen pH assay, a leukocytes concentration threshold assay, a sperm cells motility assay, a sperm cells morphology assay, a semen volume assay, a viscosity assay and a turbidity assay; (b) facilitating diagnosis of at least one sexually transmitted disease (STD) selected from a group consisting of: syphilis, gonorrhea, Candida, human papiloma virus (HPV), mycoplasma, ureaplasma, human immunodeficiency virus (HIV), Chlamydia, herpes simplex virus, Hepatitis B, Trichomonas and Hepatitis C; (c) providing said SSS as a SSS sealed such that no contamination of the environment outside said cartridge is provided; (d) providing said SSS with a reagent adapted to, upon contact with said original or enriched sample, to yield a reaction and/or a colored compound indicating (i) existence; or, (ii) concentration of a component in said original or enriched sample; (iii) a result of said at least one assay; said reagent is selected from a group consisting of cell support medium, labeling compounds, markers, peptide, color-changeable pad or any combination thereof.

22. The method according to claim 16, additionally comprising at least one step selected from (a) selecting said original sample is selected from a group consisting of: a semen sample, a vaginal secretion sample, a vaginal cell sample, a blood sample, a urine sample, a saliva sample, a lymph sample or any combination thereof; (b) configuring said SSS to be made of substantially rigid materials or a substantially flexible materials or any combination thereof.

23. The method according to claim 16, wherein said step of socketing said cell separation device within said incubation means is performed for a pre-determined period of about 10 minutes to about 60 minutes; further wherein said step of homogeneously thermoregulating the temperature within said cell separation device, thermoregulates the temperature to about 30 Celsius degrees and about 39 Celsius degrees.

24. The method according to claim 16, wherein said step of providing said cell separation device provides the same with a cover; said cover comprises at least two openings said orifices are adapted to enable guided entry or aspiration of fluids aspiration means or actuators to either said first central chamber or said second chamber; further wherein said actuators are selected from a group consisting of needle, cannula, pipette, syringe any positive displacement system such as a peristaltic pump or any combination thereof.

25. The method according to claim 16, additionally comprising step of assessing at least one selected from a group consisting of (a) motility of sperm cells and/or isolate motile sperm within an enriched semen sample for assisting fertility; (b) motility of sperm cells in said enriched semen sample, and/or isolate motile sperm of said semen sample for fertility treatments selected from a group consisting of: intra uterine insemination (WI), vaginal insemination, and in-vitro fertilization (IVF).

* * * * *